United States Patent
Galcera Contour et al.

(10) Patent No.: US 7,279,467 B2
(45) Date of Patent: Oct. 9, 2007

(54) BENZOTHIAZOLE-AND BENZOXAZOLE-4, 7-DIONE DERIVATIVES AND THEIR USE AS DCD25 PHOSPHATASE INHIBITORS

(75) Inventors: Marie-Odile Galcera Contour, Bondoufle (FR); Olivier Lavergne, Palaiseau (FR); Marie-Christine Brezak Pannetier, Antony (FR); Grégoire Prevost, Antony (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 222 days.

(21) Appl. No.: 10/500,411

(22) PCT Filed: Dec. 24, 2002

(86) PCT No.: PCT/FR02/04544

§ 371 (c)(1),
(2), (4) Date: Jun. 24, 2004

(87) PCT Pub. No.: WO03/055868

PCT Pub. Date: Jul. 10, 2003

(65) Prior Publication Data

US 2006/0040996 A1 Feb. 23, 2006

(30) Foreign Application Priority Data

Dec. 27, 2001 (FR) .................. 01 16889

(51) Int. Cl.
*A61K 31/428* (2006.01)
(52) U.S. Cl. ..................................... 514/179
(58) Field of Classification Search ................ 514/367
See application file for complete search history.

(56) References Cited

FOREIGN PATENT DOCUMENTS

WO  WO 01/45680  6/2001

OTHER PUBLICATIONS

Ryu, et al., "5-Arylamino-2-methyl-4,7-dioxobenzothiazoles as Inhibitors of Cyclin-Dependent Kinanse 4 and Cytotoxic Agents," Bioorganic & Medicinal Chemistry Letters, vol. 10, pp. 461-464 (2000).*

Lyon et al., "Synthesis and structure verification of an analog of kuanoniamine A," J. Chem. Soc. Perkin Transactions 1: Organic and Bio-Organic Chemistry, vol. 4, pp. 437-442 (1999).*

Kristjánsdóttir et al., "Cdc25 Phophatases and Cancer," Chemistry & Biology, vol. 11, p. 1043-1051 (Aug. 2004).*

Ryu et al., "5-arylamino-2-methyl-4,7-dioxobenzothiazoles as inhibitors of cyclin-dependent kinase 4 and cytotoxic agents," Bioorganic & Medicinal Chem. Letters, vol. 10, Iss. 5, pp. 461-464 (2000).*

Ryu et al., "Modulation of NAD(P)H:quinone oxidoreductase (NQO1) activity mediated by 5-arylamino-2-methyl-4,7-dioxobenzothiazoles and their cytotoxic potential," Archives of Pharmacal Research, vol. 23, Iss. 6, pp. 554-558 (2000).*

Ryu et al, "Synthesis . . . Dioxobenzothiazoles", Bioorganic & Medicinal Chemistry Letters, vol. 10, No. 14, Jul. 17, 2000 pp. 1589-1591.

Ryu et al, "5-Arylamino- . . . Cytotoxic Agents", Bioorganic & Medicinal Chemistry Letters, vol. 10, No. 5, Mar. 5, 2000, pp. 461-464.

* cited by examiner

*Primary Examiner*—Rebecca Anderson
*Assistant Examiner*—Andrew B. Freistein
(74) *Attorney, Agent, or Firm*—Hunton & Williams LLP

(57) ABSTRACT

The invention concerns the use as cdc25 phosphatase inhibitors, in particular cdc25-C phosphatase, and CD45 phosphatase, of compounds of general formula (I), wherein: W represents O or S. In accordance with the invention, the compounds of general formula (I) can in particular be used for preparing a medicine for cancer treatment

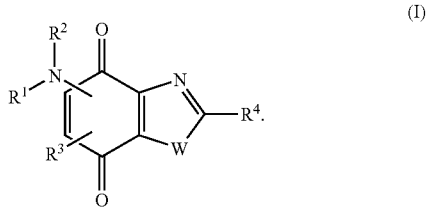

3 Claims, No Drawings

BENZOTHIAZOLE- AND BENZOXAZOLE-4, 7-DIONE DERIVATIVES AND THEIR USE AS DCD25 PHOSPHATASE INHIBITORS

This application is a 371 of PCT/FR02/04544 filed Dec. 24, 2002.

A subject of the present invention is novel derivatives of benzothiazole-4,7-dione and benzooxazole-4,7-dione, which inhibit the cdc25 phosphatases, in particular cdc25-C phosphatase, and/or CD45 phosphatase.

Control of the transition between the different phases of the cell cycle during mitosis or meiosis is ensured by a group of proteins the enzyme activities of which are associated with different states of phosphorylation. These states are controlled by two large classes of enzymes: the kinases and the phosphatases.

Synchronization of the different phases of the cell cycle thus allows reorganization of the cell architecture at each cycle in the whole of the living world (microorganisms, yeast, vertebrates, plants). Among the kinases, the cyclin-dependent kinases (CDKs) play a major role in this control of the cell cycle. The enzyme activity of these different CDKs is controlled by two other families of enzymes which work in opposition (Jessus and Ozon, *Prog. Cell Cycle Res.* (1995), 1, 215-228). The first includes kinases such as Wee1 and Mik1 which deactivate the CDKs by phosphorylating certain amino acids (Den Haese et al., *Mol. Biol. Cell* (1995), 6, 371-385). The second includes phosphatases such as Cdc25 which activate the CDKs by dephosphorylating tyrosine and threonine residues of CDKs (Gould et al., *Science* (1990), 250, 1573-1576).

The phosphatases are classified in 3 groups: the serine/threonine phosphatases (PPases), the tyrosine phosphatases (PTPases) and the dual-specificity phosphatases (DSPases). These phosphatases play an important role in the regulation of numerous cell functions.

As regards human cdc25 phosphatases, 3 genes (cdc25-A, cdc25-B and cdc25-C) code for the cdc25 proteins. Moreover, variants originating from alternative splicing of the cdc25B gene have been identified: these are cdc25B1, cdc25B2 and cdc25B3 (Baldin et al., *Oncogene* (1997), 14, 2485-2495).

The role of the Cdc25 phosphatases in oncogenesis is now better known and the action mechanisms of these phosphatases are illustrated in particular in the following references: Galaktionov et al., *Science* (1995), 269, 1575-1577; Galaktionov et al., *Nature* (1996), 382, 511-517; and Mailand et al., *Science* (2000), 288, 1425-1429.

In particular, the overexpression of the different forms of cdc25 is now reported in numerous series of human tumors:

Breast cancer: cf. Cangi et al., *Résumé* 2984, AACR meeting San Francisco, 2000);

Lymphomas: cf. Hernandez et al., *Int. J. Cancer* (2000), 89, 148-152 and Hernandez et al., *Cancer Res.* (1998), 58, 1762-1767;

Cancers of the neck and head: cf. Gasparotto et al., *Cancer Res.* (1997), 57, 2366-2368.

Moreover, E. Sausville's group reports an inverse correlation between the level of expression of cdc25-B in a panel of 60 lines and their sensitivities to CDK inhibitors, suggesting that the presence of cdc25 can bring a resistance to certain antineoplastic agents and more particularly to CDK inhibitors (Hose et al., *Proceedings of AACR*, Abstract 3571, San Francisco, 2000).

Among other targets, the pharmaceutical industry is therefore at present researching compounds capable of inhibiting the Cdc25 phosphatases in order to use them in particular as anti-cancer agents.

The Cdc25 phosphatases also play a role in neurodegenerative diseases such as Alzheimer's disease (cf. Zhou et al., *Cell Mol. Life Sci.* (1999), 56(9-10), 788-806; Ding et al., *Am. J. Pathol.* (2000), 157(6), 1983-90; Vincent et al., *Neuroscience* (2001), 105(3), 639-50) in such a manner that it is also possible to envisage using compounds possessing an inhibition activity on these phosphatases in order to treat these diseases.

Another problem addressed by the invention is research into medicaments intended to prevent or treat the rejection of organ grafts or also to treat auto-immune diseases. In these disorders/diseases, the non-appropriate activation of lymphocytes and monocytes/macrophages is involved. The immunosuppressive medicaments known at present have side effects which could be diminished or modified by products specifically targeting the signalling pathways in hematopoietic cells which initiate and maintain inflammation.

The CD45 phosphatase plays a crucial role in the transmission of signals from receptors on the T lymphocytes by regulating the phosphorylation and the activity of the tyrosine kinases of the src family, the negative regulation sites $p56^{lck}$ and $p59^{fyn}$ of which it is capable of dephosphorylating.

The CD45 phosphatase is therefore a potential target in the treatment of immune diseases. In fact, the blocking of the CD45 phosphatase by an anti-CD45 antibody inhibits the activation of the T lymphocytes in vitro (Prickett and Hart, *Immunology* (1990), 69, 250-256). Similarly, the T lymphocytes of transgenic mice not expressing CD45 (CD45 knockout mice) do not correspond to stimulation by an antigen (Trowbridge and Thomas, *Annu. Rev. Immunol.* (1994), 12, 85-116).

Moreover, CD45 would be capable of dephosphorylating a sub-unit associated with Lyn, which would trigger a flow of calcium and activation of the mastocytes. Hamaguchi et al. (*Bioorg. Med. Chem. Lett.* (2000), 10, 2657-2660) have shown that a particular CD45 inhibitor (with an $IC_{50}$ equal to 280 nM) would suppress the release of histamine from rat peritoneal mastocytes and would protect mice from anaphylactic shock.

The advantage of finding CD45 phosphatase inhibitors would therefore appear obvious in particular when there is interest in:

obtaining an immunosuppressive effect in general, and in particular:
within the scope of the treatment of auto-immune diseases (Zong et al., *J. Mol. Med.* (1998), 76(8), 572-580) such as for example multiple sclerosis or autoimmune encephalitis (Yacyshyn et al., *Dig. Dis. Sci.* (1996), 41(12), 2493-8) and diabetes (Shimada et al., *J. Autoimmun.* (1996), 9(2), 263-269);
within the scope of the treatment of transplant rejections;

in the treatment of inflammation in general, and in particular:
within the scope of the treatment of arthritis (Pelegri et al., *Clin. Exp. Immunol.* (2001), 125(3), 470-477), rheumatoid arthritis, rheumatic diseases, conjunctivitis (Iwamoto et al., *Graefes Arch. Clin. Opthalmol.* (1999), 237(5), 407-414) and pruritic diseases;
within the scope of the treatment of digestive inflammatory diseases such as for example Crohn's disease (Yacyshyn et al., *Dig. Dis. Sci.* (1996), 41(12), 2493-2498), haemorrhagic rectocolitis and hepatitis (Volpes et al., *Hepatology* (1991), 13(5), 826-829); and in the treatment of allergies (Pawlik et al., *Tohoku J. Exp. Med.* (1997), 182(1), 1-8).

The invention offers novel cdc25 phosphatase inhibitors (in particular cdc25-C phosphatase inhibitors), and/or CD45 phosphatase inhibitors, which are derivatives of benzothiazole-4,7-dione and benzooxazole-4,7-dione corresponding to the general formula (I) defined hereafter. Given the above, these compounds are capable of being used as medicaments, in particular in the treatment of the following diseases/disorders:

inhibition of tumorous proliferation alone or in combination with other treatments;
inhibition of normal cell proliferation alone or in combination with other treatments;
neurodegenerative diseases such as Alzheimer's disease;
prevention of spontaneous alopecia;
prevention of alopecia induced by exogenous products;
prevention of radiation-induced alopecia;
prevention of spontaneous or induced apoptosis of normal cells;
prevention of meiosis and fertilization;
prevention of the maturation of oocytes;
all the diseases/all the disorders corresponding to uses reported for CDK inhibitors, and in particular non-tumorous proliferative diseases (for example: angiogenesis, psoriasis or restenosis), tumorous proliferative diseases, parasitology (proliferation of protozoans), viral infections, neurodegenerative diseases, myopathies;
all the diseases/all the disorders corresponding to clinical uses of vitamin K and its derivatives;
autoimmune diseases such as for example multiple sclerosis and rheumatoid arthritis; and
diabetes.

Moreover, the compounds of the present invention are also, due to their cdc25 phosphatase inhibition properties, capable of being used to inhibit the proliferation of microorganisms, in particular yeasts. One of the advantages of these compounds is their low toxicity on healthy cells.

A certain number of derivatives of benzothiazole-4,7-dione and benzooxazole-4,7-dione are already known.

In particular, the patent GB 1 534 275 relates to herbicides, the active ingredient of which is a compound corresponding to one of the general formulae

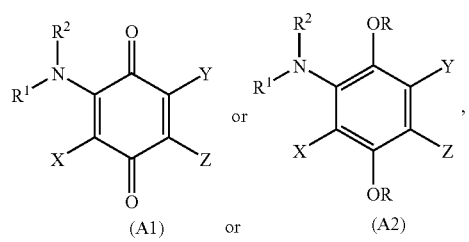

in which:
$R^1$ represents in particular a hydrogen atom or an alkyl or cycloalkyl radical;
$R^2$ represents in particular a hydrogen atom, an alkyl or cycloalkyl radical;
X represents in particular a halogen atom or an alkoxy radical;
Y and Z can in particular represent together with the carbon atoms which carry them a thiazole ring optionally substituted by an alkyl radical; and
R represents in particular an alkyl radical.

Moreover, the PCT Patent Application WO 99/32115 describes the compounds of general formula (A3)

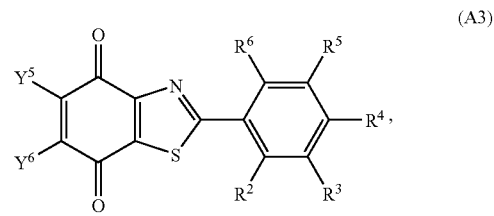

in which:
the substituents $R^2$-$R^6$ are chosen from the group constituted by a hydrogen atom, electron donor substituents, electron attractor substituents and electron modulator substituents; and $Y^5$ and $Y^6$ are in particular chosen from the group constituted by a hydrogen atom, electron-donor substituents, electron-attracting substituents and electron-modulating substituents.

In the PCT Patent Application WO 99/32115, the term "electron-donor substituent" refers to a functional group having a tendency to donate electron density; the substituents alkyl, alkenyl and alkynyl are mentioned. In this Patent Application, "electron-attracting substituents" always refers to a functional group having a tendency to attract electron density; the cyano, acyl, carbonyl, fluoro, nitro, sulphonyl and trihalomethyl substituents are mentioned. Finally, an "electron-modulating substituent" is defined in this Application as a functional group having a tendency to modulate the electron density, which can both attract and donate electrons and is therefore such that it can stabilize a cationic intermediate in an aromatic electrophilic substitution reaction; a functional group is mentioned, including, for example, amino (for example —$NH_2$, alkylamino or dialkylamino), hydroxy, alkoxy or aryl substituents, heterocyclic substituents, halogen atoms, etc.

The compounds of general formula (A3) are presented as ryanodine receptor modulators which can be used as pesticides or therapeutic agents, for example in the treatment of congestive cardiac failure, migraine headaches, hypertension, Parkinson's disease or Alzheimer's disease or in the prevention of miscarriage.

Finally, the benzooxazole-4,7-dione derivatives of general formula (A4)

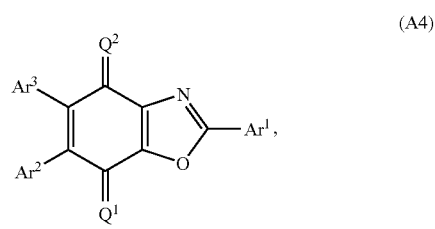

in which:
$Ar^1$ represents an optionally substituted aryl radical, each of Ar² and Ar³ represents a hydrogen atom or an optionally substituted aryl radical, and each of Q¹ and Q² represents in particular O, are described as active constituents of photosensitive layers of photoreceptors.

At present, the Applicant has surprisingly discovered that the compounds corresponding to the general formula (I)

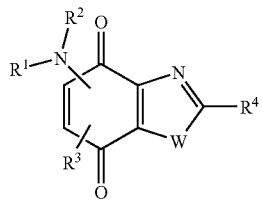

(I)

in which:

$R^1$ represents a hydrogen atom or an alkyl, alkoxyalkyl, alkylthioalkyl, cycloalkyl, —(CH₂)—X—Y, —(CH²)—Z—NR⁵R⁶ radical or a —CHR³⁵R³⁶ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR⁷—, —CO—, —NR⁸—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR⁹ radical and an NR¹⁰R¹¹ radical, $R^9$ representing a hydrogen atom or an alkyl or phenyl radical, and $R^{10}$ and $R^{11}$ representing independently alkyl radicals, Z representing a bond or a linear or branched alkylene radical containing 1 to 5 carbon atoms, $R^5$ and $R^6$ being chosen independently from a hydrogen atom, an alkyl, aralkyl or —(CH₂)ₙ—OH radical in which n represents an integer from 1 to 6, or $R^5$ representing an alkoxycarbonyl, haloalkoxycarbonyl or aralkoxycarbonyl radical and $R^6$ representing a hydrogen atom or a methyl radical, or also $R^5$ and $R^6$ forming together with the nitrogen atom a heterocycle with 4 to 7 members comprising 1 to 2 heteroatoms, the members necessary for completing the heterocycle being chosen independently from the —R¹²R¹³—, —O—, —S— and —NR¹⁴— radicals, $R^{12}$ and $R^{13}$ representing independently each time that they occur a hydrogen atom or an alkyl radical, and $R^{14}$ representing a hydrogen atom or an alkyl or aralkyl radical, or also $R^{14}$ representing a phenyl radical optionally substituted from 1 to 3 times by substituents chosen independently from a halogen atom and an alkyl or alkoxy radical, $R^2$ representing a hydrogen atom or an alkyl or aralkyl radical;

or also $R^1$ and $R^2$ forming together with the nitrogen atom a heterocycle with 4 to 8 members comprising 1 to 2 heteroatoms, the members necessary for completing the heterocycle being chosen independently from the —CR¹⁵R¹⁶—, —O—, —S— and —NR¹⁷— radicals, $R^{15}$ and $R^{16}$ representing independently each time that they occur a hydrogen atom or an alkyl radical, and $R^{17}$ representing a hydrogen atom or an alkyl or aralkyl radical;

$R^3$ represents a hydrogen atom, a halogen atom, or an alkyl, haloalkyl, alkoxy or alkylthio radical;

$R^4$ represents an alkyl, cycloalkyl, cycloalkylalkyl, cyano, amino, —CH₂—COOR¹⁸, —CH₂—CO—NR¹⁹R²⁰ or —CH²—NR²¹R²² radical, or $R^4$ represents a carbocyclic or heterocyclic aryl radical optionally substituted from 1 to 4 times by substituents chosen independently from a halogen atom and an alkyl, haloalkyl, alkoxy, haloalkoxy or NR³⁷R³⁸ radical, or also $R^4$ represents a phenyl radical possessing two substituents which form together a methylenedioxy or ethylenedioxy radical, $R^{18}$ representing a hydrogen atom or an alkyl radical, $R^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR²³ radical and an NR²⁴R²⁵ radical, $R^{23}$ representing a hydrogen atom or an alkyl or phenyl radical, and $R^{24}$ and $R^{25}$ representing independently alkyl radicals, $R^{20}$ representing a hydrogen atom or an alkyl radical, or also $R^{19}$ and $R^{20}$ forming together with the nitrogen atom a heterocycle with 4 to 7 members comprising 1 to 2 heteroatoms, the members necessary for completing the heterocycle being chosen independently from the —CR²⁶R²⁷—, —O—, —S— and —NR²⁸— radicals, $R^{26}$ and $R^{27}$ representing independently each time that they occur a hydrogen atom or an alkyl radical, and $R^{28}$ representing a hydrogen atom or an alkyl or aralkyl radical, or also $R^{28}$ representing a phenyl radical optionally substituted from 1 to 3 times by substituents chosen independently from a halogen atom and an alkyl or alkoxy radical, $R^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR²⁹ radical and an NR³⁰R³¹ radical, $R^{29}$ representing a hydrogen atom or an alkyl or phenyl radical, and $R^{30}$ and $R^{31}$ representing independently alkyl radicals, $R^{22}$ representing a hydrogen atom or an alkyl radical,
or also $R^{21}$ and $R^{22}$ forming together with the nitrogen atom a heterocycle with 4 to 7 members comprising 1 to 2 heteroatoms, the members necessary for completing the heterocycle being chosen independently from the —$CR^{32}R^{33}$—, —O—, —S— and —$NR^{34}$— radicals, $R^{32}$ and $R^{33}$ representing independently each time that they occur a hydrogen atom or an alkyl radical, and $R^{34}$ representing a hydrogen atom, an alkyl or aralkyl radical, or also $R^{34}$ representing a phenyl radical optionally substituted from 1 to 3 times by substituents chosen independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary for completing the heterocycle being chosen independently from the —$CR^{39}R^{40}$—, —O—, —S— and —$NR^{41}$— radicals, $R^{39}$ and $R^{40}$ representing independently each time that they occur a hydrogen atom or an alkyl radical, and $R^{41}$ representing a hydrogen atom or an alkyl radical; and W represents O or S;

or the pharmaceutically acceptable salts of compounds of general formula (I) defined above are cdc25 phosphatase inhibitors, and in particular cdc25-C phosphatase inhibitors, and/or CD 45 phosphatase inhibitors, and can therefore be used for preparing a medicament intended to inhibit the cdc25 phosphatases, and in particular the cdc25-C phosphatase, and/or the CD 45 phosphatase.

By alkyl, unless otherwise specified, is meant a linear or branched alkyl radical containing 1 to 12 carbon atoms, preferably 1 to 10 carbon atoms and more preferentially 1 to 8 carbon atoms (and in particular 1 to 6 carbon atoms). By cycloalkyl, unless otherwise specified, is meant a cycloalkyl radical containing 3 to 7 carbon atoms. By carbocyclic or heterocyclic aryl, is meant a carbocyclic or heterocyclic system with 1 to 3 condensed rings comprising at least one aromatic ring, a system being called heterocyclic when at least one of the rings which compose it comprises a heteroatom (O, N or S); when a carbocyclic or heterocyclic aryl radical is called substituted without further specification, it is meant that said carbocyclic or heterocyclic aryl radical is substituted 1 to 3 times, and preferably from once to twice by different radicals of a hydrogen atom which, unless otherwise specified, are chosen from a halogen atom and the alkyl or alkoxy radicals; moreover, unless otherwise specified, by aryl is meant exclusively a carbocyclic aryl. By haloalkyl, is meant an alkyl radical of which at least one of the hydrogen atoms (and optionally all) is replaced by a halogen atom.

By cycloalkylalkyl, alkoxy, haloalkyl, haloalkoxy and aralkyl radicals, is meant respectively the cycloalkylalkyl, alkoxy, haloalkyl, haloalkoxy and aralkyl radicals of which the alkyl, cycloalkyl and aryl radicals have the meanings indicated previously.

When it is indicated that a radical is optionally substituted from 1 to 3 times, it is preferably optionally substituted from once to twice and more preferentially optionally substituted once.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By haloalkyl, is meant in particular the trifluoromethyl radical. By haloalkoxy, is meant in particular the trifluoromethoxy radical. By aryl carbocyclic, is meant in particular the phenyl and naphthyl radicals. By aralkyl, is meant in particular the phenylalkyl radicals, and in particular the benzyl radical. By saturated carbon-containing cyclic system containing 1 to 3 condensed rings chosen independently from rings with 3 to 7 members, is meant in particular the cyclopropyl, cyclobutyl, cyclohexyl and adamantyl radicals. By heterocyclic or heteroaryl aryl, is meant in particular the thienyl, furanyl, pyrrolyl, imidazolyl, thiazolyl, oxazolyl and pyridyl radicals. Finally, by halogen, is meant the fluorine, chlorine, bromine or iodine atoms.

By pharmaceutically acceptable salt, is meant in particular addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, pamoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In certain cases, the compounds according to the present invention can comprise asymmetrical carbon atoms. As a result, the compounds according to the present invention have two possible enantiomeric forms, i.e. the "R" and "S" configurations. The present invention includes the two enantiomeric forms and all combinations of these forms, including the "RS" racemic mixtures. In an effort to simplify matters, when no specific configuration is indicated in the structural formulae, it should be understood that the two enantiomeric forms and their mixtures are represented.

According to a particular variant of the invention, the compounds of general formula (I) are compounds of general formula (I)'

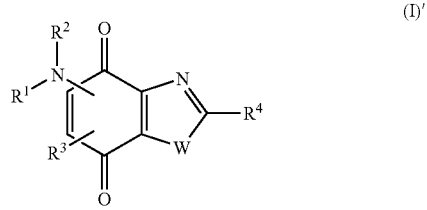

(I)' in which:
$R^1$ represents a hydrogen atom or an alkyl, alkoxyalkyl, alkylthioalkyl, cycloalkyl, —(CH$_2$)—X—Y, —(CH$^2$)—Z—$NR^5R^6$ radical or a —$CHR^{35}R^{36}$ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR$^7$—, —CO—, —NR$^8$—, —O— and —S—, R$^7$ representing a hydrogen atom or an alkyl radical and R$^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^9$ radical and an NR$^{10}$R$^{11}$ radical, R$^9$ representing a hydrogen atom or an alkyl or phenyl radical, and R$^{10}$ and R$^{11}$ representing independently alkyl radicals, Z representing a bond or a linear or branched alkylene radical containing 1 to 5 carbon atoms, R$^5$ and R$^6$ being chosen independently from a hydrogen atom, an alkyl, aralkyl or —(CH$_2$)$_n$—OH radical in which n represents an integer from 1 to 6, or R$^5$ representing an alkoxycarbonyl, haloalkoxycarbonyl or aralkoxycarbonyl radical and R$^6$ representing a hydrogen atom or a methyl radical, or also R$^5$ and R$^6$ forming together with the nitrogen atom a heterocycle with 4 to 7 members comprising 1 to 2 heteroatoms, the members necessary for completing the heterocycle being chosen independently from the —CR$^{12}$R$^{13}$—, —O—, —S— and —NR$^{14}$— radicals, R$^{12}$ and R$^{13}$ representing independently each time that they occur a hydrogen atom or an alkyl radical, and R$^{14}$ representing a hydrogen atom or an alkyl or aralkyl radical, or also R$^{14}$ representing a phenyl radical optionally substituted from 1 to 3 times by substituents chosen independently from a halogen atom and an alkyl or alkoxy radical, R$^2$ representing a hydrogen atom or an alkyl or aralkyl radical;

or also R$^1$ and R$^2$ forming together with the nitrogen atom a heterocycle with 4 to 8 members comprising 1 to 2 heteroatoms, the members necessary for completing the heterocycle being chosen independently from the —CR$^{15}$R$^{16}$—, —O—, —S— and —NR$^{17}$— radicals, R$^{15}$ and R$^{16}$ representing independently each time that they occur a hydrogen atom or an alkyl radical, and R$^{17}$ representing a hydrogen atom or an alkyl or aralkyl radical;

R$^3$ represents a hydrogen atom, a halogen atom, or an alkyl, haloalkyl, alkoxy or alkylthio radical;

R$^4$ represents an alkyl, cycloalkyl, cycloalkylalkyl, cyano, amino, —CH$_2$—COOR$^{18}$, —CH$_2$—CO—NR$^{19}$R$^{20}$ or —CH$^2$—NR$^{21}$R$^{22}$ radical, or also R$^4$ represents a carbocyclic or heterocyclic aryl radical optionally substituted from 1 to 3 times by substituents chosen independently from a halogen atom and an alkyl, haloalkyl, alkoxy or NR$^{37}$R$^{38}$ radical, R$^{18}$ representing a hydrogen atom or an alkyl radical, R$^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{23}$ radical and an NR$^{24}$R$^{25}$ radical, R$^{23}$ representing a hydrogen atom or an alkyl or phenyl radical, and R$^{24}$ and R$^{25}$ representing independently alkyl radicals, R$^{20}$ representing a hydrogen atom or an alkyl radical, or also R$^{19}$ and R$^{20}$ forming together with the nitrogen atom a heterocycle with 4 to 7 members comprising 1 to 2 heteroatoms, the members necessary for completing the heterocycle being chosen independently from the —CR$^{26}$R$^{27}$—, —O—, —S— and —NR$^{28}$— radicals, R$^{26}$ and R$^{27}$ representing independently each time that they occur a hydrogen atom or an alkyl radical, and R$^{28}$ representing a hydrogen atom or an alkyl or aralkyl radical, or also R$^{28}$ representing a phenyl radical optionally substituted from 1 to 3 times by substituents chosen independently from a halogen atom and an alkyl or alkoxy radical, R$^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{29}$ radical and an NR$^{30}$R$^{31}$ radical, R$^{29}$ representing a hydrogen atom or an alkyl or phenyl radical, and R$^{30}$ and R$^{31}$ representing independently alkyl radicals, R$^{22}$ representing a hydrogen atom or an alkyl radical, or also R$^{21}$ and R$^{22}$ forming together with the nitrogen atom a heterocycle with 4 to 7 members comprising 1 to 2 heteroatoms, the members necessary for completing the heterocycle being chosen independently from the —CR$^{32}$R$^{33}$—, —O—, —S— and —NR$^{34}$— radicals, R$^{32}$ and R$^{33}$ representing independently each time that they occur a hydrogen atom or an alkyl radical, and R$^{34}$ representing a hydrogen atom, an alkyl or aralkyl radical, or also R$^{34}$ representing a phenyl radical optionally substituted from 1 to 3 times by substituents chosen independently from a halogen atom and an alkyl or alkoxy radical, R$^{37}$ and R$^{38}$ being chosen independently from a hydrogen atom and an alkyl radical or R$^{37}$ and R$^{38}$ forming together with the nitrogen atom a heterocycle with 4 to 7 members comprising 1 to 2 heteroatoms, the members necessary for completing the heterocycle being chosen independently from the —CR$^{39}$R$^{40}$—, —O—, —S— and —NR$^{41}$— radicals, R$^{39}$ and R$^{40}$ representing independently each time that they occur a hydrogen atom or an alkyl radical, and R$^{41}$ representing a hydrogen atom or an alkyl radical; and W represents O or S;

or the pharmaceutically acceptable salts of compounds of general formula (I)' defined above.

According to a more particular variant of the invention, the compounds used according to the invention are compounds of general formula (I)"

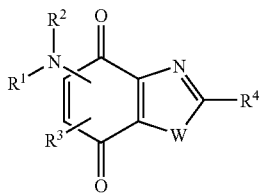

(I)″ in which:

R¹ represents a hydrogen atom or an alkyl, cycloalkyl, —(CH₂)—X—Y or —(CH₂)—Z—NR⁵R⁶ radical, R¹ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR⁷—, —CO—, —NR⁸, —O— and —S—, R⁷ representing a hydrogen atom or an alkyl radical and R⁸ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR⁹ radical and an NR¹⁰R¹¹ radical, R⁹ representing a hydrogen atom or an alkyl or phenyl radical, and R¹⁰ and R¹¹ representing independently alkyl radicals, Z representing a bond or a linear or branched alkylene radical containing 1 to 5 carbon atoms, R⁵ and R⁶ being chosen independently from a hydrogen atom, an alkyl, aralkyl or —(CH₂)ₙ—OH radical in which n represents an integer from 1 to 6, or R⁵ and R⁶ forming together with the nitrogen atom a heterocycle with 4 to 7 members comprising 1 to 2 heteroatoms, the members necessary for completing the heterocycle being chosen independently from the —CR¹²R¹³—, —O—, —S— and —NR¹⁴— radicals, R¹² and R¹³ representing independently each time that they occur a hydrogen atom or an alkyl radical, and R¹⁴ representing a hydrogen atom or an alkyl or aralkyl radical, or also R¹⁴ representing a phenyl radical optionally substituted from 1 to 3 times by substituents chosen independently from a halogen atom and an alkyl or alkoxy radical, R² representing a hydrogen atom or an alkyl radical;

or also R¹ and R² forming together with the nitrogen atom a heterocycle with 4 to 7 members comprising 1 to 2 heteroatoms, the members necessary for completing the heterocycle being chosen independently from the —CR¹⁵R¹⁶—, —O—, —S— and —NR¹⁷— radicals, R¹⁵ and R¹⁶ representing independently each time that they occur a hydrogen atom or an alkyl radical, and R¹⁷ representing a hydrogen atom or an alkyl or aralkyl radical;

R³ represents a hydrogen atom, a halogen atom, or an alkyl, haloalkyl or alkoxy radical;

R⁴ represents an alkyl, cycloalkyl, cycloalkylalkyl, cyano, amino, —CH₂—COOR¹⁸, —CH₂—CO—NR¹⁹R²⁰ or —CH²—NR²¹R²² radical, or also R⁴ represents a heterocyclic aryl radical optionally substituted from 1 to 3 times by substituents chosen independently from a halogen atom and an alkyl, haloalkyl or alkoxy radical, R¹⁸ representing a hydrogen atom or an alkyl radical, R¹⁹ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR²³ radical and an NR²⁴R²⁵ radical, R²³ representing a hydrogen atom or an alkyl or phenyl radical, and R²⁴ and R²⁵ representing independently alkyl radicals, R²⁰ representing a hydrogen atom or an alkyl radical, or also R¹⁹ and R²⁰ forming together with the nitrogen atom a heterocycle with 4 to 7 members comprising 1 to 2 heteroatoms, the members necessary for completing the heterocycle being chosen independently from the —CR²⁶R²⁷—, —O—, —S— and —NR²⁸— radicals, R²⁶ and R²⁷ representing independently each time that they occur a hydrogen atom or an alkyl radical, and R²⁸ representing a hydrogen atom or an alkyl or aralkyl radical, or also R²⁸ representing a phenyl radical optionally substituted from 1 to 3 times by substituents chosen independently from a halogen atom and an alkyl or alkoxy radical, R²¹ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO₂NHR²⁹ radical and an NR³⁰R³¹ radical, R²⁹ representing a hydrogen atom or an alkyl or phenyl radical, and R³⁰ and R³¹ representing independently alkyl radicals, R²² representing a hydrogen atom or an alkyl radical, or also R²¹ and R²² forming together with the nitrogen atom a heterocycle with 4 to 7 members comprising 1 to 2 heteroatoms, the members necessary for completing the heterocycle being chosen independently from the —CR³²R³³—, —O—, —S— and —NR³⁴— radicals, R³² and R³³ representing independently each time that they occur a hydrogen atom or an alkyl radical, and R³⁴ representing a hydrogen atom, an alkyl or aralkyl radical, or also R³⁴ representing a phenyl radical optionally substituted from 1 to 3 times by substituents chosen independently from a halogen atom and an alkyl or alkoxy radical; and W represents O or S;

or the pharmaceutically acceptable salts of compounds of general formula (I)″ defined above.

The uses according to the present invention also generally have four variants:

according to a first variant, the compounds of general formula (I) which also correspond to the general sub-formula (I)₁

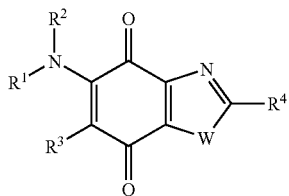

(I)$_1$ in which W represents S and $R^1$, $R^2$, $R^3$ and $R^4$ have the same meaning as in general formula (I), or their pharmaceutically acceptable salts, are used;

according to a second variant, the compounds of general formula (I) which also correspond to the general subformula (I)$_2$

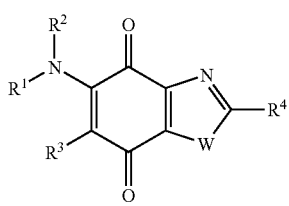

(I)$_2$ in which W represents O and $R^1$, $R^2$, $R^3$ and $R^4$ have the same meaning as in general formula (I), or their pharmaceutically acceptable salts, are used;

according to a third variant, the compounds of general formula (I) which also correspond to the general subformula (I)$_3$

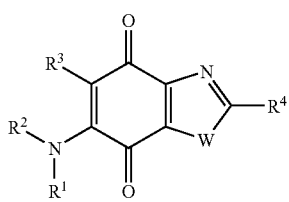

(I)$_3$ in which W represents S and $R^1$, $R^2$, $R^3$ and $R^4$ have the same meaning as in general formula (I), or their pharmaceutically acceptable salts, are used; and according to a fourth variant, the compounds of general formula (I) which also correspond to the general subformula (I)$_4$

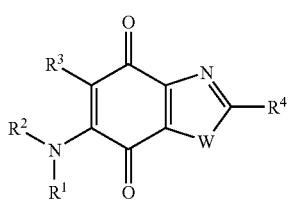

(I)$_4$ in which W represents O and $R^1$, $R^2$, $R^3$ and $R^4$ have the same meaning as in general formula (I), or their pharmaceutically acceptable salts, are used.

The invention therefore relates in particular to the use of compounds of general formula (I)$_1$ or (I)$_2$, or their pharmaceutically acceptable salts, for preparing a medicament intended to inhibit the cdc25 phosphatases, and in particular cdc25-C phosphatase, and/or CD45 phosphatase. Similarly, the invention relates to the use of compounds of general formula (I)$_3$ or (I)$_4$, or their pharmaceutically acceptable salts, for preparing a medicament intended to inhibit the cdc25 phosphatases, and in particular cdc25-C phosphatase, and/or CD45 phosphatase.

Preferably, the compounds of general formula (I), (I)', (I)", (I)$_1$, (I)$_2$, (I)$_3$ or (I)$_4$ used according to the invention will include at least one of the following characteristics:

$R^1$ representing an alkyl, cycloalkyl, alkoxyalkyl, —(CH$_2$)—X—Y, —(CH$_2$)—Z—NR$^5$R$^6$ or —CHR$^{35}$R$^{36}$ radical;

$R^2$ representing a hydrogen atom or the methyl, ethyl or benzyl radical;

$R^1$ and $R^2$ forming together with the nitrogen atom a heterocycle with 4 to 8 members (preferably 5 to 7 members, and in particular 6 members) comprising 1 to 2 heteroatoms (and preferably 2 heteroatoms), the members necessary for completing the heterocycle being chosen independently from the —CH$_2$—, —O— and —NR$^{17}$ radicals (and preferably from the —CH$_2$— and —NR$^{17}$— radicals), $R^{17}$ representing a methyl or benzyl radical;

$R^3$ representing a hydrogen atom, a halogen atom or an alkyl, alkoxy or alkylthio radical;

$R^4$ representing an alkyl, —CH$_2$—COOR$^{18}$ or —CH$^2$—CO—NR$^{19}$R$^{20}$ or —CH$_2$—NR$^{21}$R$^{22}$ radical or also a carbocyclic or heterocyclic aryl radical optionally substituted from 1 to 4 times (and in particular from 1 to 3 times) by substituents chosen independently from a halogen atom and an alkyl, haloalkyl, alkoxy or NR$^{37}$R$^{38}$ radical.

Generally, for a use according to the invention, the compounds of general formula (I), (I)' or (I)" will be preferred in which W represents a sulphur atom. Another interesting alternative for a use according to the invention will nevertheless consist of using the compounds of general formula (I), (I)' or (I)" in which W represents an oxygen atom.

Moreover, the X radical will preferably represent a bond or a linear alkylene radical containing 1 to 5 carbon atoms. Preferably also, the Y radical will represent a saturated carbon-containing cyclic system containing 1 to 3 condensed rings chosen independently from rings with 3 to 7 members, or Y will represent a carbocyclic aryl radical optionally substituted (preferably optionally substituted by 1 to 3 radicals chosen from a halogen atom and an alkyl, haloalkyl, alkoxy, haloalkoxy, SO$_2$NHR$^9$ or NR$^{10}$R$^{11}$ radical, and more preferentially optionally substituted by 1 to 3 radicals chosen from a halogen atom and an alkyl, alkoxy, SO$_2$NHR$^9$ or NR$^{10}$R$^{11}$ radical) or also Y will represent an optionally substituted heterocyclic aryl radical, said heterocyclic aryl radical being preferably chosen from the aryl radicals with 5 members (and in particular from the imidazolyl, thienyl or pyridinyl radicals) and preferably optionally substituted by 1 to 3 radicals chosen from a halogen atom and an alkyl, haloalkyl, alkoxy, haloalkoxy, SO$_2$NHR$^9$ or NR$^{10}$R$^{11}$ radical, and more preferentially optionally substituted by 1 to 3 radicals chosen from a halogen atom and an alkyl, alkoxy, SO$_2$NHR$^9$ or NR$^{10}$R$^{11}$ radical; $R^9$ will represent preferably a hydrogen atom and $R^{10}$ and $R^{11}$ will preferably represent radicals chosen independently from the alkyl radicals. The Z radical will preferably represent an alkylene radical containing 1 to 5 carbon atoms, and in particular a —$(CH_2)_p$— radical in which p represents an integer from 1 to 3 (p being preferably equal to 1 or 2 and more preferentially equal to 1). Preferably also, $R^5$ and $R^6$ are chosen independently from a hydrogen atom and an alkyl radical, or also $R^5$ and $R^6$ will form together with the nitrogen atom which carries them a heterocycle with 4 to 7 members comprising 1 to 2 heteroatoms, said heterocycle then being preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably by 1 to 3 methyl radicals); still more preferentially, $R^5$ and $R^6$ are chosen independently from alkyl or alkoxycarbonyl radicals (and in particular $R^5$ and $R^6$ are each a methyl or tert-butoxycarbonyl radical) or $R^5$ and $R^6$ will form together with the nitrogen atom which carries them a heterocycle with 4 to 7 members comprising 1 to 2 heteroatoms, said heterocycle then being preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably by 1 to 3 methyl radicals). $R^{18}$ will represent preferably a hydrogen atom or the methyl or ethyl radical.

Moreover, the $R^7$, $R^{12}$, $R^{13}$, $R^{15}$, $R^{16}$, $R^{26}$, $R^{27}$, $R^{39}$ and $R^{40}$ radicals are preferably chosen independently from a hydrogen atom and a methyl radical and the $R^8$, $R^{14}$, $R^{17}$, $R^{28}$ and $R^{41}$ radicals are preferably chosen independently from a hydrogen atom and a methyl or benzyl radical.

Moreover, with respect to $R^{19}$ and $R^{20}$, the cases will be preferred in which $R^{19}$ represents a hydrogen atom, an alkyl radical or a benzyl radical and $R^{20}$ represents a hydrogen atom or the methyl radical, as well as those in which $R^{19}$ and $R^{20}$ form together with the nitrogen atom which carries them a heterocycle with 4 to 7 members comprising 1 to 2 heteroatoms, said heterocycle then being preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably optionally substituted by 1 to 3 methyl radicals).

Moreover, with respect to $R^{21}$ and $R^{22}$, the cases will be preferred in which $R^{21}$ represents a hydrogen atom, an alkyl radical or a benzyl radical and $R^{22}$ represents a hydrogen atom or the methyl radical, as well as those in which $R^{21}$ and $R^{22}$ form together with the nitrogen atom which carries them a heterocycle with 4 to 7 members comprising 1 to 2 heteroatoms, said heterocycle then being preferably one of the optionally substituted azetidinyl, pyrrolidinyl, piperidinyl, piperazinyl, homopiperazinyl, morpholinyl and thiomorpholinyl radicals. With respect to the corresponding radicals $R^{32}$, $R^{33}$ and $R^{34}$, the latter are preferably such that $R^{32}$ and $R^{33}$ are chosen independently from a hydrogen atom and an alkyl radical and preferably from a hydrogen atom and a methyl radical (still more preferentially $R^{32}$ and $R^{33}$ both representing hydrogen atoms) and $R^{34}$ represents a hydrogen atom, an alkyl radical or a phenyl radical optionally substituted from 1 to 3 times by substituents chosen independently from a halogen atom and an alkyl or alkoxy radical ($R^{34}$ representing still more preferentially a hydrogen atom or a methyl or phenyl radical).

Moreover, with respect to $R^{35}$ and $R^{36}$, the cases will be preferred in which $R^{35}$ and $R^{36}$ form together with the carbon atom which carries them an indanyl radical or $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical.

Moreover, with respect to $R^{37}$ and $R^{38}$, the cases will be preferred in which $R^{37}$ and $R^{38}$ represent independently radicals chosen from the alkyl radicals.

Finally, when $R^4$ is a carbocyclic or heterocyclic aryl radical optionally substituted from 1 to 4 times, it is preferably chosen from the group consisting of carbocyclic and heterocyclic aryl radicals optionally substituted from 1 to 3 times by substituents chosen independently from a halogen atom and an alkyl, haloalkyl, alkoxy, haloalkoxy or $NR^{37}R^{38}$ radical (and in particular from 1 to 3 times by substituents chosen independently from a halogen atom and an alkyl, haloalkyl, alkoxy or haloalkoxy radical) and the 2,3,4,5-tetrafluorophenyl radical. More preferentially, when $R^4$ is a carbocyclic or heterocyclic aryl radical optionally substituted from 1 to 4 times, $R^4$ is chosen from the group consisting of carbocyclic and heterocyclic aryl radicals optionally substituted from once to twice by substituents chosen independently from a halogen atom, an alkyl, haloalkyl, alkoxy, haloalkoxy or $NR^{37}R^{38}$ radical (and in particular from once to twice by substituents chosen independently from a halogen atom and an alkyl, haloalkyl, alkoxy or haloalkoxy radical), a 3,4,5-trihalophenyl radical and the 2,3,4,5-tetrafluorophenyl radical.

More preferentially, the compounds of general formula (I), (I)', (I)", (I)$_1$, (I)$_2$, (I)$_3$ or (I)$_4$ used according to the invention will include at least one of the following characteristics:

$R^1$ representing an alkyl, cycloalkyl, or —(CH$_2$)—Z—NR$^5$R$^6$ radical;

$R^2$ representing a hydrogen atom or the methyl radical;

$R^3$ representing a hydrogen atom, a halogen atom or the methoxy radical;

$R^4$ representing an alkyl, —CH$_2$—NR$^{21}$R$^{22}$ radical, or also a carbocyclic or heterocyclic aryl radical optionally substituted from 1 to 4 times (and in particular from 1 to 3 times) by substituents chosen independently from a halogen atom and an alkyl, or NR$^{37}$R$^{38}$ radical.

Still more preferentially, the compounds of general formula (I), (I)', (I)", (I)$_1$, (I)$_2$, (I)$_3$ or (I)$_4$ used according to the invention will include at least one of the following characteristics:

$R^1$ representing a —(CH$_2$)—Z—NR$^5$R$^6$ radical;

$R^2$ representing a hydrogen atom;

$R^3$ representing a hydrogen atom or a halogen atom (said halogen atom being preferably a chlorine or bromine atom);

$R^4$ representing an alkyl radical or also a phenyl, pyridyl, thienyl or furanyl radical optionally substituted by 1 to 4 (preferably 1 to 3) halogen atoms or by an NR$^{37}$R$^{38}$ radical.

In yet more particularly preferred fashion, the compounds of general formula (I), (I)', (I)", (I)$_1$, (I)$_2$, (I)$_3$ or (I)$_4$ used according to the invention will include at least one of the following characteristics:

$R^3$ representing a hydrogen atom or a chlorine atom (and more preferentially a hydrogen atom);

$R^4$ representing an alkyl radical or also a phenyl, pyridyl, thienyl furanyl radical optionally substituted by 1 to 4 (preferably 1 to 3) halogen atoms (and in particular $R^4$ representing an alkyl radical, and preferably an alkyl radical containing 1 to 4 carbon atoms, and still more preferentially a methyl or ethyl radical).

According to a particular variant of the invention, W represents O. In this particular case, it is preferable that $R^1$ represents an aryl radical, and in particular a phenyl radical, optionally substituted from 1 to 3 times by substituents chosen independently from a halogen atom and an alkyl, haloalkyl or alkoxy radical. More preferentially still, when W represents O, it is preferable that $R^1$ represents a phenyl radical optionally substituted by a halogen atom (said atom halogen preferably being a fluorine atom).

According to a particular aspect of the invention, $R^4$ will represent a phenyl radical or a heterocyclic aryl radical with 5 to 6 members optionally substituted from 1 to 4 times (and preferably from 1 to 3 times) by substituents chosen from the group consisting of halogen atoms, the trifluoromethyl radical and the trifluoromethoxy radical (and preferably chosen from the group consisting of halogen atoms and the trifluoromethyl radical). In particular, said optionally substituted heterocyclic aryl with 5 to 6 members is an optionally substituted pyridine, thiophene, furan or pyrrole ring.

Another particular aspect of this invention relates to the use of compounds of general formula (I) in which W represents S, $R^3$ represents a hydrogen atom, the —$NR^1R^2$ substituent (the preferences indicated previously for $R^1$ and $R^2$ remaining applicable) is attached at position 5 of the benzothiazoledione ring and $R^4$ is chosen from the alkyl, cycloalkylalkyl, —$CH_2$—$COOR^{18}$, —$CH^2$—$CO$—$NR^{19}R^{20}$ and —$CH_2$—$NR^{21}R^{22}$ radicals ($R^4$ being preferably alkyl or cycloalkylalkyl and more preferentially alkyl according to this particular aspect of the invention).

For a use according to the invention, the compounds of general formula (I) described (if appropriate in the form of salts or mixtures) in Examples 1 to 131, or the pharmaceutically acceptable salts of such compounds, are particularly preferred (in particular those described in Examples 1 to 65 or their pharmaceutically acceptable salts and in particular those described in Examples 1 to 17 or their pharmaceutically acceptable salts). From the compounds of Examples 1 to 131 and their pharmaceutically acceptable salts, the compounds of Examples 1 to 14, 18 to 39, 48 to 52, 55, 57, 58 and 60 to 131 (and in particular the compounds of Examples 1 to 14, 18 to 39 and 55 and their pharmaceutically acceptable salts) will generally be of greater interest for this invention.

Moreover, the compounds of general formula (I) described (if appropriate in the form of salts or mixtures) in Examples 2 to 5, 16, 19 to 26, 32, 34, 38 to 40, 43 to 47, 55 to 58, 60 to 77, 79 to 98 and 101 to 115, or the pharmaceutically acceptable salts of such compounds, are also more particularly preferred for a use according to the invention.

Moreover, the compounds of general formula (I) described (if appropriate in the form of salts or mixtures) in Examples 2, 19, 20, 23, 24, 34, 57, 60, 62, 63, 67 to 77, 80 to 92, 94, 96 to 98, 103, 104, 106 and 110 to 113, or the pharmaceutically acceptable salts of such compounds, are quite particularly preferred for a use according to the invention:

Another subject of the invention relates, as medicaments, to the compounds of general formula $(I)_M$

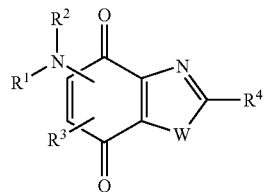

in which
$R^1$ represents a hydrogen atom or an alkyl, alkoxyalkyl, alkylthioalkyl, cycloalkyl, —$(CH_2)$—X—Y, —$(CH^2)$—Z—$NR^5R^6$ radical or a —$CHR^{35}R^{36}$ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —$CHR^7$—, —$CO$—, —$NR^8$—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^9$ radical and an $NR^{10}R^{11}$ radical, $R^9$ representing a hydrogen atom or an alkyl or phenyl radical, and $R^{10}$ and $R^{11}$ representing independently alkyl radicals, Z representing a bond or a linear or branched alkylene radical containing 1 to 5 carbon atoms, $R^5$ and $R^6$ being chosen independently from a hydrogen atom, an alkyl, aralkyl or —$(CH_2)_n$—OH radical in which n represents an integer from 1 to 6, or $R^5$ representing an alkoxycarbonyl, haloalkoxycarbonyl or aralkoxycarbonyl radical and $R^6$ representing a hydrogen atom or a methyl radical, or also $R^5$ and $R^6$ forming together with the nitrogen atom a heterocycle with 4 to 7 members comprising 1 to 2 heteroatoms, the members necessary for completing the heterocycle being chosen independently from the —$CR^{12}R^{13}$—, —O—, —S— and —$NR^{14}$— radicals, $R^{12}$ and $R^{13}$ representing independently each time that they occur a hydrogen atom or an alkyl radical, and $R^{14}$ representing a hydrogen atom or an alkyl or aralkyl radical, or also $R^{14}$ representing a phenyl radical optionally substituted from 1 to 3 times by substituents chosen independently from a halogen atom and an alkyl or alkoxy radical, $R^2$ representing a hydrogen atom or an alkyl or aralkyl radical; or also $R^1$ and $R^2$ forming together with the nitrogen atom a heterocycle with 4 to 8 members comprising 1 to 2 heteroatoms, the members necessary for completing the heterocycle being chosen independently from the —$CR^{15}R^{16}$—, —O—, —S— and —$NR^{17}$— radicals, $R^{15}$ and $R^{16}$ representing independently each time that they occur a hydrogen atom or an alkyl radical, and $R^{17}$ representing a hydrogen atom or an alkyl or aralkyl radical;

$R^3$ represents a hydrogen atom, a halogen atom, or an alkyl, haloalkyl, alkoxy or alkylthio radical;

$R^4$ represents an alkyl, cycloalkyl, cycloalkylalkyl, cyano, amino, —$CH_2$—$COOR^{18}$, —$CH_2$—CO—$NR^{19}R^{20}$ or —$CH^2$—$NR^{21}R^{22}$ radical, or $R^4$ represents a carbocyclic or heterocyclic aryl radical optionally substituted from 1 to 4 times by substituents chosen independently from a halogen atom and an alkyl, haloalkyl, alkoxy, haloalkoxy or $NR^{37}R^{38}$ radical, or also $R^4$ represents a phenyl radical possessing two substituents which form together a methylenedioxy or ethylenedioxy radical, $R^{18}$ representing a hydrogen atom or an alkyl radical, $R^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{23}$ radical and an $NR^{24}R^{25}$ radical, $R^{23}$ representing a hydrogen atom or an alkyl or phenyl radical, and $R^{24}$ and $R^{25}$ representing independently alkyl radicals, $R^{20}$ representing a hydrogen atom or an alkyl radical, or also $R^{19}$ and $R^{20}$ forming together with the nitrogen atom a heterocycle with 4 to 7 members comprising 1 to 2 heteroatoms, the members necessary for completing the heterocycle being chosen independently from the —$CR^{26}R^{27}$—, —O—, —S— and —$NR^{28}$— radicals, $R^{26}$ and $R^{27}$ representing independently each time that they occur a hydrogen atom or an alkyl radical, and $R^{28}$ representing a hydrogen atom or an alkyl or aralkyl radical, or also $R^{28}$ representing a phenyl radical optionally substituted from 1 to 3 times by substituents chosen independently from a halogen atom and an alkyl or alkoxy radical, $R^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{29}$ radical and an $NR^{30}R^{31}$ radical, $R^{29}$ representing a hydrogen atom or an alkyl or phenyl radical, and $R^{30}$ and $R^{31}$ representing independently alkyl radicals, $R^{22}$ representing a hydrogen atom or an alkyl radical, or also $R^{21}$ and $R^{22}$ forming together with the nitrogen atom a heterocycle with 4 to 7 members comprising 1 to 2 heteroatoms, the members necessary for completing the heterocycle being chosen independently from the —$CR^{32}R^{33}$—, —O—, —S— and —$NR^{34}$— radicals, $R^{32}$ and $R^{33}$ representing independently each time that they occur a hydrogen atom or an alkyl radical, and $R^{34}$ representing a hydrogen atom, an alkyl or aralkyl radical, or also $R^{34}$ representing a phenyl radical optionally substituted from 1 to 3 times by substituents chosen independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary for completing the heterocycle being chosen independently from the —$CR^{39}R^{40}$—, —O—, —S— and —$NR^{41}$— radicals, $R^{39}$ and $R^{40}$ representing independently each time that they occur a hydrogen atom or an alkyl radical, and $R^{41}$ representing a hydrogen atom or an alkyl radical; and W represents O or S;

it being understood that if W represents S and $R^4$ represents an optionally substituted aryl radical, then $R^1$ is chosen from the alkoxyalkyl, alkylthioalkyl, cycloalkyl, —($CH_2$)—X—Y and —($CH_2$)—Z—$NR^5R^6$ substituents;

and the pharmaceutically acceptable salts of the compounds of general formula $(I)_M$.

According to a particular variant of the invention, the medicaments are the compounds of general formula $(I)'_M$

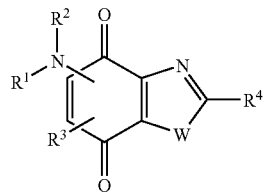

$(I)'_M$ in which $R^1$ represents a hydrogen atom or an alkyl, alkoxyalkyl, alkylthioalkyl, cycloalkyl, —($CH_2$)—X—Y, —($CH^2$)—Z—$NR^5R^6$ radical or a —$CHR^{35}R^{36}$ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —$CHR^7$—, —CO—, —$NR^8$—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^9$ radical and an $NR^{10}R^{11}$ radical, $R^9$ representing a hydrogen atom or an alkyl or phenyl radical, and $R^{10}$ and $R^{11}$ representing independently alkyl radicals, Z representing a bond or a linear or branched alkylene radical containing 1 to 5 carbon atoms, $R^5$ and $R^6$ being chosen independently from a hydrogen atom, an alkyl, aralkyl or —$(CH_2)_n$—OH radical in which n represents an integer from 1 to 6, or $R^5$ representing an alkoxycarbonyl, haloalkoxycarbonyl or aralkoxycarbonyl radical and $R^6$ representing a hydrogen atom or a methyl radical, or also $R^5$ and $R^6$ forming together with the nitrogen atom a heterocycle with 4 to 7 members comprising 1 to 2 heteroatoms, the members necessary for completing the heterocycle being chosen independently from the —$CR^{12}R^{13}$—, —O—, —S— and —$NR^{14}$— radicals, $R^{12}$ and $R^{13}$ representing independently each time that they occur a hydrogen atom or an alkyl radical, and $R^{14}$ representing a hydrogen atom or an alkyl or aralkyl radical, or also $R^{14}$ representing a phenyl radical optionally substituted from 1 to 3 times by substituents chosen independently from a halogen atom and an alkyl or alkoxy radical, $R^2$ representing a hydrogen atom or an alkyl or aralkyl radical;

or also $R^1$ and $R^2$ forming together with the nitrogen atom a heterocycle with 4 to 8 members comprising 1 to 2 heteroatoms, the members necessary for completing the heterocycle being chosen independently from the —$CR^{15}R^{16}$—, —O—, —S— and —$NR^{17}$— radicals, $R^{15}$ and $R^{16}$ representing independently each time that they occur a hydrogen atom or an alkyl radical, and $R^{17}$ representing a hydrogen atom or an alkyl or aralkyl radical;

$R^3$ represents a hydrogen atom, a halogen atom, or an alkyl, haloalkyl, alkoxy or alkylthio radical;

$R^4$ represents an alkyl, cycloalkyl, cycloalkylalkyl, cyano, amino, —$CH_2$—$COOR^{18}$, —$CH_2$—CO—$NR^{19}R^{20}$ or —$CH_2$—$NR^{21}R^{22}$ radical, or also $R^4$ represents a carbocyclic or heterocyclic aryl radical optionally substituted from 1 to 3 times by substituents chosen independently from a halogen atom and an alkyl, haloalkyl, alkoxy or $NR^{37}R^{38}$ radical, $R^{18}$ representing a hydrogen atom or an alkyl radical, $R^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{23}$ radical and an $NR^{24}R^{25}$ radical, $R^{23}$ representing a hydrogen atom or an alkyl or phenyl radical, and $R^{24}$ and $R^{25}$ representing independently alkyl radicals, $R^{20}$ representing a hydrogen atom or an alkyl radical, or also $R^{19}$ and $R^{20}$ forming together with the nitrogen atom a heterocycle with 4 to 7 members comprising 1 to 2 heteroatoms, the members necessary for completing the heterocycle being chosen independently from the —$CR^{26}R^{27}$—, —O—, —S— and —$NR^{28}$— radicals, $R^{26}$ and $R^{27}$ representing independently each time that they occur a hydrogen atom or an alkyl radical, and $R^{28}$ representing a hydrogen atom or an alkyl or aralkyl radical, or also $R^{28}$ representing a phenyl radical optionally substituted from 1 to 3 times by substituents chosen independently from a halogen atom and an alkyl or alkoxy radical, $R^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{29}$ radical and an $NR^{30}R^{31}$ radical, $R^{29}$ representing a hydrogen atom or an alkyl or phenyl radical, and $R^{30}$ and $R^{31}$ representing independently alkyl radicals, $R^{22}$ representing a hydrogen atom or an alkyl radical, or also $R^{21}$ and $R^{22}$ forming together with the nitrogen atom a heterocycle with 4 to 7 members comprising 1 to 2 heteroatoms, the members necessary for completing the heterocycle being chosen independently from the —$CR^{32}R^{33}$—, —O—, —S— and —$NR^{34}$— radicals, $R^{32}$ and $R^{33}$ representing independently each time that they occur a hydrogen atom or an alkyl radical, and $R^{34}$ representing a hydrogen atom, an alkyl or aralkyl radical, or also $R^{34}$ representing a phenyl radical optionally substituted from 1 to 3 times by substituents independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary for completing the heterocycle being chosen independently from the —$CR^{39}R^{40}$—, —O—, —S— and —$NR^{41}$— radicals, $R^{39}$ and $R^{40}$ representing independently each time that they occur a hydrogen atom or an alkyl radical, and $R^{41}$ representing a hydrogen atom or an alkyl radical; and W represents O or S;

it being understood that if W represents S and $R^4$ represents an optionally substituted aryl radical, then $R^1$ is chosen from the substituents alkoxyalkyl, alkylthioalkyl, cycloalkyl, —$(CH_2)$—X—Y and —$(CH_2)$—Z—$NR^5R^6$;

and the pharmaceutically acceptable salts of the compounds of general formula $(I)'_M$.

In the case where W represents S and $R^4$ represents an optionally substituted aryl radical the compounds of general formula $(I)_M$ or $(I)'_M$ in which $R^1$ is chosen from the substituents —$(CH_2)$—Z—$NR^5R^6$ are particularly preferred.

A subject of the invention is also, as medicaments, the compounds of general formula (I)" or their pharmaceutically acceptable salts. It similarly relates to the pharmaceutical compositions comprising, as active ingredient, at least one of the compounds of general formula (I)", $(I)_M$ or $(I)'_M$ as defined above or a pharmaceutically acceptable salt of such a compound.

The invention also relates to the compounds of general formula (II)

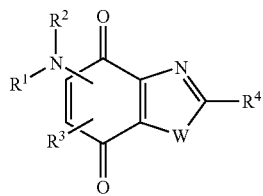

(II)

in which:

R$^1$ represents a hydrogen atom or an alkyl, alkoxyalkyl, alkylthioalkyl, cycloalkyl, —(CH$_2$)—X—Y, —(CH$^2$)—Z—NR$^5$R$^6$ radical or a —CHR$^{35}$R$^{36}$ radical in which R$^{35}$ and R$^{36}$ form together with the carbon atom which carries them an indanyl or tetralinyl radical, or also R$^{35}$ and R$^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, R$^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR$^7$—, —CO—, —NR$^8$—, —O— and —S—, R$^7$ representing a hydrogen atom or an alkyl radical and R$^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^9$ radical and an NR$^{10}$R$^{11}$ radical, R$^9$ representing a hydrogen atom or an alkyl or phenyl radical, and R$^{10}$ and R$^{11}$ representing independently alkyl radicals, Z representing a bond or a linear or branched alkylene radical containing 1 to 5 carbon atoms, R$^5$ and R$^6$ being chosen independently from a hydrogen atom, an alkyl, aralkyl or —(CH$_2$)$_n$—OH radical in which n represents an integer from 1 to 6, or R$^5$ representing an alkoxycarbonyl, haloalkoxycarbonyl or aralkoxycarbonyl radical and R$^6$ representing a hydrogen atom or a methyl radical, or also R$^5$ and R$^6$ forming together with the nitrogen atom a heterocycle with 4 to 7 members comprising 1 to 2 heteroatoms, the members necessary for completing the heterocycle being chosen independently from the —CR$^{12}$R$^{13}$—, —O—, —S— and —NR$^{14}$— radicals, R$^{12}$ and R$^{13}$ representing independently each time that they occur a hydrogen atom or an alkyl radical, and R$^{14}$ representing a hydrogen atom or an alkyl or aralkyl radical, or also R$^{14}$ representing a phenyl radical optionally substituted from 1 to 3 times by substituents chosen independently from a halogen atom and an alkyl or alkoxy radical, R$^2$ representing a hydrogen atom or an alkyl or aralkyl radical;

or also R$^1$ and R$^2$ forming together with the nitrogen atom a heterocycle with 4 to 8 members comprising 1 to 2 heteroatoms, the members necessary for completing the heterocycle being chosen independently from the —CR$^{15}$R$^{16}$—, —O—, —S— and —NR$^{17}$— radicals, R$^{15}$ and R$^{16}$ representing independently each time that they occur a hydrogen atom or an alkyl radical, and R$^{17}$ representing a hydrogen atom or an alkyl or aralkyl radical;

R$^3$ represents a hydrogen atom, a halogen atom, or an alkyl, haloalkyl, alkoxy or alkylthio radical;

R$^4$ represents an alkyl, cycloalkyl, cycloalkylalkyl, cyano, amino, —CH$_2$—COOR$^{18}$, —CH$_2$—CO—NR$^{19}$R$^{20}$ or —CH$^2$—NR$^{21}$R$^{22}$ radical, or R$^4$ represents a carbocyclic or heterocyclic aryl radical optionally substituted from 1 to 4 times by substituents chosen independently from a halogen atom and an alkyl, haloalkyl, alkoxy, haloalkoxy or NR$^{37}$R$^{38}$ radical, or also R$^4$ represents a phenyl radical possessing two substituents which form together a methylenedioxy or ethylenedioxy radical, R$^{18}$ representing a hydrogen atom or an alkyl radical, R$^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{23}$ radical and an NR$^{24}$R$^{25}$ radical, R$^{23}$ representing a hydrogen atom or an alkyl or phenyl radical, and R$^{24}$ and R$^{25}$ representing independently alkyl radicals, R$^{20}$ representing a hydrogen atom or an alkyl radical, or also R$^{19}$ and R$^{20}$ forming together with the nitrogen atom a heterocycle with 4 to 7 members comprising 1 to 2 heteroatoms, the members necessary for completing the heterocycle being chosen independently from the —CR$^{26}$R$^{27}$—, —O—, —S— and —NR$^{28}$— radicals, R$^{26}$ and R$^{27}$ representing independently each time that they occur a hydrogen atom or an alkyl radical, and R$^{28}$ representing a hydrogen atom or an alkyl or aralkyl radical, or also R$^{28}$ representing a phenyl radical optionally substituted from 1 to 3 times by substituents chosen independently from a halogen atom and an alkyl or alkoxy radical, R$^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{29}$ radical and an NR$^{30}$R$^{31}$ radical, R$^{29}$ representing a hydrogen atom or an alkyl or phenyl radical, and R$^{30}$ and R$^{31}$ representing independently alkyl radicals, R$^{22}$ representing a hydrogen atom or an alkyl radical, or also R$^{21}$ and R$^{22}$ forming together with the nitrogen atom a heterocycle with 4 to 7 members comprising 1 to 2 heteroatoms, the members necessary for completing the heterocycle being chosen independently from the —CR$^{32}$R$^{33}$—, —O—, —S— and —NR$^{34}$— radicals, R$^{32}$ and R$^{33}$ representing independently each time that they occur a hydrogen atom or an alkyl radical, and R$^{34}$ representing a hydrogen atom, an alkyl or aralkyl radical, or also $R^{34}$ representing a phenyl radical optionally substituted from 1 to 3 times by substituents chosen independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary for completing the heterocycle being chosen independently from the —$CR^{39}R^{40}$—, —O—, —S— and —$NR^{41}$— radicals, $R^{39}$ and $R^{40}$ representing independently each time that they occur a hydrogen atom or an alkyl radical, and $R^{41}$ representing a hydrogen atom or an alkyl radical; and W represents O or S;

it being understood that:
if W represents S and $R^4$ represents an alkyl radical, then $R^1$ does not represent a hydrogen atom or an alkyl or cycloalkyl radical and/or $R^3$ represents a hydrogen atom or an alkyl radical,
if W represents S and $R^4$ represents an optionally substituted aryl radical, then $R^1$ is chosen from the alkoxyalkyl, alkylthioalkyl, cycloalkyl, —$(CH_2)$—X—Y and —$(CH_2)$—Z—$NR^5R^6$ substituents;

as well as the salts of the compounds of general formula (II).

According to a particular variant of the invention, the compounds of general formula (II) are compounds of general formula (II)'

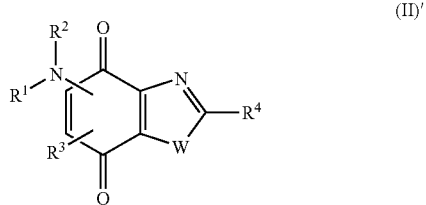

(II)' in which:
$R^1$ represents a hydrogen atom or an alkyl, alkoxyalkyl, alkylthioalkyl, cycloalkyl, —$(CH_2)$—X—Y, —$(CH_2)$—Z—$NR^5R^6$ radical or a —$CHR^{35}R^{36}$ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —$CHR^7$—, —CO—, —$NR^8$—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^9$ radical and an $NR^{10}R^{11}$ radical, $R^9$ representing a hydrogen atom or an alkyl or phenyl radical, and $R^{10}$ and $R^{11}$ representing independently alkyl radicals, Z representing a bond or a linear or branched alkylene radical containing 1 to 5 carbon atoms, $R^5$ and $R^6$ being chosen independently from a hydrogen atom, an alkyl, aralkyl or —$(CH_2)_n$—OH radical in which n represents an integer from 1 to 6, or $R^5$ representing an alkoxycarbonyl, haloalkoxycarbonyl or aralkoxycarbonyl radical and $R^6$ representing a hydrogen atom or a methyl radical, or also $R^5$ and $R^6$ forming together with the nitrogen atom a heterocycle with 4 to 7 members comprising 1 to 2 heteroatoms, the members necessary for completing the heterocycle being chosen independently from the —$CR^{12}R^{13}$—, —O—, —S— and —$NR^{14}$— radicals, $R^{12}$ and $R^{13}$ representing independently each time that they occur a hydrogen atom or an alkyl radical, and $R^{14}$ representing a hydrogen atom or an alkyl or aralkyl radical, or also $R^{14}$ representing a phenyl radical optionally substituted from 1 to 3 times by substituents chosen independently from a halogen atom and an alkyl or alkoxy radical, $R^2$ representing a hydrogen atom or an alkyl or aralkyl radical;

or also $R^1$ and $R^2$ forming together with the nitrogen atom a heterocycle with 4 to 8 members comprising 1 to 2 heteroatoms, the members necessary for completing the heterocycle being chosen independently from the —$CR^{15}R^{16}$—, —O—, —S— and —$NR^{17}$— radicals, $R^{15}$ and $R^{16}$ representing independently each time that they occur a hydrogen atom or an alkyl radical, and $R^{17}$ representing a hydrogen atom or an alkyl or aralkyl radical;

$R^3$ represents a hydrogen atom, a halogen atom, or an alkyl, haloalkyl, alkoxy or alkylthio radical;

$R^4$ represents an alkyl, cycloalkyl, cycloalkylalkyl, cyano, amino, —$CH_2$—$COOR^{18}$, —$CH_2$—CO—$NR^{19}R^{20}$ or —$CH_2$—$NR^{21}R^{22}$ radical, or also $R^4$ represents a carbocyclic or heterocyclic aryl radical optionally substituted from 1 to 3 times by substituents chosen independently from a halogen atom and an alkyl, haloalkyl, alkoxy or $NR^{37}R^{38}$ radical, $R^{18}$ representing a hydrogen atom or an alkyl radical, $R^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{23}$ radical and an $NR^{24}R^{25}$ radical, $R^{23}$ representing a hydrogen atom or an alkyl or phenyl radical, and $R^{24}$ and $R^{25}$ representing independently alkyl radicals, $R^{20}$ representing a hydrogen atom or an alkyl radical, or also $R^{19}$ and $R^{20}$ forming together with the nitrogen atom a heterocycle with 4 to 7 members comprising 1 to 2 heteroatoms, the members necessary for completing the heterocycle being chosen independently from the —$CR^{26}R^{27}$—, —O—, —S— and —$NR^{28}$— radicals, $R^{26}$ and $R^{27}$ representing independently each time that they occur a hydrogen atom or an alkyl radical, and $R^{28}$ representing a hydrogen atom or an alkyl or aralkyl radical, or also $R^{28}$ representing a phenyl radical optionally substituted from 1 to 3 times by substituents chosen independently from a halogen atom and an alkyl or alkoxy radical, $R^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{29}$ radical and an $NR^{30}R^{31}$ radical, $R^{29}$ representing a hydrogen atom or an alkyl or phenyl radical, and $R^{30}$ and $R^{31}$ representing independently alkyl radicals, $R^{22}$ representing a hydrogen atom or an alkyl radical, or also $R^{21}$ and $R^{22}$ forming together with the nitrogen atom a heterocycle with 4 to 7 members comprising 1 to 2 heteroatoms, the members necessary for completing the heterocycle being chosen independently from the —$CR^{32}R^{33}$—, —O—, —S— and —$NR^{34}$— radicals, $R^{32}$ and $R^{33}$ representing independently each time that they occur a hydrogen atom or an alkyl radical, and $R^{34}$ representing a hydrogen atom, an alkyl or aralkyl radical, or also $R^{34}$ representing a phenyl radical optionally substituted from 1 to 3 times by substituents chosen independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary for completing the heterocycle being chosen independently from the —$CR^{39}R^{40}$—, —O—, —S— and —$NR^{41}$— radicals, $R^{39}$ and $R^{40}$ representing independently each time that they occur a hydrogen atom or an alkyl radical, and $R^{41}$ representing a hydrogen atom or an alkyl radical; and W represents O or S;

it being understood that:

if W represents S and $R^4$ represents an alkyl radical, then $R^1$ does not represent a hydrogen atom or an alkyl or cycloalkyl radical and/or $R^3$ represents a hydrogen atom or an alkyl radical, if W represents S and $R^4$ represents an optionally substituted aryl radical, then $R^1$ is chosen from the alkoxyalkyl, alkylthioalkyl, cycloalkyl, —($CH_2$)—X—Y and —($CH_2$)—Z—$NR^5R^6$ substituents;

or salts of compounds of general formula (II)'.

According to a more particular variant of the invention, the compounds of general formula (II)' are compounds of general formula (II)"

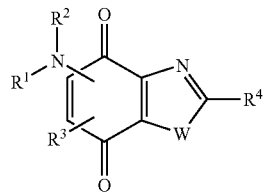

in which:

$R^1$ represents a hydrogen atom or an alkyl, cycloalkyl, —($CH_2$)—X—Y or —($CH_2$)—Z—$NR^5R^6$ radical, $R^1$ also being able, when W represents O, to represent moreover a carbocyclic aryl radical optionally substituted from 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —$CHR^7$—, —CO—, —$NR^8$—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^9$ radical and an $NR^{10}R^{11}$ radical, $R^9$ representing a hydrogen atom or an alkyl or phenyl radical, and $R^{10}$ and $R^{11}$ representing independently alkyl radicals, Z representing a bond or a linear or branched alkylene radical containing 1 to 5 carbon atoms, $R^5$ and $R^6$ being chosen independently from a hydrogen atom, an alkyl radical, aralkyl or —($CH_2$)$_n$—OH in which n represents an integer from 1 to 6, or $R^5$ and $R^6$ forming together with the nitrogen atom a heterocycle with 4 to 7 members comprising 1 to 2 heteroatoms, the members necessary for completing the heterocycle being chosen independently from the —$CR^{12}R^{13}$—, —O—, —S— and —$NR^{14}$— radicals, $R^{12}$ and $R^{13}$ representing independently each time that they occur a hydrogen atom or an alkyl radical, and $R^{14}$ representing a hydrogen atom or an alkyl or aralkyl radical, or also $R^{14}$ representing a phenyl radical optionally substituted from 1 to 3 times by substituents chosen independently from a halogen atom and an alkyl or alkoxy radical, $R^2$ representing a hydrogen atom or an alkyl radical;

or also $R^1$ and $R^2$ forming together with the nitrogen atom a heterocycle with 4 to 7 members comprising 1 to 2 heteroatoms, the members necessary for completing the heterocycle being chosen independently from the —$CR^{15}R^{16}$—, —O—, —S— and —$NR^{17}$— radicals, $R^{15}$ and $R^{16}$ representing independently each time that they occur a hydrogen atom or an alkyl radical, and $R^{17}$ representing a hydrogen atom or an alkyl or aralkyl radical;

$R^3$ represents a hydrogen atom, a halogen atom, or an alkyl, haloalkyl or alkoxy radical;

$R^4$ represents an alkyl, cycloalkyl, cycloalkylalkyl, cyano, amino, —$CH_2$—$COOR^{18}$, —$CH_2$—$CO$—$NR^{19}R^{20}$ or —$CH_2$—$NR^{21}R^{22}$ radical, or also $R^4$ represents a heterocyclic aryl radical optionally substituted from 1 to 3 times by substituents chosen independently from a halogen atom, an alkyl, haloalkyl or alkoxy radical, $R^{18}$ representing a hydrogen atom or an alkyl radical, $R^{19}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{23}$ radical and an $NR^{24}R^{25}$ radical, $R^{23}$ representing a hydrogen atom or an alkyl or phenyl radical, and $R^{24}$ and $R^{25}$ representing independently alkyl radicals, $R^{20}$ representing a hydrogen atom or an alkyl radical, or also $R^{19}$ and $R^{20}$ forming together with the nitrogen atom a heterocycle with 4 to 7 members comprising 1 to 2 heteroatoms, the members necessary for completing the heterocycle being chosen independently from the —$CR^{26}R^{27}$—, —O—, —S— and —$NR^{28}$— radicals, $R^{26}$ and $R^{27}$ representing independently each time that they occur a hydrogen atom or an alkyl radical, and $R^{28}$ representing a hydrogen atom or an alkyl or aralkyl radical, or also $R^{28}$ representing a phenyl radical optionally substituted by a halogen atom, an alkyl or alkoxy radical, $R^{21}$ representing a hydrogen atom, an alkyl radical or an aralkyl radical the aryl group of which is optionally substituted from 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{29}$ radical and an $NR^{30}R^{31}$ radical, $R^{29}$ representing a hydrogen atom or an alkyl or phenyl radical, and $R^{30}$ and $R^{31}$ representing independently alkyl radicals, $R^{22}$ representing a hydrogen atom or an alkyl radical, or also $R^{21}$ and $R^{22}$ forming together with the nitrogen atom a heterocycle with 4 to 7 members comprising 1 to 2 heteroatoms, the members necessary for completing the heterocycle being chosen independently from the —$CR^{32}R^{33}$—, —O—, —S— and —$NR^{34}$— radicals, $R^{32}$ and $R^{33}$ representing independently each time that they occur a hydrogen atom or an alkyl radical, and $R^{34}$ representing a hydrogen atom, an alkyl or aralkyl radical, or also $R^{34}$ representing a phenyl radical optionally substituted by a halogen atom or an alkyl or alkoxy radical; and W represents O or S;

it being understood that if W represents S and $R^4$ represents an alkyl radical, then $R^1$ represents —$(CH_2)$—X—Y or —$(CH^2)$—Z—$NR^5R^6$ and/or $R^3$ represents a hydrogen atom, or an alkyl radical;

as well as the salts of the compounds of general formula (II)".

Generally, compounds of general formula (II), (II)' or in which $R^1$ represents —$(CH_2)$—X—Y or —$(CH^2)$—Z—$NR^5R^6$ will be preferred, since W represents S and $R^4$ represents an alkyl radical.

Preferably, the compounds of general formula (I), (I)', (I)", $(I)_1$, $(I)_2$, $(I)_3$, $(I)_4$, $(I)_M$, $(I)'_M$, (II), (II)' or (II)" or their pharmaceutically acceptable salts are used for preparing a medicament intended to treat a disease chosen from the following diseases/the following disorders: tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies.

Quite particularly, the compounds of general formula (I), (I)', (I)", $(I)_1$, $(I)_2$, $(I)_3$, $(I)_4$, $(I)_M$, $(I)'_M$, (II), (II)' or (II)" or their pharmaceutically acceptable salts can be used for preparing a medicament intended to treat cancer, and in particular breast cancer, lymphomas, cancers of the neck and head, lung cancer, cancer of the colon, prostate cancer and cancer of the pancreas.

According to a particular variant of the invention, the compounds of general formula (I), (I)', (I)", $(I)_1$, $(I)_2$, $(I)_3$, $(I)_4$, $(I)_M$, $(I)'_M$, (II), (II)' or (II)" or their pharmaceutically acceptable salts can be used for preparing a medicament intended to treat spontaneous alopecia, alopecia induced by exogenous products or radiation-induced alopecia.

A subject of the invention is also a method for the treatment of tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies, said method comprising the administration of a therapeutically effective dose of a compound of general formula (I), (I)', (I)", $(I)_1$, $(I)_2$, $(I)_3$, $(I)_4$, $(I)_M$, $(I)'_M$, (or of a compound of general formula (II), (II)' or (II)") to a patient needing this treatment.

Generally, the same preferences as those indicated for the uses of compounds of general formula (I), (I)' (I)", $(I)_1$, $(I)_2$, $(I)_3$ or $(I)_4$ are moreover applicable by analogy to the medicaments, pharmaceutical compositions and compounds according to the invention, whether the latter relate to the compounds of general formula (I), (I)', (I)", $(I)_1$, $(I)_2$, $(I)_3$, $(I)_4$, $(I)_M$, $(I)'_M$ or those of general formula (II), (II)' or (11)".

The pharmaceutical compositions containing a compound of the invention can be presented in the form of solids, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be done by topical, oral, parenteral route, by intramuscular injection, etc.

The administration dose envisaged for a medicament according to the invention is comprised between 0.1 mg to 10 g depending on the type of active compound used.

According to the invention, the compounds of general formula (I) (or those of general formula (II) which are all also compounds of general formula (I)) can be prepared for example by the processes described hereafter.

Preparation of the Compounds of General Formula (I)

The preparation processes hereafter are given by way of illustration and a person skilled in the art can subject them to the variations that he deems useful, both with respect to the reagents and to the conditions and techniques of the reactions.

General Method

Generally, the compounds of general formula (I) can be prepared according to the procedure summarized in Diagram 1 below.

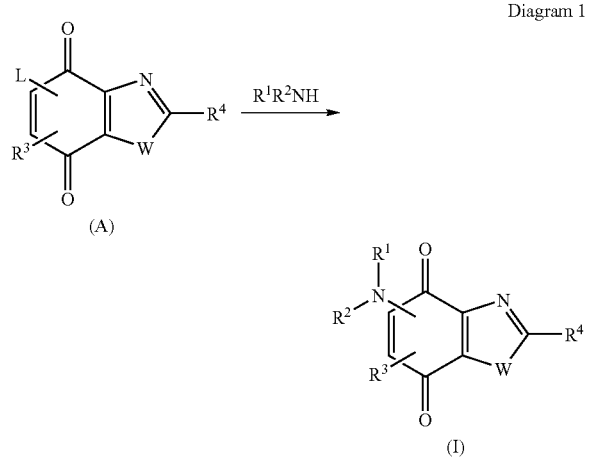

Diagram 1

According to this method, the compounds of general formula (I), in which $R^1$, $R^2$, $R^3$, $R^4$ and W are as described above, are obtained by treating the compounds of general formula (A), in which L represents a methoxy radical, a halogen atom or a hydrogen atom and $R^3$, $R^4$ and W have the same meaning as in general formula (I), with amines of general formula $NR^1R^2H$ in a protic solvent such as methanol or ethanol, at a temperature comprised between 0° C. and 50° C. and optionally in the presence of a base such as, for example, diisopropylethylamine (Yasuyuki Kita et al., *J. Org. Chem.* (1996), 61, 223-227).

In the particular case where the compounds of general formula (A) are such that L and $R^3$ each represent a halogen atom, the compounds of general formula (I) can be obtained in the form of a mixture of the 2 position isomers, but it is then possible to separate them by chromatography on a silica column in an appropriate eluent.

Alternatively, the compounds of general formula (I) in which $R^3$ represents a halogen atom (Hal) can be obtained, Diagram 1a, from the compounds of general formula (I) in which $R^3$ represents a hydrogen atom, for example, by the action of N-chlorosuccinimide or N-bromosuccinimide in an aprotic solvent such as dichloromethane or tetrahydrofuran (Paquette et Farley, *J. Org. Chem.* (1967), 32, 2725-2731), by the action of an aqueous solution of sodium hypochlorite (bleach) in a solvent such as acetic acid (Jagadeesh et al., *Synth Commun.* (1998), 28, 3827-3833), by the action of Cu(II) (in a $CuCl_2/HgCl_2$ mixture) in the presence of a catalytic quantity of iodine in a solvent such as warm acetic acid (Thaphyal, *Synth. Commun.* (1998), 28, 1123-1126), by the action of an agent such as benzyltrimethylammonium dichloroiodate in the presence of $NaHCO_3$ in a solvent such as a dichloromethane/methanol mixture (Kordik and Reitz, *J. Org. Chem.* (1996), 61, 5644-5645), or also by using chlorine, bromine or iodine in a solvent such as dichloromethane (J. Renault, S. Giorgi-Renault et al., *J. Med. Chem.* (1983), 26, 1715-1719).

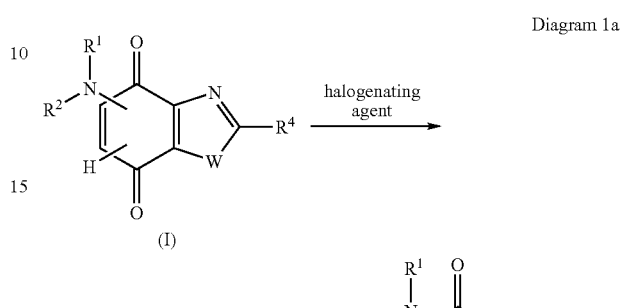

Diagram 1a

Alternatively, the compounds of general formula (I) in which $R^3$ represents an alkoxy or alkylthio radical can also be obtained, Diagram 1b, from the compounds of general formula (I) in which $R^3$ represents a halogen atom, for example, by the action of an alcohol of general formula $R^{3'}$—OH or of a thiol of general formula $R^{3'}$—SH($R^{3'}$ being such that $R^3=R^{3'}O$ or $R^{3'}S$) in a solvent such as anhydrous ethanol in the presence of a base such as, for example, diisopropylethylamine.

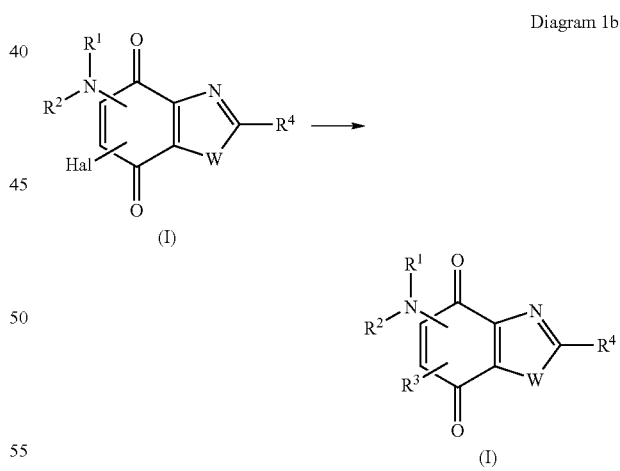

Diagram 1b

Preparation of the Intermediates of General Formula (A),

The compounds of general formula (A) in which L, $R^3$, $R^4$ and W are as defined above can be obtained, Diagram 2, starting from the compounds of general formula (B) in which L, $R^3$, $R^4$ and W are as defined above and:

one of Q and Q' represents an amino or hydroxyl radical and the other represents a hydrogen atom; or Q and Q' each represent an amino radical; or Q and Q' each represent a hydroxy radical; or finally Q and Q' each represent a methoxy radical.

Diagram 2

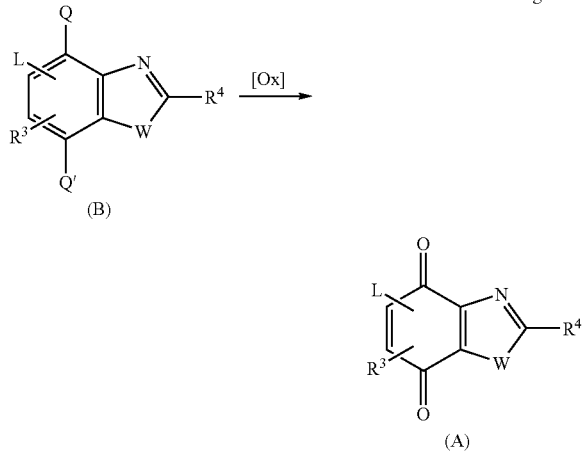

In the case where the compounds of general formula (B) are such that Q and Q' represent methoxy radicals, the compounds of general formula (A) are obtained by treatment with cerium (IV) and ammonium nitrate (Beneteau et al., *Eur. J. Med. Chem.* (1999), 34(12), 1053-1060). In the other cases, the compounds of general formula (A) are obtained by oxidation of the compounds of general formula (B), for example by use of FeCl$_3$ in an acid medium (Antonini et al., *Heterocycles* (1982), 19(12), 2313-2317) or Fremy's salt (potassium nitrosodisulphonate). (Ryu et al., *Bioorg. Med. Chem. Lett.* (2000), 10, 461-464), or by the use of a reagent comprising a hypervalent iodine such as [bis(acetoxy)iodo]benzene or [bis(trifluoroacetoxy)iodo]benzene in aqueous acetonitrile at a temperature preferably comprised between −20° C. and ambient temperature (i.e. approximately 25° C.), and preferably at approximately −5° C. (Kinugawa et al., *Synthesis*, (1996), 5, 633-636).

In the particular case where L and R$^3$ represent halogen atoms, the compounds of general formula (A) can be obtained, Diagram 3, by halogen oxidation of the compounds of general formula (B) in which L and R$^3$ represent hydrogen atoms and Q and/or Q' is (are) chosen from an amino radical and a hydroxy radical by the action, for example, of potassium or sodium perchlorate in an acid medium (Ryu et al., *Bioorg. Med. Chem. Lett.* (1999), 9, 1075-1080).

Diagram 3

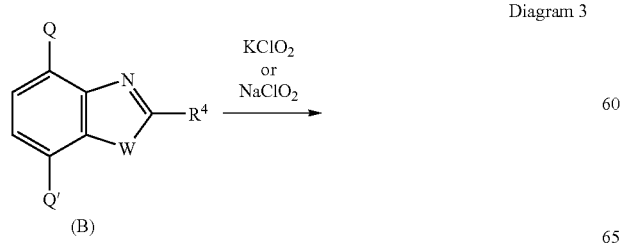

Preparation of the Intermediates of General Formula (B)

Certain compounds of general formula (B) in which L, R$^3$, R$^4$, Q, Q' and W are as defined above are known industrial products available from the usual suppliers.

If they are not commercially available and in the particular case where Q or Q' represents an amino radical, the compounds of general formula (B) can in particular be obtained from the nitro derivatives of formula (B.ii) in which Q or Q' represents a nitro radical by reduction methods which are well known to a person skilled in the art such as, for example, hydrogenation in the presence of a palladium catalyst or treatment with tin chloride in hydrochloric acid. If they are not commercially available, the compounds of formula (B.ii) can themselves be obtained from the compounds of general formula (B.i) in which the positions corresponding to the Q and Q' radicals are substituted by hydrogen atoms by nitration methods which are well known to a person skilled in the art such as, for example, treatment with a mixture of nitric acid and sulphuric acid (cf. Diagram 4 where only the case in which the compounds of general formula (B) are such that Q=NH$_2$ and Q'=H is represented).

Diagram 4

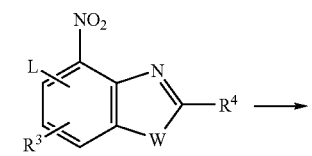

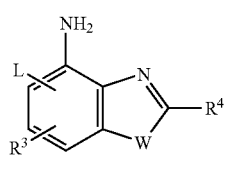

Alternatively, the compounds of general formula (B) which are not commercially available in which Q represents an amino radical, Q' a hydrogen atom and W an oxygen atom, can be obtained by treatment of the tetrahydrobenzoxazoles of general formula (B.vi) with hydroxylamine hydrochloride in order to produce the oximes of general formula (B.v), themselves treated with warm polyphosphoric acid (cf. Young Kook Koh et al., *J. Heterocyclic Chem.* (2001), 38, 89-92) to provide the compounds of general formula (B). The compounds of general formula (B.vi) can themselves be obtained from the cyclic 1,3-diketones of general formula (B.viii) firstly by conversion to diazodiketones of general formula (B.vii) by diazotransfer reaction, for example, by the action of tosyl azide or 4-acetamidobenzene sulphonyl azide in the presence of triethylamine in a solvent such as anhydrous dichloromethane or chloroform (V. V. Popic et al., *Synthesis* (1991), 3, 195-198) followed by cycloaddition of these diazodiketones of general formula (B.vii) with the nitrites of general formula $R^4$—CN in the presence of a rhodium-type catalyst (II) (Y. R. Lee, *Heterocycles* (1998), 48, 875-883) (cf. Diagram 4a).

leads to the intermediates of general formula (B.ix) in which Hal is a halogen atom), then β-elimination of the halogen by treatment with a base. The halogenation can be done, for example, using bromine in acetic acid at ambient temperature, pyridinium tribromide in acetic acid at 50° C., copper bromide (II) in ethyl acetate or acetonitrile under reflux, or also phenylselenyl chloride in ethyl acetate at ambient temperature. The elimination of the resultant halide can be carried out by diazabicyclo[5.4.0]undec-7-ene (DBU) in tetrahydrofuran at ambient temperature or by lithium carbonate in dimethylformamide. Examples of these reactions are provided by M. Tany et al., *Chem. Pharm. Bull.* (1996), 44, 55-61; M. A. Ciufolini et al., *J. Am. Chem. Soc.* (1995), 117, 12460-12469; and M. E. Jung and L. S. Starkey, *Tetrahedron* (1997), 53, 8815-8824.

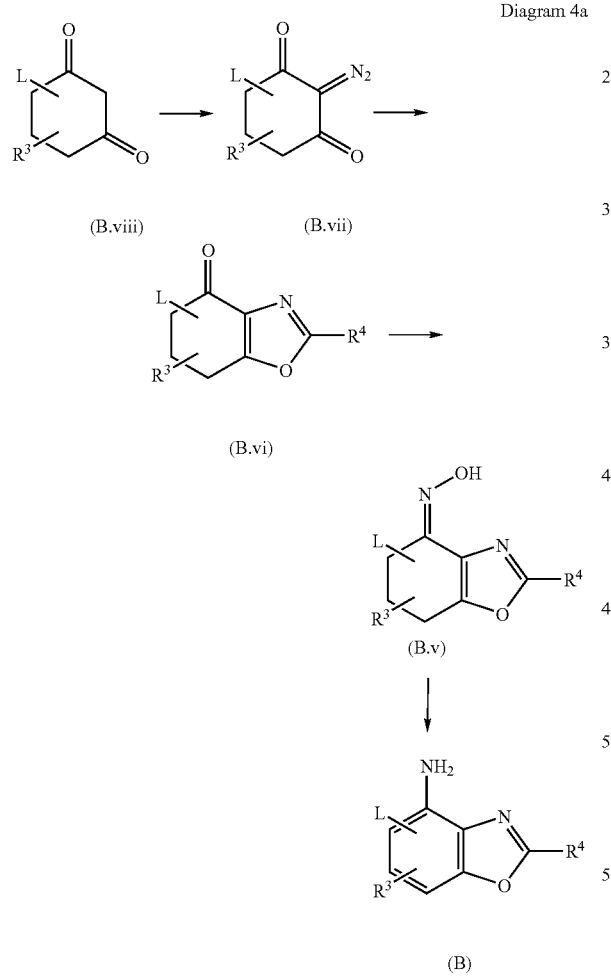

Diagram 4a

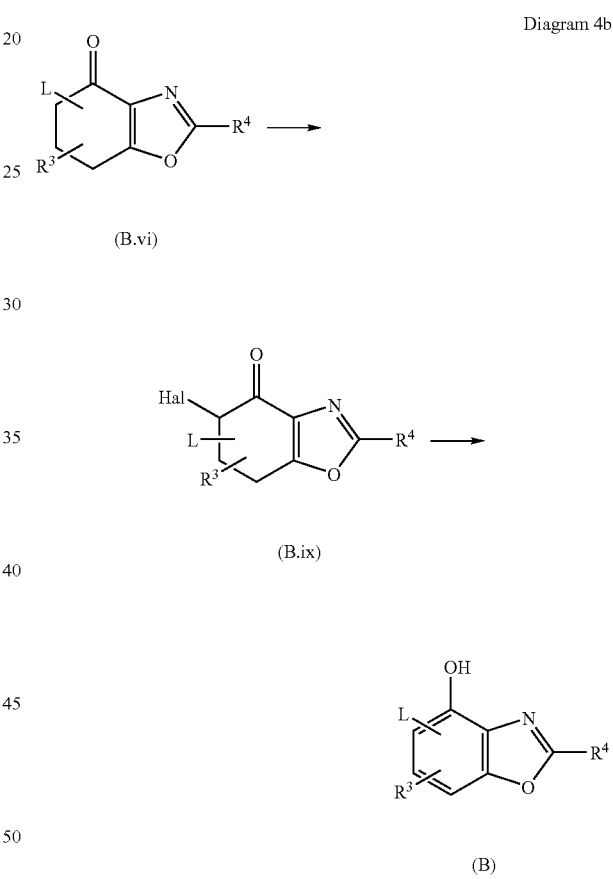

Diagram 4b

If they are not commercially available and in the particular case where Q represents hydroxyl, Q' a hydrogen atom and W an oxygen atom, the compounds of general formula (B) can be obtained by aromatization of the oxazolocyclohexanones of general formula (B.vi). Such aromatization can be carried out in two stages as shown in Diagram 4b, firstly a halogenation in position α of the carbonyl (which If they are not commercially available and in the particular case where $R^4$ represents a —H$_2$—NR$^{21}$R$^{22}$ radical, the compounds of general formula (B) can be obtained, Diagram 5, from the compounds of general formula (B.iii) in which $R^4$ represents the methyl radical, which is subjected firstly to a radical bromination reaction using N-bromosuccinimide in the presence of an initiator such as 2,2'-azobis (2-methylpropionitrile) or dibenzoyl peroxide in an aprotic solvent such as carbon tetrachloride (CCl$_4$) at a temperature preferably comprised between ambient temperature (i.e. approximately 25° C.) and 80° C. and under irradiation by a UV lamp (Mylari et al., *J. Med. Chem.* (1991), 34, 108-122), followed by substitution of the intermediate of general formula (B.iv) by amines of formula $HNR^{21}R^{22}$ with $R^{21}$ and $R^{22}$ being as defined above.

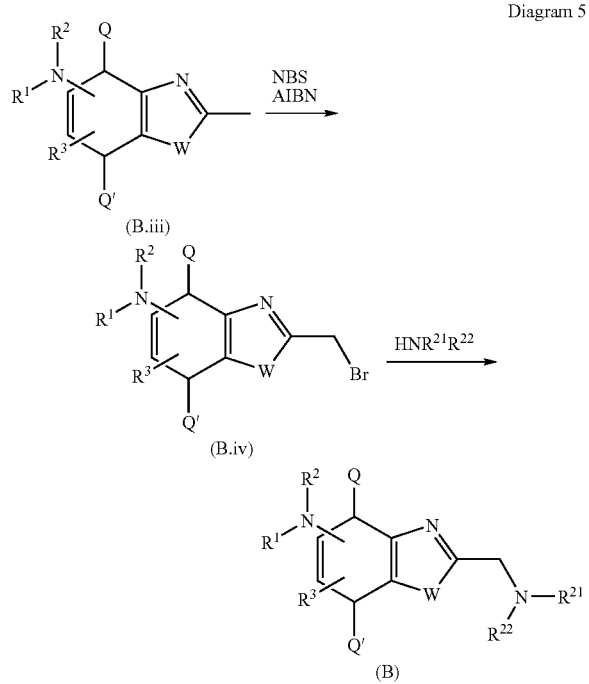

Diagram 5

Alternatively, the compounds of general formula (B) which are not commercially available in which $R^4$ represents a $—CH_2—NR^{21}R^{22}$ radical can be obtained according to the method represented in Diagram 4 above, starting from the compounds of general formula (B.i) in which $R^4$ represents a $—CH_2—NR^{21}R^{22}$ radical, these being themselves obtained from the compounds of general formula (B.i) in which $R^4$ represents a $CH_2—Br$ radical by substitution with amines of formula $HNR^{21}R^{22}$ with $R^{21}$ and $R^{22}$ as defined above. The compounds of general formula (B.i) in which $R^4$ represents a $CH_2—Br$ radical can be obtained, as described above, from the compounds of general formula (B.i) in which $R^4$ represents the methyl radical, which is subjected to a radical bromination reaction.

If they are not commercially available and in the particular case where $R^4$ represents a $—CH_2—CO—NR^{19}R^{20}$ radical, the compounds of general formula (B) can be obtained from the compounds of general formula (B) in which $R^4$ represents the $—CH_2—COOH$ radical, by standard methods of peptide synthesis (M. Bodansky, The Practice of Peptide Synthesis, 145 (Springer-Verlag, 1984)), for example in tetrahydrofuran, dichloromethane or dimethylformamide in the presence of a coupling reagent such as cyclohexylcarbodiimide (DCC), 1,1'-carbonyldiimidazole (CDI) (*J. Med. Chem.* (1992), 35(23), 4464-4472) or benzotriazol-1-yl-oxy-tris-pyrrolidino-phosphonium hexafluorophosphate (PyBOP) (Coste et al., *Tetrahedron Lett.* (1990), 31, 205).

The compounds of general formula (B) in which $R^4$ represents $—CH_2—COOH$ can be obtained from the compounds of general formula (B) in which $R^4$ represents the $—CH_2—COOR^{18}$ radical in which $R^{18}$ represents an alkyl radical by hydrolysis of the ester function under conditions known to a person skilled in the art.

The compounds of general formula (B) in which W represents S, Q and Q' each represent a methoxy radical and L represents a halogen atom or a hydrogen atom can be obtained, Diagram 6, by treatment of the N-(2,5-dimethoxyphenyl)thioamides of general formula (B.x) by an aqueous solution of potassium ferricyanide in sodic medium at ambient temperature (Lyon et al., *J. Chem. Soc., Perkin Trans.* 1 (1999), 437-442). The compounds of general formula (B.x) can themselves be obtained by starting from the corresponding acylated 2,5-dimethoxyanilines of general formula (B.xii), for example by the action of an acid chloride of general formula $R^4COCl$ or a carboxylic acid of general formula $R^4COOH$ activated according to methods known to a person skilled in the art, in order to produce the N-(2,5-dimethoxyphenyl)amides of general formula (B.xi) themselves converted to the thioamides of general formula (B.x) by the action of Lawesson's reagent in toluene at reflux.

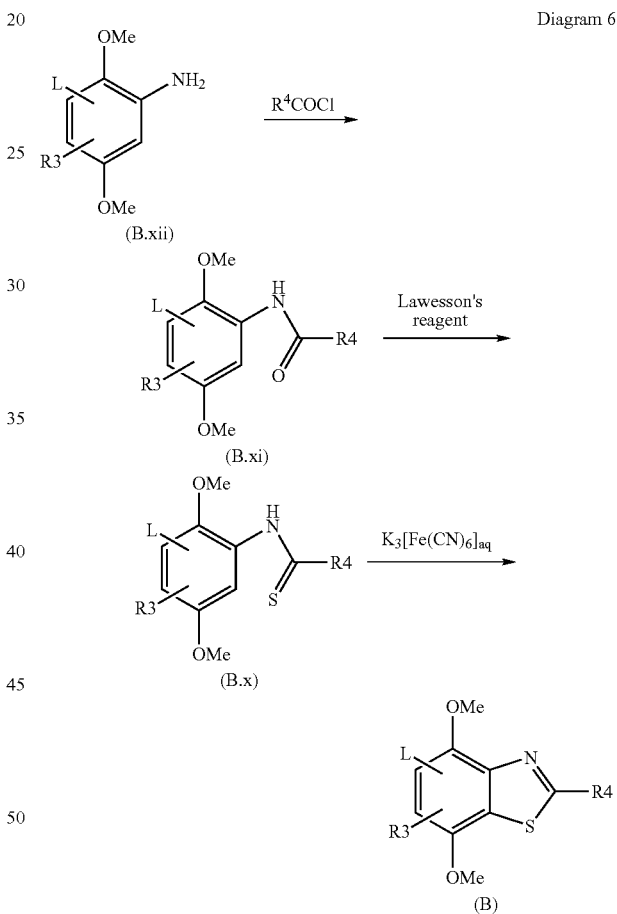

Diagram 6

In the other cases, the compounds of general formula (B) can be obtained, Diagram 6, from the compounds of general formula (C) in which L, $R^3$ and W are as defined above and Q or Q' represents the $NO_2$ radical by condensation with the orthoester of general formula $R^4C(OR)_3$ in which R is an alkyl radical, for example in the presence of a catalytic quantity of an acid such as, for example, paratoluenesulphonic acid, at a temperature comprised between ambient temperature and 200° C. and preferably at approximately 110° C. (Jenkins et al., *J. Org. Chem.* (1961), 26, 274) or also in a protic solvent such as ethanol at a temperature comprised between ambient temperature (i.e. approximately 25°

C.) and 80° C. and preferably at approximately 60° C. (Scott et al., *Synth. Commun.* (1989), 19, 2921). A certain number of orthoesters are known industrial products available from the usual suppliers. The preparation of orthoesters by treating various nitrile compounds with hydrochloric gas in an alcohol is known to a person skilled in the art.

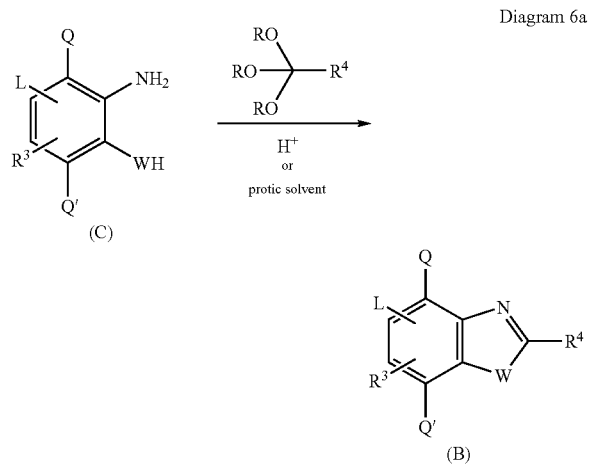

Diagram 6a

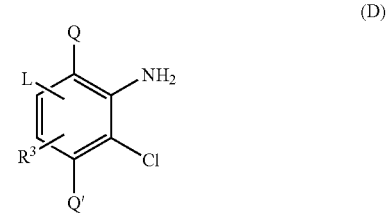

The compounds of general formula (B) in which L, $R^3$, $R^4$ and W are as defined above and Q or Q' represents the $NO_2$ radical can also be obtained from the compounds of general formula (C) in which L, $R^3$, $R^4$ and W are as defined above and one of Q and Q' represents the $NO_2$ radical whilst the other represents a hydrogen atom by condensation of the latter with an acid chloride of formula $R^4$—COCl under an inert atmosphere and in a polar and slightly basic solvent such as N-methyl-2-pyrrolidinone (Brembilla et al., *Synth. Commun* (1990), 20, 3379-3384) or by condensation of the latter with a carboxylic acid of general formula $R^4$—COOH in the presence of polyphosphoric acid at high temperature (Ying-Hung So et al., *Synth. Commun*. (1998), 28, 4123-4135) or in the presence of boric acid in a solvent such as xylene under reflux (M. Terashima, *Synthesis* (1982), 6, 484-485).

The compounds of general formula (B) in which L, $R^3$, $R^4$ and W are as defined above and Q or Q' represents the $NO_2$ radical can also be obtained from the compounds of general formula (C) in which L, $R^3$, $R^4$ and W are as defined above and one of Q and Q' represents the $NO_2$ radical whilst the other represents a hydrogen atom by condensation with an aldehyde of general formula $R^4$—CHO then treating the Schiff base obtained with an oxidizing agent such as [bis(acetoxy)iodo]benzene, ferric chloride or dimethylsulphoxide (Racane et al., *Monatsh. Chem.* (1995), 126(12), 1375-1381) or by dehydrating with glacial acetic acid at a temperature comprised between ambient temperature (i.e. approximately 25° C.) and 100° C. (Katritzky and Fan, *J. Heterocyclic Chem.* (1988), 25, 901-906).

The compounds of general formula (B) in which L, $R^3$, $R^4$ and W are as defined above and one of Q and Q' represents the $NO_2$ radical whilst the other represents a hydrogen atom can also be obtained from the compounds of general formula (C) by condensation with a nitrile of general formula $R^4$—CN in a mixture of solvents of methanol/glacial acetic acid type at a temperature comprised between ambient temperature (i.e. approximately 25° C.) and 100° C. (Nawwar and Shafik, *Collect. Czech Chem. Commun.* (1995), 60(12), 2200-2208).

Preparation of the Intermediates of General Formula (C)

Certain compounds of general formula (C) in which L, $R^3$, Q, Q' and W are as defined above are known industrial products available from the usual suppliers.

Certain compounds of general formula (C) in which one of Q and Q' represents the $NO_2$ radical whilst the other represents a hydrogen atom can be obtained from the compounds of general formula (D)

(D)

in which L, $R^3$, Q and Q' are as defined above by reaction, in the case where W represents S, with hydrated sodium sulphide at a temperature comprised between ambient temperature (i.e. approximately 25° C.) and 100° C. (Katritzky and Fan, *J. Heterocyclic Chem.* (1988), 25, 901-906).

Finally, in the particular case where W represents O, the compounds of general formula (C) are known industrial products available from the usual suppliers or can be synthesized from such products according to current methods known to a person skilled in the art.

Separation of Mixtures of Regioisomers

In certain cases, it can happen that the compounds of general formula (I) prepared according to the abovementioned methods are obtained in the form of mixtures of regioisomers.

In such situations, the mixture can be separated using standard techniques of liquid chromatography on a column or preparative thin layer chromatography (using a support such as silica or also a gel such as a cross-linked polydextran gel forming a three-dimensional network such as a Sephadex® LH-20 type gel). A person skilled in the art will choose the eluent most suitable for the separation of the mixture; such eluent can be for example a ternary isopropanol/ethyl acetate/water mixture 1/1/1.

As regards the temperatures referred to in the present text, the term <<approximately XX° C.>> indicates that the temperature in question corresponds to a range of more or less 10° C. either side of the temperature XX° C., and preferably to a range of more or less 5° C. either side of the temperature XX° C.

Unless they are defined in another manner, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

Method Used for Measuring the Retention Time (r.t.) and the Molecular Peak (MH+)

The compounds are characterised by their retention time (r.t.), expressed in minutes, determined by liquid chromatography (LC), and their molecular peak (MH+) determined by mass spectrometry (MS), a single quadripole mass spectrometer (Micromass, Platform model) equipped with an electrospray source is used with a resolution of 0.8 Da at 50% valley.

For Examples 1 to 122 below, the elution conditions corresponding to the results indicated are the following: transition of an acetonitrile-water-trifluoroacetic acid mixture 50-950-0.2 (A) to an acetonitrile-water mixture 950-50 (B) via a linear gradient over a period of 8.5 minutes, then elution with the pure mixture B for 10.5 minutes.

Example 1

2-methyl-5-{[2-(4-morpholinyl)ethyl]amino}-1,3-benzothiazole-4,7-dione 51.2 µl (0.39 mmol; 3 equivalents) of 4-(2-aminoethyl)morpholine is added to 27 mg (0.129 mmol) of 5-methoxy-2-methyl-4,7-dioxobenzothiazole in solution in 2 ml of anhydrous ethanol. The reaction mixture is stirred under reflux for 18 hours then the solvent is evaporated off under reduced pressure. The residue is purified on a silica column (eluent: 5% methanol in dichloromethane). The expected compound is obtained in the form of a red powder.

NMR $^1$H (DMSO d6, 400 MHz, δ): 7.45 (t, 1H, NH); 5.49 (s, 1H, CH); 3.58-3.55 (m, 4H, 2 CH$_2$); 3.26 (t, 2H, CH$_2$); 2.75 (s, 3H, CH$_3$); 2.54 (t, 2H, CH$_2$); 2.42-2.40 (m, 4H, 2 CH$_2$).

MS-LC: MH+=308.25; r.t.=6.89 min.

Example 2

5-{[2-(dimethylamino)ethyl]amino}-2-methyl-1,3-benzothiazole-4,7-dione hydrochloride 2.1) 5-{[2-(dimethylamino)ethyl]amino}-2-methyl-1,3-benzothiazole-4,7-dione This compound is obtained in a similar manner to that used for the compound of Example 1.

NMR $^1$H (DMSO d6, 400 MHz, δ): 7.34 (t, 1H, NH); 5.48 (s, 1H, CH); 3.24-3.20 (m, H, CH$_2$); 2.77 (s, 3H, CH$_3$); 2.47 (m, 2H, CH$_2$); 2.18 (s, 6H, 2 CH$_3$).

MS-LC: MH+=266.27; r.t.=6.83 min.

2.2) 5-{[2-(dimethylamino)ethyl]amino}-2-methyl-1,3-benzothiazole-4,7-dione hydrochloride 0.166 g of intermediate 2.1 is dissolved in 1.88 ml (1.88 mmol; 3 eq.) of a molar solution of hydrochloric acid in ether and the reaction mixture is stirred for 3 hours at ambient temperature. The resulting precipitate is collected by filtration, followed by washing with ethyl ether and drying under reduced pressure in order to produce a dark red solid. Melting point: 138-140° C.

NMR $^1$H (DMSO d6, 400 MHz, δ): 10.00 (s, 1H, NH$^+$); 7.78 (t, 1H, NH); 5.68 (s, 1H, CH); 3.59-3.55 (m, 2H, CH$_2$); 3.32-3.27 (m, 2H, CH$_2$); 2.85-2.80 (s, 6H, 2 CH$_3$); 2.76 (s, 3H, CH$_3$).

MS-LC: MH+=266.12; r.t.=6.92 min.

The compounds of Examples 3 to 14 are obtained in a similar manner to that used for Example 1.

Example 3

5-{[6-(dimethylamino)hexyl]amino}-2-methyl-1,3-benzothiazole-4,7-dione

MS-LC: MH+=322.33; r.t.=7.36 min.

Example 4

5-{[3-(dimethylamino)-2,2-dimethylpropyl]amino}-2-methyl-1,3-benzothiazole-4,7-dione NMR $^1$H (DMSO d6, 400 MHz, δ): 8.62 (t, 1H, NH); 5.45 (s, 1H, CH); 3.07-3.06 (m, 2H, CH$_2$); 2.74 (s, 3H, CH$_3$); 2.29-2.30 (m, 2H, CH$_2$); 2.27 (s, 6H, 2CH$_3$); 0.93 (s, 6H, 2 CH$_3$).

LC-MS: MH+=308.32; r.t.=7.16 min.

Example 5

2-methyl-5-{[3-(4-methyl-1-piperazinyl)propyl]amino}-1,3-benzothiazole-4,7-dione NMR $^1$H (DMSO d6, 400 MHz, δ): 8.14 (t, 1H, NH); 5.46 (s, 1H, CH); 3.25-3.26 (m, 2H, CH$_2$); 3.21-3.19 (m, 2H, CH$_2$); 2.74 (s, 3H, CH$_3$); 2.49-2.48 (m, 2H, CH$_2$); 2.37-2.32 (m, 6H, 3CH$_2$); 2.16 (s, 3H, CH$_3$); 1.72 (t, 2H, CH$_2$).

MS-LC: MH+=335.34; r.t.=6.87 min.

Example 6

5-[(1-ethylhexyl)amino]-2-methyl-1,3-benzothiazole-4,7-dione

MS-LC: MH+=307.32; r.t.=11.45 min.

Example 7

5-[(1-adamantylmethyl)amino]-2-methyl-1,3-benzothiazole-4,7-dione

MS-LC: MH+=343.31; r.t.=11.73 min.

Example 8

2-methyl-5-[(2-thienylmethyl)amino]-1,3-benzothiazole-4,7-dione

MS-LC: MH+=291.16; r.t.=9.24 min.

Example 9

5-[(3-chlorobenzyl)amino]-2-methyl-1,3-benzothiazole-4,7-dione

MS-LC: MH+=319.24; r.t.=9.95 min.

Example 10

2-methyl-5-[(4-pyridinylmethyl)amino]-1,3-benzothiazole-4,7-dione

MS-LC: MH+=286.13; r.t.=6.97 min.

Example 11

2-methyl-5-(propylamino)-1,3-benzothiazole-4,7-dione

MS-LC: MH+=237.16; r.t.=8.74 min.

Example 12

5-{[3-(1H-imidazol-1-yl)propyl]amino}-2-methyl-1,3-benzothiazole-4,7-dione

MS-LC: MH+=303.17; r.t.=7.07 min.

Example 13

4-{2-[(2-methyl-4,7-dioxo-4,7-dihydro-1,3-benzothiazol-5-yl)amino]ethyl}benzenesulphonamide MS-LC: MH+=378.10; r.t.=8.31 min.

Example 14

5-(4-benzyl-1-piperazinyl)-2-methyl-1,3-benzothiazole-4,7-dione

MS-LC: MR+=354.19; r.t.=7.53 min.

Example 15

5-anilino-2-ethyl-4,7-dihydrobenzo[d][1,3]oxazole-4,7-dione

15.1) 2-ethyl-4-nitro-1,3-benzoxazole

A mixture of 2-amino-3-nitrophenol (1 eq.), triethyl orthopropionate (2 eq.) and p-toluene sulphonic acid (in a catalytic quantity) is stirred at 110° C. until disappearance of the aminophenol is verified by thin layer chromatography (2 hours). After cooling down, the reaction mixture is taken up in toluene followed by evaporating under vacuum then treating with isopropanol. The resulting precipitate is collected by filtration, followed by washing with isopropanol and isopentane, then drying under reduced pressure in order to produce a violet-brown solid.

NMR $^1$H (DMSO d6, 400 MHz, δ): 8.15 (dd, 2H); 7.58 (t, 1H); 3.06 (q, 2H); 1.38 (t, 3H).

MS-LC: MH+=193.02; r.t.=9.23 min.

15.2) 2-ethyl-1,3-benzoxazol-4-amine 2-ethyl-4-nitro-1,3-benzoxazole is hydrogenated under a pressure of 8 bars in the presence of 10% palladium on carbon (0.01 eq.) using methanol as a solvent. The catalyst is separated by filtration and the methanol is eliminated under reduced pressure. The residue is taken up in ethyl ether in order to produce a pale violet solid which is collected by filtration and dried. Melting point: 46° C.

NMR $^1$H (DMSO d6, 400 MHz, δ): 6.97 (t, 1H); 6.72 (d, 1H); 6.47, d, 1H); 5.45 (s, 2H); 2.87 (q, 2H); 1.32 (t, 3H).

MS-LC: MH+=162.99; r.t.=8.72 min.

15.3) 2-ethyl-1,3-benzoxazole-4,7-dione

A solution of [bis(trifluoroacetoxy)iodo]benzene (2.2 eq.) in a mixture of acetonitrile and water (80/20) is added dropwise to a solution of 2-ethyl-1,3-benzoxazol-4-amine (1 eq.) in the same acetonitrile/water mixture maintained at –5° C. The reaction medium is then diluted with water followed by extracting with dichloromethane. The resulting organic phase is washed with water, followed by drying over sodium sulphate and concentrating in order to produce a brown paste. Purification by medium pressure chromatography on silica gel produces, after taking up in diisopropyl ether, a yellow crystalline solid. Melting point: 99° C.

NMR $^1$H (CDCl$_3$, 400 MHz, δ): 6.75 (dd, 2H); 2.99 (q, 2H); 1.45 (t, 3H). MS-LC: MH+=177.83; r.t.=8.29 min.

15.4) 5-anilino-2-ethyl-1,3-benzoxazole-4,7-dione

A mixture of 2-ethyl-1,3-benzoxazole-4,7-dione (1 eq) and aniline (1.1 eq.) in ethanol is kept under stirring for 1 hour. The reaction medium turns to dark violet. After concentration, the residue is purified by medium pressure chromatography on silica in order to produce a violet-coloured powder. Melting point: 200° C.

NMR $^1$H (DMSO d6, 400 MHz, δ): 9.38 (s, 1H); 7.44 (t, 2H); 7.36 (d, 2H); 7.22 (t, 1H); 5.69 (s; 1H); 2.94 (q, 2H); 1.29 (t, 3H).

MS-LC: MH+=269.11; r.t.=9.76 min.

Example 16

5-anilino-6-chloro-2-ethyl-1,3-benzoxazole-4,7-dione

A solution of 5-anilino-2-ethyl-1,3-benzoxazole-4,7-dione (1 eq.) in acetic acid is treated with N-chlorosuccinimide (1.1 eq.) at ambient temperature. The reaction medium is maintained under stirring for 2 hours before being concentrated, followed by taking up in ethanol and concentrating again. The residue is purified by medium pressure chromatography on silica in order to produce a violet-coloured powder.

Melting point: 159° C.

NMR $^1$H (CDCl$_3$, 400 MHz, δ): 9.39 (s, 1H); 7.30 (t, 2H); 7.11 (m, 3H); 2.96 (q, 2H); 1.30 (t, 3H).

MS-LC: MH+=303.01; r.t.=10.28 min.

Example 17

2-ethyl-5-[(4-fluorophenyl)amino]-1,3-benzoxazole-4,7-dione

The experimental protocol used is identical to that described for Example 15, 4-fluoroaniline acid replacing aniline in the fourth and last stage. Melting point: 232° C.

NMR $^1$H (CDCl$_3$, 400 MHz, δ): 9.38 (s, 1H); 7.37 (t, 2H); 7.26 (t, 2H); 5.57 (s, 1H); 2.93 (q, 2H); 1.30 (t, 3H).

MS-LC: MH+=287.09; r.t.=9.88 min.

The compounds of Examples 18 to 31 are obtained in a similar manner to that described for Example 1.

Example 18

5-[(2-methoxyethyl)amino]-2-methyl-1,3-benzothiazole-4,7-dione

MS-LC: MH+=253.20; r.t.=8.00 min.

Example 19

2-methyl-5-[(2-pyrrolidin-1-ylethyl)amino]-1,3-benzothiazole-4,7-dione

NMR $^1$H (DMSO d6, 400 MHz, δ): 7.45 (m, 1H, NH); 5.47 (s, 1H, CH); 3.28-3.23 (m, 2H, CH$_2$); 2.75 (s, 3H, CH$_3$); 2.66-2.63 (m, 2H, CH$_2$); 2.48-2.49 (m, 4H, 2CH$_2$); 1.68-1.67 (m, 4H, 2CH$_2$).
MS-LC: MH+=292.13; r.t.=7.11 min.

Example 20

2-methyl-5-[(2-piperidin-1-ylethyl)amino]-1,3-benzothiazole-4,7-dione

MS-LC: MH+=306.24; r.t.=7.22 nmin.

Example 21

5-{[2-(diisopropylamino)ethyl]amino}-2-methyl-1,3-benzothiazole-4,7-dione

MS-LC: MH+=322.33; r.t.=7.37 min.

Example 22

5-[(1-benzylpyrrolidin-3-yl)amino]-2-methyl-1,3-benzothiazole-4,7-dione

MS-LC: MH+=354.28; r.t.=7.70 min.

Example 23

5-{[3-(dimethylamino)propyl]amino}-2-methyl-1,3-benzothiazole-4,7-dione

MS-LC: MH+=280.15; r.t.=7.01 min.

Example 24

2-methyl-5-{[2-(1-methylpyrrolidin-2-yl)ethyl]amino}-1,3-benzothiazole-4,7-dione MS-LC: MH+=306.30; r.t.=7.23 min.

Example 25

2-methyl-5-{[3-(2-methylpiperidin-1-yl)propyl]amino}-1,3-benzothiazole-4,7-dione MS-LC: MH+=334.29; r.t.=7.38 min.

Example 26

5-{[4-(dimethylamino)butyl]amino}-2-methyl-1,3-benzothiazole-4,7-dione

MS-LC: MH+=294.16; r.t.=7.11 min.

Example 27

5-{[5-(dimethylamino)pentyl]amino}-2-methyl-1,3-benzothiazole-4,7-dione

MS-LC: MH+=308.16; r.t.=7.22 min.

Example 28

5-(2,3-dihydro-1H-inden-1-ylamino)-2-methyl-1,3-benzothiazole-4,7-dione

MS-LC: MH+=311.26; r.t.=10.16 min.

Example 29

5-{benzyl[2-(dimethylamino)ethyl]amino}-2-methyl-1,3-benzothiazole-4,7-dione

NMR $^1$H (DMSO d6, 400 MHz, δ): 7.37-7.28 (m, 5H, H arom.); 5.61 (s, 1H, CH); 4.57 (s, 2H, CH$_2$); 3.71-3.68 (m, 2H, CH$_2$); 2.75 (s, 3H, CH$_3$); 2.39-2.37 (m, 2H, CH$_2$); 1.95 (s, 6H, 2 CH$_3$).
MS-LC: MH+=365.10; r.t.=7.70 min.

Example 30 tert-butyl methyl{3-[(2-methyl-4,7-dioxo-4,7-dihydro-1,3-benzothiazol-5-yl)amino]propyl}carbamate NMR $^1$H (DMSO d6, 400 MHz, δ): 7.75 (m, 1H, NH); 5.45 (s, 1H, CH); 3.22-3.18 (m, 2H, CH$_2$); 3.15-3.12 (m, 2H, CH$_2$); 2.76 (m, 3H, CH$_3$); 2.75 (s, 3H, CH$_3$); 1.78-1.75 (m, 2H, CH$_2$); 1.35 (m, 9H, 3 CH$_3$).
MS-LC: MH+=366.15; r.t.=9.61 min.

Example 31 tert-butyl 3-[(2-methyl-4,7-dioxo-4,7-dihydro-1,3-benzothiazol-5-yl)amino]propylcarbamate MS-LC: MH+=352.22; r.t.=9.09 min.

Example 32

2-methyl-5-{[3-(methylamino)propyl]amino}-1,3-benzothiazole-4,7-dione hydrochloride 25 mg (68.5 μmol) of the compound of Example 30 is suspended in 10 ml of diethylether. 4 ml of a molar solution of hydrochloric acid in ether is added, then the reaction mixture is stirred at ambient temperature for 2 hours. The resulting precipitate is collected by filtration, followed by washing with ether then drying under reduced pressure in order to produce a brownish-red solid.
NMR $^1$H (DMSO d6, 400 MHz, δ): 8.61 (m, 2H, NH$_2^+$); 7.84-7.81 (m, 1H, NH); 5.55 (s, 1H, CH); 3.29-3.24 (m, 2H, CH$_2$); 2.91-2.88 (m, 2H, CH$_2$); 2.75 (s, 3H, CH$_3$); 2.53-2.52 (m, 3H, CH$_3$); 1.89-1.86 (m, 2H, CH$_2$).
MS-LC: MH+=266.06; r.t.=7.04 min.

Example 33

5-[(3-aminopropyl)amino]-2-methyl-1,3-benzothiazole-4,7-dione 20 mg (57 μmol) of the compound of Example 30 is suspended in 10 ml of diethylether. 840 μl of a molar solution of hydrochloric acid in ether is added then the reaction mixture is stirred at ambient temperature for 2 hours. The resulting precipitate is collected by filtration, followed by washing with ether then drying under reduced pressure in order to produce a brownish-red solid.

NMR $^1$H (DMSO d6, 400 MHz, δ): 7.84-7.78 (m, 3H, NH, NH$_2$); 5.56 (s, 1H, CH); 3.28-3.23 (m, 2H, CH$_2$); 2.86-2.81 (m, 2H, CH$_2$); 2.75 (s, 3H, CH$_3$); 1.85-1.82 (m, 2H, CH$_2$).

MS-LC: MH+=280.15; r.t.=7.01 min.

Example 34

6-chloro-5-{[2-(dimethylamino)ethyl]amino}-2-methyl-1,3-benzothiazole-4,7-dione 58.6 mg (0.22 mmol) of intermediate 2.1 is placed in solution in 5 ml of acetic acid. 32.5 mg (0.24 mmol; 1.1 eq.) of N-chlorosuccinimide is added and the reaction mixture is stirred for 3 hours at ambient temperature. After concentration, the residue is purified by chromatography on a silica column (eluent: dichloromethane/methanol 90/10) and the expected product is obtained, after taking up in ethyl ether, in the form of a violet-coloured powder.

NMR $^1$H (DMSO d6, 400 MHz, δ): 7.31 (m, 1H, NH); 3.79-3.74 (m, 2H, CH$_2$); 2.75 (s, 3H, CH$_3$); 2.47-2.44 (m, 2H, CH$_2$); 2.13 (s, 6H, 2 CH$_3$).

MS-LC: MH+=300.09; r.t.=7.17 min.

Example 35

6-bromo-5-{[2-(dimethylamino)ethyl]amino}-2-methyl-1,3-benzothiazole-4,7-dione 102 mg (0.38 mmol) of intermediate 2.1 is placed in solution in 10 ml of acetic acid. 77.3 mg (0.43 mmol; 1.1 eq.) of N-bromosuccinimide is added and the reaction mixture is stirred for 3 hours at ambient temperature. After concentration under reduced pressure, the residue is purified by chromatography on a silica column (eluent: dichloromethane/methanol 90/10) and the expected product is obtained, after taking up in ethyl ether, in the form of a violet-coloured powder.

NMR $^1$H (DMSO d6, 400 MHz, δ): 7.24 (m, 1H, NH); 3.78-3.74 (m, 2H, CH$_2$); 2.75 (s, 3H, CH$_3$); 2.45-2.42 (m, 2H, CH$_2$); 2.11 (s, 6H, 2 CH$_3$).

MS-LC: MH+=343.97; r.t.=7.22 min.

Example 36

6-(butylthio)-5-{[2-(dimethylamino)ethyl]amino}-2-methyl-1,3-benzothiazole-4,7-dione 20 µl (0.115 mmol; 1.2 eq.) of diisopropylethylamine and 16 µl (0.154 mmol; 1.6 eq.) of butanethiol are added to 33 mg (96 µmol) of the compound of Example 35 in solution in 4 ml of anhydrous ethanol. The reaction mixture is maintained under stirring for 24 hours at 60° C., then after concentration under reduced pressure, the residue is purified by chromatography on a silica column (eluent: dichloromethane/methanol 95/5) and the expected product is obtained, after taking up in ethyl ether, in the form of a violet-coloured powder.

NMR $^1$H (DMSO d6, 400 MHz, δ): 7.56 (m, 1H, NH); 3.84-3.83 (m, 2H, CH$_2$); 2.75 (s, 3H, CH$_3$); 2.64-2.60 (t, 2H, CH$_2$); 2.45-2.42 (m, 2H, CH$_2$); 2.20 (s, 6H, 2 CH$_3$); 1.44-1.46 (m, 2H, CH$_2$); 1.37-1.33 (m, 2H, CH$_2$); 0.85-0.82 (t, 3H, CH$_3$).

Example 37

5-{[2-(dimethylamino)ethyl]amino}-2-(morpholin-4-ylmethyl)-1,3-benzothiazole-4,7-dione 37.1) 2-(bromomethyl)-5-methoxy-1,3-benzothiazole 2.58 g (14.5 mmol; 1.3 eq.) of N-bromosuccinimide and a spatula tip's worth of aza-bis-isobutyronitrile are added to 2 g (11.16 mmol) of 2-methyl-5-methoxy-1,3-benzothiazole in solution in 25 ml of anhydrous carbon tetrachloride. The reaction mixture is heated under reflux and under irradiation for 6 hours, with a spatula tip's worth of aza-bis-isobutyronitrile added every 2 hours. After returning to ambient temperature, the insoluble part formed is filtered, the solvent is evaporated off under reduced pressure and the residue is purified by chromatography on a silica column (eluent: ethyl acetate/heptane 1/4). The expected product is obtained in the form of a white solid.

NMR $^1$H (DMSO d6, 400 MHz, δ): 7.98-7.96 (m, 1H, H arom.); 7.54-7.53 (m, 1H, H arom.); 7.13-7.10 (m, 1H, H arom.); 5.09 (s, 2H, CH$_2$); 3.84 (s, 3H, CH$_3$).

MS-LC: MH+=258.38; r.t.=10.36 min.

37.2) 5-methoxy-2-(morpholin-4-ylmethyl)-1,3-benzothiazole

678 µl of diisopropylethylamine (3.9 mmol; 2 eq.) is added to 0.5 g of intermediate 37.1 in solution in 20 ml of anhydrous toluene. 187 µl (2.14 mmol; 1.1 eq.) of morpholine and a spatula tip's worth of sodium iodide are added to the previous solution, then the reaction mixture is maintained under stirring at 80° C. for 3 hours. After cooling down, the reaction medium is washed with water (3 times 20 ml), then the organic phase is dried over magnesium sulphate and concentrated. Purification by chromatography on a silica column (eluent: ethyl acetate/heptane 1/1) allows the expected product to be obtained in the form of a beige solid.

NMR $^1$H (DMSO d6, 400 MHz, δ): 7.91-7.89 (m, 1H, H arom.); 7.47-7.46 (m, 1H, H arom.); 7.05-7.02 (m, 1H, H arom.); 3.92 (s, 2H, CH$_2$); 3.82 (s, 3H, CH$_3$); 3.63-3.61 (m, 4H, 2CH$_2$); 2.56-2.53 (m, 4H, 2CH$_2$).

MS-LC: MH+=265.10; r.t.=7.55 min.

37.3) 5-methoxy-2-(morpholin-4-ylmethyl)-4-nitro-1,3-benzothiazole:

84 mg (0.83 mmol; 1.2 eq.) of potassium nitrate is added by portions to a solution at 0° C. of 0.2 g (0.76 mmol) of intermediate 37.2 in 0.7 ml of concentrated sulphuric acid. After returning to ambient temperature, the reaction mixture is stirred for 18 hours, neutralized by adding a 10M aqueous solution of soda followed by extracting with 3 times 50 ml dichloromethane. The resulting organic phase is dried over magnesium sulphate followed by concentrating, then purifying by chromatography on a silica column (eluent: ethyl acetate/heptane 1/1). The expected product is obtained in the form of a yellow oil.

NMR $^1$H (DMSO d6, 400 MHz, δ): 8.26-8.24 (m, 1H, H arom.); 7.48-7.46 (m, 1H, H arom.); 3.98-3.96 (2s, 5H, CH$_3$, CH$_2$); 3.63-3.61 (m, 4H, 2CH$_2$); 2.59-2.56 (m, 4H, 2 CH$_2$).

MS-LC: MH+=310.11; r.t.=8.03 min.

37.4) 5-methoxy-2-(morpholin-4-ylmethyl)-1,3-benzothiazol-4-amine:

0.93 g (4.11 mmol; 5 eq.) of tin chloride is added to a solution of 0.254 g (0.822 mmol) of intermediate 37.3 in 7 ml of concentrated hydrochloric acid. The reaction mixture is maintained under stirring for 3 hours at 70° C. After returning to ambient temperature, the medium is diluted by adding 20 ml of ethyl acetate, followed by neutralizing with a saturated solution of $NaHCO_3$ and finally washing with 3 times 20 ml of water. The organic phases are combined, followed by drying over magnesium sulphate and concentrating in order to provide the expected product in the form of a beige powder.

NMR $^1$H (DMSO d6, 400 MHz, δ): 7.12-7.10 (m, 1H, arom H.); 7.02-7.00 (m, 1H, arom H.); 5.04 (s, 2H, $NH_2$); 3.88 (s, 2H, $CH_2$); 3.81 (s, 3H, $CH_3$); 3.63-3.60 (m, 4H, 2 $CH_2$); 2.55-2.52 (m, 4H, 2$CH_2$).

MS-LC: MH+=280.11; r.t.=7.29 min.

37.5) 5-methoxy-2-(morpholin-4-ylmethyl)-1,3-benzothiazole-4,7-dione

A solution of 84 mg (0.31 mmol; 1.8 eq.) of Fremy's salt, dissolved in 14 ml of a buffer solution (0.3M) of sodium hydrogen phosphate, is added to 0.0483 mg (0.17 mmol) of intermediate 37.4 in solution in 10 ml of acetone. The reaction mixture is stirred for 18 hours at ambient temperature, followed by extracting with 3 times 30 ml of dichloromethane, the organic phases then being washed with twice 20 ml of water. The organic phases are then combined, followed by drying over magnesium sulphate and then concentrating under reduced pressure. The residue is purified by chromatography on a silica column (eluent: ethyl acetate/heptane 1/1) and the expected product is obtained in the form of a yellow oil.

MS-LC: MH+=295.06; r.t.=7.11 min.

37.6) 5-{[2-(dimethylamino)ethyl]amino}-2-(morpholin-4-ylmethyl)-1,3-benzothiazole-4,7-dione The experimental protocol used is identical to that described for Example 1, intermediate 37.5 replacing 5-methoxy-2-methyl-4,7-dioxobenzothiazole.

MS-LC: MH+=351.38; r.t.=3.07 min.

Example 38

5-{[2-(dimethylamino)ethyl]amino}-2-[(4-phenylpiperazin-1-yl)methyl]-1,3-benzothiazole-4,7-dione The experimental protocol used is identical to that described for Example 37, N-phenylpiperazine replacing morpholine in the second stage.

MS-LC: MH+=426.18; r.t.=7.39 min.

Example 39

5-{[2-(dimethylamino)ethyl]amino}-2-(piperidin-1-ylmethyl)-1,3-benzothiazole-4,7-dione The experimental protocol used is identical to that described for Example 37, piperidine replacing morpholine in the second stage.

MS-LC: MH+=349.13; r.t.=2.82 min.

The compounds of Examples 40 to 52 are obtained in a similar manner to that described for Example 15, suitable primary or secondary amines replacing aniline in the fourth and last stage.

Example 40

5-{[2-(dimethylamino)ethyl]amino}-2-ethyl-1,3-benzoxazole-4,7-dione or 6-{[2-(dimethylamino)ethyl]amino}-2-ethyl-1,3-benzoxazole-4,7-dione Melting point: 123° C.
NMR $^1$H (DMSO d6, 400 MHz, δ): 7.39 (t, 1H, NH); 5.30 (s, 1H, CH); 3.30-3.31 (m, 2H, $CH_2$); 3.24-3.20 (m, 2H, $CH_2$); 2.95-2.88 (q, 2H, $CH_2$); 2.17 (s, 6H, 2 $CH_3$); 1.30 (t, 3H, $CH_3$).
MS-LC: MH+=264.13; r.t.=7.02 min.

Example 41 tert-butyl 2-[(2-ethyl-4,7-dioxo-4,7-dihydro-1,3-benzoxazol-5-yl)(methyl)amino]ethylcarbamate or tert-butyl 2-[(2-ethyl-4,7-dioxo-4,7-dihydro-1,3-benzoxazol-6-yl)(methyl)amino]ethylcarbamate Melting point: 135° C.
NMR $^1$H (DMSO d6, 400 MHz, δ): 7.82 (t, 1H, NH); 5.36 (s, 1H, CH); 3.38-3.36 (m, 2H, $CH_2$); 3.30-3.27 (m, 2H, $CH_2$); 2.93-2.88 (q, 2H, $CH_2$); 2.79 (s, 3H, $CH_3$); 1.37-1.26 (m, 12H, 4 $CH_3$).
MS-LC: MH+=350.14; r.t.=9.72 min.

Example 42 tert-butyl 2-[(2-ethyl-4,7-dioxo-4,7-dihydro-1,3-benzoxazol-5-yl)amino]ethylcarbamate or tert-butyl 2-[(2-ethyl-4,7-dioxo-4,7-dihydro-1,3-benzoxazol-6-yl)amino]ethylcarbamate Melting point: 173° C.
NMR $^1$H (DMSO d6, 400 MHz, δ): 7.73 (t, 1H, NH); 6.97 (t, 1H, NH); 5.36 (s, 1H, CH); 3.20-3.17 (m, 2H, $CH_2$); 3.15-3.12 (m, 2H, $CH_2$); 2.93-2.88 (q, 2H, $CH_2$); 1.36 (s, 9H, 3$CH_3$); 1.28 (t, 3H, $CH_3$).
MS-LC: MH+=336.23; r.t.=9.24 min.

Example 43

5-{[3-(dimethylamino)propyl]amino}-2-ethyl-1,3-benzoxazole-4,7-dione or 6-{[3-(dimethylamino)propyl]amino}-2-ethyl-1,3-benzoxazole-4,7-dione Melting point: 101° C.
NMR $^1$H (DMSO d6, 400 MHz, δ): 8.09 (t, 1H, NH); 5.28 (s, 1H, CH); 3.21-3.16 (m, 2H, $CH_2$); 2.93-2.88 (q, 2H, $CH_2$); 2.28-2.25 (m, 2H, $CH_2$); 2.13 (s, 6H, 2 $CH_3$); 1.71-1.67 (m, 2H, $CH_2$); 1.28 (t, 3H, $CH_3$).
MS-LC: MH+=278.19; r.t.=7.09 min.

Example 44

2-ethyl-5-{[2-(1-methylpyrrolidin-2-yl)ethyl]amino}-1,3-benzoxazole-4,7-dione or 2-ethyl-6-{[2-(1-methylpyrrolidin-2-yl)ethyl]amino}-1,3-benzoxazole-4,7-dione Melting point: 121° C.
NMR $^1$H (DMSO d6, 400 MHz, δ): 8.11 (t, 1H, NH); 5.24 (s, 1H, CH); 3.19-3.17 (m, 2H, $CH_2$); 2.95-2.93 (m, 1H, CH); 2.92-2.87 (q, 2H, CH₂); 2.21 (s, 3H, CH₃); 2.16-2.05 (m, 2H, CH₂); 1.88-1.84 (m, 2H, CH₂); 1.63-1.57 (m, 4H, 2 CH₂); 1.28 (t, 3H, CH₃).
MS-LC: MH+=304.20; r.t.=7.20 min.

Example 45

5-{[4-(dimethylamino)butyl]amino}-2-ethyl-1,3-benzoxazole-4,7-dione or 6-{[4-(dimethylamino)butyl]amino}-2-ethyl-1,3-benzoxazole-4,7-dione NMR $^1$H (DMSO d6, 400 MHz, δ): 8.06 (t, 1H, NH); 5.28 (s, 1H, CH); 3.17-3.12 (m, 2H, CH₂); 2.93-2.88 (q, 2H, CH₂); 2.22-2.19 (m, 2H, CH₂); 2.11 (s, 6H, 2CH₃); 1.61-1.56 (m, 2H, CH₂); 1.46-1.42 (m, 2H, CH₂); 1.28 (t, 3H, CH₃).
MS-LC: MH+=292.20; r.t.=7.10 min.

Example 46

2-ethyl-5-[(4-pyrrolidin-1-ylbutyl)amino]-1,3-benzoxazole-4,7-dione or 2-ethyl-6-[(4-pyrrolidin-1-ylbutyl)amino]-1,3-benzoxazole-4,7-dione Melting point: 102° C.
NMR $^1$H (DMSO d6, 400 MHz, δ): 7.95 (t, 1H, NH); 5.28 (s, 1H, CH); 3.17-3.13 (m, 2H, CH₂); 2.93-2.87 (q, 2H, CH₂); 2.41-2.37 (m, 6H, 3CH₂); 1.63-1.58 (m, 2H, CH₂); 1.49-1.45 (m, 2H, CH₂); 1.28 (t, 3H, CH₃).
MS-LC: MH+=318.20; r.t.=7.30 min.

Example 47

5-{[5-(dimethylamino)pentyl]amino}-2-ethyl-1,3-benzoxazole-4,7-dione or 6-{[5-(dimethylamino)pentyl]amino}-2-ethyl-1,3-benzoxazole-4,7-dione NMR $^1$H (DMSO d6, 400 MHz, δ): 7.83 (t, 1H, NH); 5.27 (s, 1H, CH); 3.17-3.13 (m, 2H, CH₂); 2.93-2.87 (q, 2H, CH₂); 2.18-2.14 (m, 2H, CH₂); 2.09 (s, 6H, 2CH₃); 1.58-1.54 (m, 2H, CH₂); 1.41-1.38 (m, 2H, CH₂); 1.28 (t, 3H, CH₃).
MS-LC: MH+=306.20; r.t.=7.30 min.

Example 48

Mixture of 5-{[6-(dimethylamino)hexyl]amino}-2-ethyl-1,3-benzoxazole-4,7-dione and 6-{[6-(dimethylamino)hexyl]amino}-2-ethyl-1,3-benzoxazole-4,7-dione MS-LC: MH+=320.20; r.t.=7.50 min.

Example 49

Mixture of 2-ethyl-5-(4-methylpiperazin-1-yl)-1,3-benzoxazole-4,7-dione and 2-ethyl-6-(4-methylpiperazin-1-yl)-1,3-benzoxazole-4,7-dione MS-LC: MH+=276.10; r.t.=7.10 min.

Example 50

Mixture of 2-ethyl-5-[(1-ethylhexyl)amino]-1,3-benzoxazole-4,7-dione and 2-ethyl-6-[(1-ethylhexyl)amino]-1,3-benzoxazole-4,7-dione MS-LC: MH+=305.20; r.t.=11.50 min.

Example 51

Mixture of 5-azocan-1-yl-2-ethyl-1,3-benzoxazole-4,7-dione and 6-azocan-1-yl-2-ethyl-1,3-benzoxazole-4,7-dione MS-LC: MH+=289.20; r.t.=10.40 min.

Example 52

Mixture of 2-ethyl-5-morpholin-4-yl-1,3-benzoxazole-4,7-dione and 2-ethyl-6-morpholin-4-yl-1,3-benzoxazole-4,7-dione MS-LC: MH+=263.10; r.t.=8.60 min.

Example 53

6-chloro-5-{[2-(dimethylamino)ethyl]amino}-2-ethyl-1,3-benzoxazole-4,7-dione or 5-chloro-6-{[2-(dimethylamino)ethyl]amino}-2-ethyl-1,3-benzoxazole-4,7-dione The experimental protocol used is identical to that described for Example 34, the compound of Example 40 replacing intermediate 2.1. Melting point: 110° C.
NMR $^1$H (DMSO d6, 400 MHz, δ): 7.35 (t, 1H, NH); 3.78-3.74 (m, 2H, CH₂); 2.94-2.89 (q, 2H, CH₂); 2.48-2.45 (m, 2H, CH₂); 2.15 (s, 6H, 2CH₃); 1.28 (t, 3H, CH₃).
MS-LC: MH+=298.10; r.t.=7.20 min.

Example 54

6-bromo-5-{[2-(dimethylamino)ethyl]amino}-2-ethyl-1,3-benzoxazole-4,7-dione or 5-bromo-6-{[2-(dimethylamino)ethyl]amino}-2-ethyl-1,3-benzoxazole-4,7-dione The experimental protocol used is identical to that described for Example 35, the compound of Example 40 replacing intermediate 2.1.
NMR $^1$H (DMSO d6, 400 MHz, δ): 7.27 (t, 1H, NH); 3.78-3.74 (m, 2H, CH₂); 2.94-2.89 (q, 2H, CH₂); 2.46-2.43 (m, 2H, CH₂); 2.13 (s, 6H, 2 CH₃); 1.26 (t, 3H, CH₃).
MS-LC: MH+=342.00; r.t.=7.30 min.

Example 55

5-{[2-(dimethylamino)ethyl]amino}-2-ethyl-6-methyl-1,3-benzoxazole-4,7-dione 55.1) 2-diazo-5-methylcyclohexane-1,3-dione 12.25 ml (87.2 mmol; 2.2 eq.) of triethylamine and 8.57 g (35.67 mmol; 0.9 eq.) of 4-acetamidobenzenesulphonylazide are added to a solution of 5 g (39.6 mmol) of 5-methylcyclohexane-1,3-dione in 100 ml of dichloromethane. The reaction mixture is stirred for 75 minutes at ambient temperature, then cooled down to 0° C. and filtered on a silica bed. After concentration under reduced pressure, the solution is washed with 3 times 50 ml of water. The organic phases are combined, dried over sodium sulphate and concentrated. The resulting solid is taken up in ethyl ether followed by filtering and drying under reduced pressure. It is used in the following stage without other purification.

MS-LC: MH+=153.49; r.t.=7.21 min.

55.2) 2-ethyl-6-methyl-6,7-dihydro-1,3-benzoxazol-4 (5H)-one 285 mg (0.644 mmol; 0.02 eq.) of rhodium acetate is added to a solution of 4.9 g (32.2 mmol) of intermediate 55.1 in 50 ml of propionitrile. The reaction mixture is maintained under stirring under an inert argon atmosphere at 60° C. for 2 hours. The solvent is then evaporated off and the residue is purified by chromatography on a silica column (eluent: ethyl acetate/heptane 1/1). The expected product is obtained in the form of a yellow oil.

NMR $^1$H (DMSO d6, 400 MHz, δ): 3.02-2.97 (m, 1H, CH); 2.80-2.74 (q, 2H, $CH_2$); 2.68-2.61 (m, 1H, $CH_2$); 2.44-2.39 (m, 2H, $CH_2$); 2.34-2.30 (m, 1H, $CH_2$); 1.23 (t, 3H, $CH_3$); 1.08 (s, 3H, $CH_3$).

MS-LC: MH+=180.25; r.t.=8.55 min.

55.3) (4E)-2-ethyl-6-methyl-6,7-dihydro-1,3-benzoxazol-4(5H)-one oxime 647 mg (9.31 mmol; 1.2 eq.) of hydroxylamine hydrochloride and 764 mg (9.31 mmol; 1.2 eq.) of ammonium acetate are added to a solution of 1.39 g (7.76 mmol) of intermediate 55.2 in 200 ml of methanol. The reaction mixture is stirred for 90 minutes under reflux of the methanol, then the solvent is evaporated off, the residue is taken up in 50 ml of water then neutralized using a saturated solution of $NaHCO_3$. The expected product is extracted twice with 50 ml of ethyl acetate then washed twice with 30 ml of water. The organic phases are combined, dried over sodium sulphate and concentrated under reduced pressure. The desired product is obtained in the form of a dark yellow solid, used without other purification in the following stage.

MS-LC: MH+=195.09; r.t.=8.73 min.

55.4) 2-ethyl-6-methyl-1,3-benzoxazol-4-amine 1.45 g (7.46 mmol) of intermediate 55.3 is dissolved in 25 g of polyphosphoric acid. After stirring for 1 hour at 140° C., the solution is hydrolyzed by the addition of iced water, then neutralized by a 50% aqueous solution of soda. The product obtained is extracted with dichloromethane, and the organic phase is washed 3 times with 25 ml of water, dried over sodium sulphate and concentrated under reduced pressure. The desired product is obtained after purification by chromatography on a silica column (eluent: dichloromethane/ethanol 98/2).

MS-LC: MH+=177.21; r.t.=9.12 min.

55.5) 2-ethyl-6-methyl-1,3-benzoxazole-4,7-dione

The experimental protocol used is identical to that described for Stage 15.3 of Example 15, intermediate 55.4 replacing intermediate 15.2.

NMR $^1$H (DMSO d6, 400 MHz, δ): 6.72 (s, 1H, CH); 2.98-2.93 (q, 2H, $CH_2$); 2.04 (s, 3H, $CH_3$); 1.30 (t, 3H, $CH_3$).
MS-LC: MH+=192.06; r.t.=8.93 min.

55.6) 5-{[2-(dimethylamino)ethyl]amino}-2-ethyl-6-methyl-1,3-benzoxazole-4,7-dione The experimental protocol used is identical to that described for Stage 15.4 of Example 15, intermediate 55.5 replacing intermediate 15.3 and N,N-dimethylethylenediamine replacing aniline. Melting point: 135° C.

NMR $^1$H (DMSO d6, 400 MHz, δ): 6.63 (t, 1H, NH); 3.62-3.58 (m, 2H, $CH_2$); 2.92-2.86 (q, 2H, $CH_2$); 2.44-2.41 (m, 2H, $CH_2$); 2.14 (s, 6H, 2 $CH_3$); 1.97 (s, 3H, $CH_3$); 1.27 (t, 3H, $CH_3$).

MS-LC: MH+=278.12; r.t.=7.27 min.

Example 56

2-cyclopropyl-5-{[2-(dimethylamino)ethyl]amino}-1,3-benzoxazole-4,7-dione or 2-cyclopropyl-6-{[2-(dimethylamino)ethyl]amino}-1,3-benzoxazole-4,7-dione The experimental protocol used is identical to that described for Example 55, cyclohexane-1,3-dione replacing 5-methylcyclohexane-1,3-dione in the first stage and cyclopropanecarbonitrile replacing propionitrile in the second stage. Melting point: 155° C.

NMR $^1$H (DMSO d6, 400 MHz, δ): 7.35 (t, 1H, NH); 5.27 (s, 1H, CH); 3.30-3.18 (m, 2H, $CH_2$); 2.49-2.46 (m, 2H, $CH_2$); 2.28-2.25 (m, 1H, CH); 2.17 (s, 6H, 2 $CH_3$); 1.18-1.07 (m, 4H, 2 $CH_2$).

MS-LC: MH+=276.10; r.t.=7.10 min.

Example 57

Mixture of 5-{[2-(dimethylamino)ethyl]amino}-2-phenyl-1,3-benzoxazole-4,7-dione and 6-{[2-(dimethylamino)ethyl]amino}-2-phenyl-1,3-benzoxazole-4,7-dione The experimental protocol used is identical to that described for Example 15, trimethyl orthobenzoate replacing triethyl orthopropionate in the first stage and N,N-dimethylethylenediamine replacing aniline in the fourth and last stage. Melting point: 147° C.

NMR $^1$H (DMSO d6, 400 MHz, δ): 8.15-8.08 (m, 2H, H arom.); 7.70-7.61 (m, 3H, H arom.); 7.33 (t, 1H, NH); 5.38 (s, 1H, CH); 3.26-3.21 (m, 4H, 2 $CH_2$); 2.19 (s, 6H, 2 $CH_3$).

The two components of the mixture can be characterized by the NMR shifts (400 MHz) of the single proton of the benzoxazoledione ring which are 5.38 and 5.39 ppm.

MS-LC: MH+=312.20; r.t.=7.70 min.

Example 58

Mixture of 5-{[6-(dimethylamino)hexyl]amino}-2-phenyl-1,3-benzoxazole-4,7-dione and 6-{[6-(dimethylamino)hexyl]amino}-2-phenyl-1,3-benzoxazole-4,7-dione The experimental protocol used is identical to that described for Example 15, trimethyl orthobenzoate replacing triethyl orthopropionate in the first stage and 6-(dimethylamino)hexylamine replacing aniline in the fourth and last stage.

The two components of the mixture can be characterized by the NMR shifts (400 MHz) of the single proton of the benzoxazoledione ring which are 5.34 and 5.35 ppm.

MS-LC: MH+=368.20; r.t.=8.10 min.

Example 59

5-[(1-ethylhexyl)amino]-2-phenyl-1,3-benzoxazole-4,7-dione or 6-[(1-ethylhexyl)amino]-2-phenyl-1,3-benzoxazole-4,7-dione The experimental protocol used is identical to that described for Example 15, trimethyl orthobenzoate replacing triethyl orthopropionate in the first stage and 2-ethylhexylamine replacing aniline in the fourth and last stage.

MS-LC: MH+=353.20; r.t.=12.50 min.

Example 60

Mixture of 2-(2,6-difluorophenyl)-5-[(2-pyrrolidin-1-ylethyl)amino]-1,3-benzoxazole-4,7-dione and 2-(2,6-difluorophenyl)-6-[(2-pyrrolidin-1-ylethyl)amino]-1,3-benzoxazole-4,7-dione

60.1) 2-(2,6-difluorophenyl)-4-nitro-1,3-benzoxazole 2 g (32.4 mmol; 1 eq.) of boric acid is added to a solution of 5 g (32.4 mmol) of 2-amino-3-nitrophenol and 5.12 g (32.4 mmol; 1 eq.) of 2,6-difluorobenzoic acid in 50 ml of xylene. The mixture is heated under reflux of the xylene for 8 hours with elimination of the water formed by a Dean-Stark apparatus. After returning to ambient temperature, the reaction medium is diluted by 100 ml of ethyl acetate and neutralized by a 10% aqueous solution of soda. The organic phase is washed 3 times with 50 ml of water then with a saturated solution of NaCl before being dried over sodium sulphate, filtered and concentrated under reduced pressure. The 2-(2,6-difluorophenyl)-4-nitro-1,3-benzoxazole is used without other purification in the following stage.

MS-LC: MH+=277.00; r.t.=10.45 min.

60.2) 2-(2,6-difluorophenyl)-1,3-benzoxazol-4-amine 14.3 g (63.5 mmol; 5 eq.) of tin chloride is added to a solution of 3.5 g (12.7 mmol) of 2-(2,6-difluorophenyl)-4-nitro-1,3-benzoxazole in 60 ml of concentrated hydrochloric acid. The mixture is stirred for 2 hours at 60° C., then, after returning to ambient temperature and the addition of 100 ml of water, is neutralized by a 50% aqueous solution of soda. The precipitate formed is filtered on a Celite bed and washed with ethanol. The resulting solution is concentrated under reduced pressure, then the desired product is extracted 3 times with 50 ml of ethyl acetate. The organic phases are combined, washed twice with 30 ml of a saturated solution of sodium chloride, dried over sodium sulphate and concentrated under reduced pressure. The 2-(2,6-difluorophenyl)-1,3-benzoxazol-4-amine is used without other purification in the following stage.

MS-LC: MH+=247.08; r.t.=10.02 min.

60.3) 2-(2,6-difluorophenyl)-1,3-benzoxazole-4,7-dione

The experimental protocol used is identical to that described for Stage 15.3 of Example 15, intermediate 60.2 replacing intermediate 15.2. The expected product is obtained in the form of yellow crystals.

MS-LC: MH+=261.93; r.t.=9.62 min.

60.4) mixture of 2-(2,6-difluorophenyl)-5-[(2-pyrrolidin-1-ylethyl)amino]-1,3-benzoxazole-4,7-dione and 2-(2,6-difluorophenyl)-6-[(2-pyrrolidin-1-ylethyl)amino]-1,3-benzoxazole-4,7-dione The experimental protocol used is identical to that described for Stage 15.4 of Example 15, intermediate 60.3 replacing intermediate 15.3 and (2-aminoethyl)pyrrolidine replacing aniline. Melting point: 150° C.

NMR $^1$H (DMSO d6, 400 MHz, δ): 7.78-7.76 (m, 1H, H arom.); 7.43-7.37 (m, 2H, H arom.); 5.41 (s, 1H, CH); 3.38-3.36 (m, 2H, $CH_2$); 3.28-3.26 (m, 4H, 2 $CH_2$); 2.68-2.64 (m, 2H, $CH_2$); 1.70-1.67 (m, 4H, 2 $CH_2$).

The two components of the mixture can be characterized by the NMR shifts (400 MHz) of the single proton of the benzoxazoledione ring which are 5.40 and 5.42 ppm.

MS-LC: MH+=373.99; r.t.=7.76 min.

The compounds of Examples 61 to 65 are obtained in similar manner to that described for Example 60.

Example 61

Mixture of 2-[4-(diethylamino)phenyl]-5-{[2-(dimethylamino)ethyl]amino}-1,3-benzoxazole-4,7-dione and 2-[4-(diethylamino)phenyl]-6-{[2-(dimethylamino)ethyl]amino}-1,3-benzoxazole-4,7-dione NMR $^1$H (DMSO d6, 400 MHz, δ): 7.91-7.89 (d, 2H, H arom.); 6.83-6.81 (d, 2H, H arom.); 5.29 (s, 1H, CH); 3.47-3.42 (m, 4H, 2 $CH_2$); 3.41-3.38 (m, 2H, $CH_2$); 3.25-3.21 (m, 2H, $CH_2$); 2.19 (s, 6H, 2 $CH_3$); 1.12 (t, 6H, 2 $CH_3$).

The two components of the mixture can be characterized by the NMR shifts (400 MHz) of the single proton of the benzoxazoledione ring which are 5.29 and 5.30 ppm.

MS-LC: MH+=383.20; r.t.=8.30 min.

Example 62

Mixture of 2-[4-(diethylamino)phenyl]-5-[(2-pyrrolidin-1-ylethyl)amino]-1,3-benzoxazole-4,7-dione and 2-[4-(diethylamino)phenyl]-6-[(2-pyrrolidin-1-ylethyl)amino]-1,3-benzoxazole-4,7-dione NMR $^1$H (DMSO d6, 400 MHz, δ): 7.91-7.88 (d, 2H, H arom.); 6.83-6.81 (d, 2H, H arom.); 5.29 (s, 1H, CH); 3.47-3.42 (m, 4H, 2 $CH_2$); 3.37-3.35 (m, 2H, $CH_2$); 3.26-3.23 (m, 4H, 2 $CH_2$); 2.66 (t, 2H, $CH_2$); 1.70-1.68 (m, 4H, 2 $CH_2$); 1.14 (t, 6H, 2 $CH_3$).

The two components of the mixture can be characterized by the NMR shifts (400 MHz) of the single proton of the benzoxazoledione ring which are 5.28 and 5.29 ppm.

MS-LC: MH+=409.10; r.t.=8.40 min.

Example 63

Mixture of 2-(4-chlorophenyl)-5-{[2-(dimethylamino)ethyl]amino}-1,3-benzoxazole-4,7-dione and 2-(4-chlorophenyl)-6-{[2-(dimethylamino)ethyl]amino}-1,3-benzoxazole-4,7-dione Melting point: 169° C.

The two components of the mixture can be characterized by the NMR shifts (400 MHz) of the single proton of the benzoxazoledione ring which are 5.39 and 5.41 ppm.

MS-LC: MH+=346.20; r.t.=8.10 min.

Example 64

Mixture of 2-(4-chlorophenyl)-5-{[3-(dimethylamino)propyl]amino}-1,3-benzoxazole-4,7-dione and 2-(4-chlorophenyl)-6-{[3-(dimethylamino)propyl]amino}-1,3-benzoxazole-4,7-dione MS-LC: MH+=360.10; r.t.=8.10 min.

Example 65

Mixture of 2-(4-chlorophenyl)-5-{[4-(dimethylamino)butyl]amino}-1,3-benzoxazole-4,7-dione and 2-(4-chlorophenyl)-6-{[4-(dimethylamino)butyl]amino}-1,3-benzoxazole-4,7-dione NMR $^1$H (DMSO d6, 400 MHz, δ): 8.13-8.09 (m, 2H, H arom.); 7.70-7.67 (m, 2H, H arom.); 5.36 (s, 1H, CH); 3.18-3.15 (m, 2H, CH$_2$); 2.25-2.21 (m, 2H, CH$_2$); 2.13 (s, 6H, 2 CH$_3$); 1.62-1.58 (m, 2H, CH$_2$); 1.48-1.44 (m, 2H, CH$_2$).

The two components of the mixture can be characterized by the NMR shifts (400 MHz) of the single proton of the benzoxazoledione ring which are 5.35 and 5.37 ppm.

MS-LC: MH+=374.10; r.t.=8.20 min.

Example 66

Mixture of 2-(2-fluorophenyl)-5-{[2-(dimethylamino)ethyl]amino}-1,3-benzoxazole-4,7-dione and 2-(2-fluorophenyl)-6-{[2-(dimethylamino)ethyl]amino}-1,3-benzoxazole-4,7-dione

66.1) 2-diazocyclohexane-1,3-dione

A mixture of 4-acetamidobenzenesulphonylazide (25 g, 104 mmol) and triethylamine (36 ml, 250 mmol) in dichloromethane maintained at a temperature below 30° C. by external cooling is treated dropwise by a solution of cyclohexane-1,3-dione (13 g, 115 mmol) in 200 ml of dichloromethane. The reaction mixture is stirred for 75 minutes at ambient temperature then filtered on Celite. After concentration to approximately 300 ml, the filtrate is washed with water then dried over sodium sulphate. The brown-yellow solid (14 g; 88%) obtained by evaporation of the solvent under reduced pressure is similar to that obtained in Example 55.1, and is used as it is in the following stage.

NMR $^1$H (DMSO-d$_6$, δ): 1.93 (m, 2H); 2.50 (t, 4H).
NMR $^{13}$C (DMSO-d$_6$, δ): 18.20; 36.68; 190.96.

66.2) 2-(2-fluorophenyl)-6,7-dihydro-1,3-benzoxazol-4 (5H)-one

A mixture of rhodium acetate (32 mg, 72 μmol) and 2-fluorobenzonitrile (2.31 ml; 22 mmol) in perfluorobenzene (5 ml) is treated at 60° C. dropwise by a solution of diazocyclohexanedione (obtained in Stage 66.1; 1 g; 7.24 mmol) in 5 ml of perfluorobenzene. The reaction medium is maintained at 60° C. until exhaustion of the release of nitrogen (1 hour; TLC on SiO$_2$: 2% MeOH/CH$_2$Cl$_2$). After cooling down to ambient temperature and filtration, the solvent of the filtrate is evaporated. The residue is purified by chromatography (SiO$_2$: AcOEt/heptane: 1/1) in order to produce a light yellow powder.

NMR $^1$H (CDCl$_3$, δ): 2.31 (m, 2H); 2.66 (m, 2H,); 3.09 (t, 2H); 7.19-7.28 (m, 2H); 7.48-7.50 (m, 1H); 8.15-8.19 (m, 1H).

MS-LC: MH+=232.08; r.t.=9.28 min.

66.3) 5-bromo-2-(2-fluorophenyl)-6,7-dihydro-1,3-benzoxazol-4 (5H)-one

A solution of intermediate 66.2 (470 mg, 2 mmol) in acetic acid (5 ml) is treated with bromine in acetic acid (0.2M; 10 ml; 2 mmol) for 4 days at ambient temperature (TLC on SiO$_2$: AcOEt/heptane: 1/1). The reaction medium is then diluted with water and extracted using dichloromethane. The organic phases are combined, washed with a saturated solution of bicarbonate then with a 5% solution of sodium disulphite. After drying over sodium sulphate and elimination of the volatile constituents under reduced pressure, a yellow oil is obtained which is purified by chromatography (SiO$_2$: AcOEt/heptane: 1/1) in order to produce a white powder.

NMR $^1$H (DMSO-d$_6$, δ): 2.49 (m, 2H); 2.73 (m, 1H,); 3.15 (m, 2H); 4.95 (t, 1H,); 7.39-7.48 (m, 2H); 7.63-7.67 (m, 1H); 8.03-8.08 (t, 1H).

MS-LC: MH+=309.93; r.t.=10.08 min.

66.4) 2-(2-fluorophenyl)-4-hydroxy-1,3-benzoxazole

Intermediate 66.3 (6.52 g; 21 mmol) in solution in tetrahydrofuran (100 ml) is treated dropwise by diazabicyclo [5.4.0]undec-7-ene (4.7 ml; 31 mmol). When the reaction is complete (1.5 hours; TLC on SiO$_2$: AcOEt/heptane: 1/1), the reaction mixture is diluted with ethyl acetate then washed successively with 1N hydrochloric acid and a saturated solution of sodium chloride. The combined organic phases are dried and concentrated in order to produce a brown residue which is purified by chromatography (SiO$_2$: AcOEt/heptane: 1/1) in order to produce a beige powder.

NMR $^1$H (DMSO-d$_6$, δ): 6.80 (d, 1H); 7.19-7.26 (m, 2H); 7.41-7.49 (m, 2H); 7.65 (m, 1H); 8.18 (t, 1H); 10.43 (s, 1H).

MS-LC: MH+=230.07; r.t.=10.03 min.

66.5) 2-(2-fluorophenyl)-1,3-benzoxazole-4,7-dione

The experimental protocol used is identical to that described for Stage 15.3 of Example 15, intermediate 66.4 replacing intermediate 15.2. A yellow powder is obtained.

NMR $^1$H (DMSO-d$_6$, δ): 6.94 (broad, 2H); 7.45-7.54 (m, 2H); 7.74 (m, 2H); 8.18 (t, 1H).

MS-LC: MH+=244.04; r.t.=9.73 min. (61%) and MH$_3$+ =246.06; r.t.=8.70 min.

66.6) Mixture of 2-(2-fluorophenyl)-5-{[2-(dimethylamino)ethyl]amino}-1,3-benzoxazole-4,7-dione and 2-(2-fluorophenyl)-6-{[2-(dimethylamino)ethyl] amino}-1,3-benzoxazole-4,7-dione The experimental protocol used is identical to that described for Stage 15.4 of Example 15, intermediate 66.5 replacing intermediate 15.3 and N,N-dimethylethylenediamine replacing aniline. A ruby-coloured powder is obtained. Melting point: 191° C.

NMR $^1$H (DMSO-d$_6$, δ): 2.19 (s, 6H); 2.5 (m, 2H); 3.27 (m, 2H); 5.41 (s, 1H); 7.42-7.52 (m, 3H); 7.70 (m, 2H); 8.13 (m, 1H).

The two components of the mixture can be characterized by the NMR shifts (400 MHz) of the single proton of the benzoxazoledione ring which are 5.40 and 5.41 ppm.

MS-LC: MH+=330.14; r.t.=7.69 min.

Example 67

Mixture of 2-(2-fluorophenyl)-5-[(2-pyrrolidin-1-ylethyl)amino]-1,3-benzoxazole-4,7-dione and 2-(2-fluorophenyl)-6-[(2-pyrrolidin-1-ylethyl)amino]-1,3-benzoxazole-4,7-dione The experimental protocol used is identical to that described for Example 66, N-(2-aminoethyl)-pyrrolidine replacing N,N-dimethylethylenediamine. Melting point: 152° C.

The two components of the mixture can be characterized by the NMR shifts (400 MHz) of the single proton of the benzoxazoledione ring which are 5.39 and 5.41 ppm.
MS-LC: MH+=356.1; r.t.=7.8 min.

Example 68

Mixture of 2-(2-bromophenyl)-5-{[2-(dimethylamino)ethyl]amino}-1,3-benzoxazole-4,7-dione and 2-(2-bromophenyl)-6-{[2-(dimethylamino)ethyl]amino}-1,3-benzoxazole-4,7-dione

68.1) 2-(2-bromophenyl)-6,7-dihydro-1,3-benzoxazol-4 (5H)-one

The experimental protocol used is identical to that described for Stage 66.2, 2-bromobenzonitrile replacing 2-fluorobenzonitrile. A yellow solid is obtained.
MS-LC: MH+=292.0; r.t.=9.8 min.

68.2) 5-bromo-2-(2-bromophenyl)-6,7-dihydro-1,3-benzoxazol-4 (5H)-one

A mixture of intermediate 68.1 (6.6 g, 22 mmol) and CuBr$_2$ (10 g; 45 mmol) in ethyl acetate (250 ml) with approximately 1 ml of acetic acid added to it is taken to reflux for 3.5 hours (TLC on SiO$_2$: AcOEt/heptane: 1/1). The reaction medium is then filtered on Celite, the filtrate is evaporated under reduced pressure and the residue is purified on a column (SiO$_2$: AcOEt/heptane: 1/1) in order to produce a light yellow powder.
MS-LC: MH+=371.8; r.t.=10.5 min.

68.3) 2-(2-bromophenyl)-5-{[2-(dimethylamino)ethyl]amino}-1,3-benzoxazole-4,7-dione This compound is obtained from intermediate 68.2 according to the operating methods described for Stages 66.4, 66.5 and 66.6. Melting point: 138° C.

The two components of the mixture can be characterized by the NMR shifts (400 MHz) of the single proton of the benzoxazoledione ring which are 5.41 and 5.43 ppm.
MS-LC: MH+=390.0; r.t.=7.9 min.

Example 69

Mixture of 2-(2-bromophenyl)-5-[(2-pyrrolidin-1-ylethyl)amino]-1,3-benzoxazole-4,7-dione and 2-(2-bromophenyl)-6-[(2-pyrrolidin-1-ylethyl)amino]-1,3-benzoxazole-4,7-dione The experimental protocol used is identical to that described for Example 68, N-(2-aminoethyl)-pyrrolidine replacing N,N-dimethylethylenediamine. Melting point: 122° C.

The two components of the mixture can be characterized by the NMR shifts (400 MHz) of the single proton of the benzoxazoledione ring which are 5.40 and 5.42 ppm.
MS-LC: MH+=416.0; r.t.=8.0 min.

Example 70

Mixture of 2-(2-bromophenyl)-5-{[3-(dimethylamino)propyl]amino}-1,3-benzoxazole-4,7-dione and 2-(2-bromophenyl)-6-{[3-(dimethylamino)propyl]amino}-1,3-benzoxazole-4,7-dione The experimental protocol used is identical to that described for Example 68, N,N-dimethylpropylenediamine replacing N,N-dimethylethylenediamine. Melting point: 119° C.

The two components of the mixture can be characterized by the NMR shifts (400 MHz) of the single proton of the benzoxazoledione ring which are 5.38 and 5.40 ppm.
MS-LC: MH+=404.0; r.t.=8.0 min.

Example 71

Mixture of 2-(2-chlorophenyl)-5-{[2-(dimethylamino)ethyl]amino}-1,3-benzoxazole-4,7-dione and 2-(2-chlorophenyl)-6-{[2-(dimethylamino)ethyl]amino}-1,3-benzoxazole-4,7-dione The experimental protocol used is identical to that described for Example 66, 2-chlorobenzonitrile replacing 2-fluorobenzonitrile. Melting point: 137° C.

The two components of the mixture can be characterized by the NMR shifts (400 MHz) of the single proton of the benzoxazoledione ring which are 5.39 and 5.41 ppm.
MS-LC: MH+=346.1; r.t.=7.8 min.

Example 72

Mixture of 2-(2-chlorophenyl)-5-[(2-pyrrolidin-1-ylethyl)amino]-1,3-benzoxazole-4,7-dione and 2-(2-chlorophenyl)-6-[(2-pyrrolidin-1-ylethyl)amino]-1,3-benzoxazole-4,7-dione The experimental protocol used is identical to that described for Example 71, N-(2-aminoethyl)-pyrrolidine replacing N,N-dimethylethylenediamine. Melting point: 85° C.

The two components of the mixture can be characterized by the NMR shifts (400 MHz) of the single proton of the benzoxazoledione ring which are 5.40 and 5.41 ppm.
MS-LC: MH+=372.1; r.t.=8.0 min.

Example 73

Mixture of 2-(3-bromophenyl)-5-{[2-(dimethylamino)ethyl]amino}-1,3-benzoxazole-4,7-dione and 2-(3-bromophenyl)-6-{[2-(dimethylamino)ethyl]amino}-1,3-benzoxazole-4,7-dione The experimental protocol used is identical to that described for Example 68, 3-bromobenzonitrile replacing 2-bromobenzonitrile. Melting point: 133° C.

The two components of the mixture can be characterized by the NMR shifts (400 MHz) of the single proton of the benzoxazoledione ring which are 5.39 and 5.41 ppm.
MS-LC: MH+=390.0; r.t.=8.1 min.

Example 74

Mixture of 2-(4-bromophenyl)-5-[(2-pyrrolidin-1-ylethyl)amino]-1,3-benzoxazole-4,7-dione and 2-(4-bromophenyl)-6-[(2-pyrrolidin-1-ylethyl)amino]-1,3-benzoxazole-4,7-dione The experimental protocol used is identical to that described for Example 68, 4-bromobenzonitrile replacing 2-bromobenzonitrile, and N-(2-aminoethyl)-pyrrolidine replacing N,N-dimethylethylenediamine. Melting point: 181° C.

The two components of the mixture can be characterized by the NMR shifts (400 MHz) of the single proton of the benzoxazoledione ring which are 5.37 and 5.39 ppm.

MS-LC: MH+=415.0; r.t.=8.3 min.

Example 75

Mixture of 2-(4-bromophenyl)-5-{[2-(dimethylamino)ethyl]amino}-1,3-benzoxazole-4,7-dione and 2-(4-bromophenyl)-6-{[2-(dimethylamino)ethyl]amino}-1,3-benzoxazole-4,7-dione The experimental protocol used is identical to that described for Example 74, N,N-dimethylethylenediamine replacing N-(2-aminoethyl)-pyrrolidine. Melting point: 184° C.

The two components of the mixture can be characterized by the NMR shifts (400 MHz) of the single proton of the benzoxazoledione ring which are 5.38 and 5.40 ppm.

MS-LC: MH+=390.1; r.t.=8.2 min.

Example 76

Mixture of 2-(4-fluorophenyl)-5-[(2-pyrrolidin-1-ylethyl)amino]-1,3-benzoxazole-4,7-dione and 2-(4-fluorophenyl)-6-[(2-pyrrolidin-1-lethyl)amino]-1,3-benzoxazole-4,7-dione 76.1) 2-(4-fluorophenyl)-6,7-dihydro-1,3-benzoxazol-4 (5H)-one:

The experimental protocol used is identical to that described for Stage 66.2, 4-fluorobenzonitrile replacing 2-fluorobenzonitrile. A yellow solid is obtained.

MS-LC: MH+=232.1; r.t.=9.4 min.

76.2) 5-bromo-2-(4-fluorophenyl)-6,7-dihydro-1,3-benzoxazol-4 (5H)-one:

Pyridinium tribromide (996 mg; 3.11 mmol) is added in three equal portions separated by intervals of 2-3 minutes to a solution of intermediate 76.1 (600 mg; 2.59 mmol) in glacial acetic acid (25 ml) taken to 50° C. The reaction mixture is maintained at 50° C. for 4 hours (TLC on $SiO_2$: AcOEt/heptane: 1/1). The volatile constituents are evaporated under reduced pressure, then the residue is taken up in water and extracted with dichloromethane. The reaction medium is then filtered on Celite, the filtrate is evaporated under reduced pressure and the residue is purified on a column ($SiO_2$: AcOEt/heptane: 1/1) in order to produce a light yellow powder. The organic phases are combined and washed with a 10% bicarbonate solution then with a saturated solution of sodium chloride. After drying over sodium sulphate and elimination of the volatile constituents under reduced pressure, the residue is purified by chromatography on a column ($SiO_2$: AcOEt/heptane: 1/1) in order to produce a beige powder.

MS-LC: MH+=312.0; r.t.=10.3 min.

76.3) Mixture of 2-(4-fluorophenyl)-5-{[2-(dimethylamino)ethyl]amino}-1,3-benzoxazole-4,7-dione and 2-(4-fluorophenyl)-6-{[2-(dimethylamino)ethyl]amino}-1,3-benzoxazole-4,7-dione This compound is obtained from intermediate 76.2 according to the operating methods described for Stages 66.4, 66.5 and 66.6. Melting point: 162° C.

The two components of the mixture can be characterized by the NMR shifts (400 MHz) of the single proton of the benzoxazoledione ring which are 5.37 and 5.39 ppm.

MS-LC: MH+=356.1; r.t.=8.0 min.

Example 77

Mixture of 5-{[2-(dimethylamino)ethyl]amino}-2-(4-fluorophenyl)-1,3-benzoxazole-4,7-dione and 6-{[2-(dimethylaniino)ethyl]axino}-2-(4-fluorophenyl)-1,3-benzoxazole-4,7-dione The experimental protocol used is identical to that described for Example 76, N-(2-aminoethyl)-pyrrolidine replacing N,N-dimethylethylenediamine. Melting point: 170° C.

The two components of the mixture can be characterized by the NMR shifts (400 MHz) of the single proton of the benzoxazoledione ring which are 5.38 and 5.39 ppm.

MS-LC: MH+=330.1; r.t.=7.8 min.

Example 78

Mixture of 5-[(1-benzylpyrrolidin-3-yl)amino]-2-(4-fluorophenyl)-1,3-benzoxazole-4,7-dione and 6-[(1-benzylpyrrolidin-3-yl)amino]-2-(4-fluorophenyl)-1,3-benzoxazole-4,7-dione The experimental protocol used is identical to that described for Example 76, (1-benzylpyrrolidin-3-yl)-amine replacing N,N-dimethylethylenediamine. Melting point: 180° C.

The two components of the mixture can be characterized by the NMR shifts (400 MHz) of the single proton of the benzoxazoledione ring which are 5.37 and 5.39 ppm.

MS-LC: MH+=418.1; r.t.=8.5 min.

Example 79

Mixture of 5-{[3-(dimethylamino)propyl]amino}-2-(4-fluorophenyl)-1,3-benzoxazole-4,7-dione and 6-{[3-(dimethylamino)propyl]amino}-2-(4-fluorophenyl)-1,3-benzoxazole-4,7-dione The experimental protocol used is identical to that described for Example 76, N,N-dimethylpropylenediamine replacing N,N-dimethylethylenediamine. Melting point: 149° C.

The two components of the mixture can be characterized by the NMR shifts (400 MHz) of the single proton of the benzoxazoledione ring which are 5.35 and 5.37 ppm.

MS-LC: MH+=344.2; r.t.=7.9 min.

Example 80

Mixture of 2-(3,5-difluorophenyl)-5-[(2-pyrrolidin-1-ylethyl)amino]-1,3-benzoxazole-4,7-dione and 2-(3,5-difluorophenyl)-6-[(2-pyrrolidin-1-ylethyl)amino]-1,3-benzoxazole-4,7-dione The experimental protocol used is identical to that described for Example 68, 3,5-difluorobenzonitrile replacing 2-bromobenzonitrile and N-(2-aminoethyl)-pyrrolidine replacing NN-dimethylethylenediamine. Melting point: 158° C.

The two components of the mixture can be characterized by the NMR shifts (400 MHz) of the single proton of the benzoxazoledione ring which are 5.41 and 5.43 ppm.

MS-LC: MH+=374.0; r.t.=8.0 min.

Example 81

Mixture of 2-(3,5-difluorophenyl)-5-{[2-(dimethylamino)ethyl]amino}-1,3-benzoxazole-4,7-dione and 2-(3,5-difluorophenyl)-6-{[2-(dimethylamnno)ethyl]amino}-1,3-benzoxazole-4,7-dione The experimental protocol used is identical to that described for Example 68, 3,5-difluorobenzonitrile replacing 2-bromobenzonitrile. Melting point: 175° C.

The two components of the mixture can be characterized by the NMR shifts (400 MHz) of the single proton of the benzoxazoledione ring which are 5.33 and 5.41 ppm.

MS-LC: MH+=348.0; r.t.=7.9 min.

Example 82

Mixture of 2-(2,5-difluorophenyl)-5-[(2-pyrrolidin-1-ylethyl)amino]-1,3-benzoxazole-4,7-dione and 2-(2,5-difluorophenyl)-6-[(2-pyrrolidin-1-ylethyl)amino]-1,3-benzoxazole-4,7-dione The experimental protocol used is identical to that described for Example 68, 2,5-difluorobenzonitrile replacing 2-bromobenzonitrile and N-(2-aminoethyl)-pyrrolidine replacing N,N-dimethylethylenediamine.

Melting point: 163° C.

The two components of the mixture can be characterized by the NMR shifts (400 MHz) of the single proton of the benzoxazoledione ring which are 5.40 and 5.42 ppm.

MS-LC: MH+=374.0; r.t.=7.9 min.

Example 83

Mixture of 2-(2,5-difluorophenyl)-5-{[2-(dimethylamino)ethyl]amino}-1,3-benzoxazole-4,7-dione and 2-(2,5-difluorophenyl)-6-{[2-(dimethylamino)ethyl]amino}-1,3-benzoxazole-4,7-dione The experimental protocol used is identical to that described for Example 68, 2,5-difluorobenzonitrile replacing 2-bromobenzonitrile.

The two components of the mixture can be characterized by the NMR shifts (400 MHz) of the single proton of the benzoxazoledione ring which are 5.41 and 5.43 ppm.

MS-LC: MH+=348.0; r.t.=7.7 min.

Example 84

Mixture of 2-(2,3-difluorophenyl)-5-{[2-(dimethylamino)ethyl]amino}-1,3-benzoxazole-4,7-dione and 2-(2,3-difluorophenyl)-6-{[2-(dimethylamino)ethyl]amino}-1,3-benzoxazole-4,7-dione The experimental protocol used is identical to that described for Example 68, 2,3-difluorobenzonitrile replacing 2-bromobenzonitrile. Melting point: 167° C.

The two components of the mixture can be characterized by the NMR shifts (400 MHz) of the single proton of the benzoxazoledione ring which are 5.41 and 5.43 ppm.

MS-LC: MH+=348.1; r.t.=7.8 min.

Example 85

Mixture of 2-(2,3-difluorophenyl)-5-[(2-pyrrolidin-1-ylethyl)amino]-1,3-benzoxazole-4,7-dione and 2-(2,3-difluorophenyl)-6-[(2-pyrrolidin-1-ylethyl)amino]-1,3-benzoxazole-4,7-dione The experimental protocol used is identical to that described for Example 68, 2,3-difluorobenzonitrile replacing 2-bromobenzonitrile and N-(2-aminoethyl)-pyrrolidine replacing N,N-dimethylethylenediamine. Melting point: 150° C.

The two components of the mixture can be characterized by the NMR shifts (400 MHz) of the single proton of the benzoxazoledione ring which are 5.40 and 5.42 ppm.

MS-LC: MH+=374.1; r.t.=7.9 min.

Example 86

Mixture of 2-(2,3-difluorophenyl)-5-{[3-(dimethylamino)propyl]amino}-1,3-benzoxazole-4,7-dione and 2-(2,3-difluorophenyl)-6-{[3-(dimethylamino)propyl]amino}-1,3-benzoxazole-4,7-dione The experimental protocol used is identical to that described for Example 68, 2,3-difluorobenzonitrile replacing 2-bromobenzonitrile, and N,N-dimethylpropylenediamine replacing N,N-dimethylethylenediamine. Melting point: 169° C.

The two components of the mixture can be characterized by the NMR shifts (400 MHz) of the single proton of the benzoxazoledione ring which are 5.38 and 5.41 ppm.

MS-LC: MH+=362.1; r.t.=7.8 min.

Example 87

Mixture of 5-[(2-pyrrolidin-1-ylethyl)amino]-2-(3,4,5-trifluorophenyl)-1,3-benzoxazole-4,7-dione and 6-[(2-pyrrolidin-1-ylethyl)amino]-2-(3,4,5-trifluorophenyl)-1,3-benzoxazole-4,7-dione The experimental protocol used is identical to that described for Example 68, 3,4,5-trifluorobenzonitrile replacing 2-bromobenzonitrile, and N-(2-aminoethyl)-pyrrolidine replacing N,N-dimethylethylenediamine.

The two components of the mixture can be characterized by the NMR shifts (400 MHz) of the single proton of the benzoxazoledione ring which are 5.39 and 5.41 ppm.

MS-LC: MH+=392.0; r.t.=8.2 min.

Example 88

Mixture of 5-{[2-(dimethylamino)ethyl]amino}-2-(3,4,5-trifluorophenyl)-1,3-benzoxazole-4,7-dione and 6-{[2-(dimethylamino)ethyl]amino}-2-(3,4,5-trifluorophenyl)-1,3-benzoxazole-4,7-dione The experimental protocol used is identical to that described for Example 68, 3,4,5-trifluorobenzonitrile replacing 2-bromobenzonitrile.

The two components of the mixture can be characterized by the NMR shifts (400 MHz) of the single proton of the benzoxazoledione ring which are 5.40 and 5.42 ppm.

MS-LC: MH+=366.1; r.t.=8.1 min.

Example 89

Mixture of 5-[(2-pyrrolidin-1-ylethyl)amino]-2-(2,3,4,5-tetrafluorophenyl)-1,3-benzoxazole-4,7-dione and 6-[(2-pyrrolidin-1-ylethyl)amino]-2-(2,3,4,5-tetrafluorophenyl)-1,3-benzoxazole-4,7-dione The experimental protocol used is identical to that described for Example 68, 2,3,4,5-tetrafluorobenzonitrile replacing 2-bromobenzonitrile and N-(2-aminoethyl)-pyrrolidine replacing N,N-dimethylethylenediamine.

The two components of the mixture can be characterized by the NMR shifts (400 MHz) of the single proton of the benzoxazoledione ring which are 5.42 and 5.44 ppm.

MS-LC: MH+=410.0; r.t.=8.2 min.

Example 90

Mixture of 5-{[2-(dimethylamino)ethyl]amino}-2-(2,3,4,5-tetrafluorophenyl)-1,3-benzoxazole-4,7-dione and 6-{[2-(dimethylamino)ethy]amino}-2-(2,3,4,5-tetrafluorophenyl)-1,3-benzoxazole-4,7-dione The experimental protocol used is identical to that described for Example 68, 2,3,4,5-tetrafluorobenzonitrile replacing 2-bromobenzonitrile. Melting point: 160° C.

The two components of the mixture can be characterized by the NMR shifts (400 MHz) of the single proton of the benzoxazoledione ring which are 5.42 and 5.45 ppm.

MS-LC: MH+=384.0; r.t.=8.1 min.

Example 91

Mixture of 5-{[2-(dimethylamino)ethyl]amino}-2-[2-fluoro-6-(trifluoromethyl)phenyl]-1,3-benzoxazole-4,7-dione and 6-{[2-(dimethylamino)ethyl]amino}-2-[2-fluoro-6-(trifluoromethyl)phenyl]-1,3-benzoxazole-4,7-dione The experimental protocol used is identical to that described for Example 68, 2-fluoro-6-(trifluoromethyl)-benzonitrile replacing 2-bromobenzonitrile.

The two components of the mixture can be characterized by the NMR shifts (400 MHz) of the single proton of the benzoxazoledione ring which are 5.44 and 5.46 ppm.

MS-LC: MH+=398.0; r.t.=8.0 min.

Example 92

Mixture of 2-[2-fluoro-6-(trifluoromethyl)phenyl]-5-[(2-pyrrolidin-1-ylethyl)amino]-1,3-benzoxazole-4,7-dione and 2-[2-fluoro-6-(trifluoromethyl)phenyl]-6-[(2-pyrrolidin-1-ylethyl)amino]-1,3-benzoxazole-4,7-dione The experimental protocol used is identical to that described for Example 68, 2-fluoro-6-(trifluoromethyl)-benzonitrile replacing 2-bromobenzonitrile and N-(2-aminoethyl)-pyrrolidine replacing N,N-dimethylethylenediamine. Melting point: 166° C.

The two components of the mixture can be characterized by the NMR shifts (400 MHz) of the single proton of the benzoxazoledione ring which are 5.43 and 5.45 ppm.

MS-LC: MH+=424.1; r.t.=8.1 min.

Example 93

Mixture of 5-{[3-(dimethylamino)propyl]amino}-2-[2-fluoro-6-(trifluoromethyl)phenyl]-1,3-benzoxazole-4,7-dione and 6-{[3-(dimethylamino)propyl]amino}-2-[2-fluoro-6-(trifluoromethyl)phenyl]-1,3-benzoxazole-4,7-dione The experimental protocol used is identical to that described for Example 68, 2-fluoro-6-(trifluoromethyl)-benzonitrile replacing 2-bromobenzonitrile and N,N-dimethylpropylenediamine replacing N,N-dimethylethylenediamine. Melting point: 128° C.

The two components of the mixture can be characterized by the NMR shifts (400 MHz) of the single proton of the benzoxazoledione ring which are 5.42 and 5.43 ppm.

MS-LC: MH+=412.0; r.t.=8.0 min.

Example 94

Mixture of 2-[2-chloro-5-(trifluoromethyl)phenyl]-5-{[2-(dimethylamino)ethyl]amino}-1,3-benzoxazole-4,7-dione and 2-[2-chloro-5-(trifluoromethyl)phenyl]-6-{[2-(dimethylamino)ethyl]amino}-1,3-benzoxazole-4,7-dione The experimental protocol used is identical to that described for Example 68, 2-chloro-5-(trifluoromethyl)-benzonitrile replacing 2-bromobenzonitrile. Melting point: 182° C.

The two components of the mixture can be characterized by the NMR shifts (400 MHz) of the single proton of the benzoxazoledione ring which are 5.43 and 5.46 ppm.

MS-LC: MH+=414.0; r.t.=8.3 min.

Example 95

Mixture of 2-[2-chloro-5-(trifluoromethyl)phenyl]-5-[(2-pyrrolidin-1-ylethyl)amino]-1,3-benzoxazole-4,7-dione and 2-[2-chloro-5-(trifluoromethyl)phenyl]-6-[(2-pyrrolidin-1-ylethyl)amino]-1,3-benzoxazole-4,7-dione The experimental protocol used is identical to that described for Example 68, 2-chloro-5-(trifluoromethyl)-benzonitrile replacing 2-bromobenzonitrile and N-(2-aminoethyl)-pyrrolidine replacing N,N-dimethylethylenediamine. Melting point: 152° C.

The two components of the mixture can be characterized by the NMR shifts (400 MHz) of the single proton of the benzoxazoledione ring which are 5.43 and 5.45 ppm.
MS-LC: MH+=440.0; r.t.=8.5 min.

Example 96

Mixture of 2-[2-chloro-5-(trifluoromethyl)phenyl]-5-{[3-(dimethylamino)propyl]amino}-1,3-benzoxazole-4,7-dione and 2-[2-chloro-5-(trifluoromethyl)phenyl]-6-{[3-(dimethylamino)propyl]amino}-1,3-benzoxazole-4,7-dione The experimental protocol used is identical to that described for Example 68, 2-chloro-5-(trifluoromethyl)-benzonitrile replacing 2-bromobenzonitrile and N,N-dimethylpropylenediamine replacing NN-dimethylethylenediamine. Melting point: 121° C.
The two components of the mixture can be characterized by the NMR shifts (400 MHz) of the single proton of the benzoxazoledione ring which are 5.41 and 5.43 ppm.
MS-LC: MH+=428.0; r.t.=8.4 min.

Example 97

Mixture of 2-[2-chloro-6-fluorophenyl]-5-{[3-(dimethylamino)propyl]amino}-1,3-benzoxazole-4,7-dione and 2-[2-chloro-6-fluorophenyl]-6-{[3-(dimethylamino)propyl]amino}-1,3-benzoxazole-4,7-dione The experimental protocol used is identical to that described for Example 68, 2-chloro-6-fluorobenzonitrile replacing 2-bromobenzonitrile.
The two components of the mixture can be characterized by the NMR shifts (400 MHz) of the single proton of the benzoxazoledione ring which are 5.43 and 5.45 ppm.
MS-LC: MH+=364.1; r.t.=7.8 min.

Example 98

Mixture of 2-[2-chloro-6-fluorophenyl]-5-[(2-pyrrolidin-1-ylethyl)amino]-1,3-benzoxazole-4,7-dione and 2-[2-chloro-6-fluorophenyl]-6-[(2-pyrrolidin-1-ylethyl)amino]-1,3-benzoxazole-4,7-dione The experimental protocol used is identical to that described for Example 68, 2-chloro-6-fluorobenzonitrile replacing 2-bromobenzonitrile and N-(2-aminoethyl)-pyrrolidine replacing N,N-dimethylethylenediamine. Melting point: 124° C.
The two components of the mixture can be characterized by the NMR shifts (400 MHz) of the single proton of the benzoxazoledione ring which are 5.42 and 5.44 ppm.
MS-LC: MH+=390.1; r.t.=7.9 min.

Example 99

Mixture of 2-[3,4-dimethoxyphenyl]-5-{[2-(dimethylamino)ethyl]amino}-1,3-benzoxazole-4,7-dione and 2-[3,4-dimethoxyphenyl]-6-{[2-(dimethylamino)ethyl]amino}-1,3-benzoxazole-4,7-dione 99.1) 2-(3,4-dimethoxyphenyl)-6,7-dihydro-1,3-benzoxazol-4 (5H)-one The experimental protocol used is identical to that described for Stage 66.2, 3,4-dimethoxybenzonitrile replacing 2-fluorobenzonitrile. A yellow solid is obtained.
MS-LC: MH+=274.0; r.t.=8.9 min.

99.2) 5-iodo-2-(3,4-dimethoxyphenyl)-6,7-dihydro-1,3-benzoxazol-4 (5H)-one

A solution of intermediate 99.1 (500 mg, 1.83 mmol) in acetic acid (30 ml) is treated for 96 hours at ambient temperature by poly[styrene-co-(4-vinylpyridinium dichloroiodate(1-))] (2.6 g; 8.25 mEq; prepare according to B Šket et al., *Bull. Chem. Soc. Jpn* (1989), 62, 3406-3408) (TLC verification on $SiO_2$: 2% $MeOH/CH_2Cl_2$). The polymer is removed by filtration and the volatile constituents are evaporated under reduced pressure. The residue is purified on a column ($SiO_2$: 1% $MeOH/CH_2Cl_2$) in order to produce a yellow oil.
MS-LC: MH+=399.9; r.t.=9.8 min.

99.3) Mixture of 2-(3,4-dimethoxyphenyl)-5-{[2-(dimethylamino)ethyl]amino}-1,3-benzoxazole-4,7-dione and 2-(3,4-dimethoxyphenyl)-6-{([2-(dimethylamino)ethyl]amino}-1,3-benzoxazole-4,7-dione This compound is obtained from intermediate 99.2 according to the operating methods described for Stages 66.4, 66.5 and 66.6. Melting point: 181° C.
The two components of the mixture can be characterized by the NMR shifts (400 MHz) of the single proton of the benzoxazoledione ring which are 5.35 and 5.36 ppm.
MS-LC: MH+=372.1; r.t.=7.6 min.

Example 100

Mixture of 2-[2-bromo-3-pyridyl]-5-{[2-(dimethylamino)ethyl]amino}-1,3-benzoxazole-4,7-dione and 2-[2-bromo-3-pyridyl]-6-{[2-(dimethylamino)ethyl]amino}-1,3-benzoxazole-4,7-dione The experimental protocol used is identical to that described for Example 68, 2-bromonicotinonitrile replacing 2-bromobenzonitrile. Melting point: 133° C.
The two components of the mixture can be characterized by the NMR shifts (400 MHz) of the single proton of the benzoxazoledione ring which are 5.43 and 5.45 ppm.
MS-LC: MH+=391.0; r.t.=7.4 min.

Example 101

Mixture of 2-cyclohexyl-5-[(2-pyrrolidin-1-ylethyl)amino]-1,3-benzothiazole-4,7-dione and 2-cyclohexyl-6-[(2-pyrrolidin-1-ylethyl)amino]-1,3-benzothiazole-4,7-dione 101.1) N-(2,5-dimethoxyphenyl)cyclohexanecarboxamide 1 ml (7.62 mmol, 1.1 eq.) of cyclohexanoic acid chloride is added to a solution of 1.05 g (6.89 mmol) of 2,5-dimethoxyaniline in 10 ml of a mixture toluene/methanol (1/1). The reaction mixture is maintained under stirring at 70° C. for 1.5 hour, and, after returning to ambient temperature, is poured into 50 ml of water. The expected product is extracted twice with 50 ml of toluene, then washed twice with 50 ml of water. The organic phases are combined, dried over magnesium sulphate and the solvent evaporated off under reduced pressure. 1.46 g (yield=67%) of N-(2,5-dimethoxyphenyl)cyclohexanecarboxamide is obtained and used without other purification in the following stage.

NMR ¹H (DMSO d6, 400 MHz, δ): 8.84 (s, 1H, NH); 7.72-7.71 (m, 1H, H arom.); 6.93-6.91 (d, 1H, H arom.); 6.60-6.57 (m, 1H, H arom.); 3.76 (s, 3H, CH$_3$); 3.66 (s, 3H, CH$_3$); 1.78-1.70 (m, 6H, CH$_2$, CH); 1.38-1.24 (m, 5H, CH$_2$).
MS-LC: MH+=264.14; r.t.=10.76 min.

101.2)
N-(2,5-dimethoxyphenyl)cyclohexanecarbothioamide 1.46 g (5.54 mmol) of N-(2,5-dimethoxyphenyl)cyclohexanecarboxamide is put into solution in 40 ml of anhydrous toluene. The solution is taken to 100° C., and 3.34 g (8.26 mmol; 1.5 eq.) of Lawesson's reagent are added to the reaction medium which is then maintained under stirring at 100° C. for 4 hours. After returning to ambient temperature, the solution is poured into 50 ml of iced water and extracted using toluene. The organic phases are dried over magnesium sulphate and the solvent is evaporated off. The N-(2,5-dimethoxyphenyl)cyclohexanecarbothioamide is then purified by chromatography on a silica column (eluent: dichloromethane/heptane: 1/1 then 3/2). 1.26 g (yield=81%) of product is obtained in the form of yellow oil.
NMR ¹H (DMSO d6, 400 MHz, δ): 10.76 (s, 1H, NH); 7.28-7.27 (m, 1H, H arom.); 7.02-6.99 (d, 1H, H arom.); 6.82-6.80 (m, 1H, H arom.); 3.73 (s, 3H, CH$_3$); 3.68 (s, 3H, CH$_3$); 1.77-1.75 (m, 4H, CH$_2$); 1.67-1.58 (m, 3H, CH$_2$, CH); 1.31-1.15 (m, 4H, 2CH$_2$).
MS-LC: MH+=280.12; r.t.=11.38 min.

101.3)
2-cyclohexyl-4,7-dimethoxy-1,3-benzothiazole 1.26 g (4.50 mmol) of N-(2,5-dimethoxyphenyl)cyclohexanecarbothioamide is dissolved in 100 ml of a 1.5 M sodium hydroxide solution (100 ml) and the reaction medium is cooled down to 0° C. before adding 25 ml of a freshly prepared 20% aqueous solution of potassium ferricyanide (5.05 g of K$_3$[Fe(CN)$_6$]; 3.4 eq.). The reaction mixture is maintained under stirring at ambient temperature for 24 hours, then 1.1 g (yield=88%) of the expected benzothiazole derivative is obtained by filtration, washing with cold water and drying under reduced pressure in the presence of P$_2$O$_5$.
NMR ¹H (DMSO d6, 400 MHz, δ): 6.95-6.85 (dd, 2H, H arom.); 3.88 (s, 6H, 2CH$_3$); 3.10-3.04 (m, 1H, CH); 2.10-2.07 (m, 2H, CH$_2$); 1.81-1.77 (m, 2H, CH$_2$); 1.70-1.67 (m, 1H, CH); 1.57-1.51 (m, 2H, CH$_2$); 1.42-1.39 (m, 2H, CH$_2$); 1.26-1.28 (m, 1H, CH).
MS-LC: MH+=278.09; r.t.=11.91 min.

101.4) 2-cyclohexyl-1,3-benzothiazole-4,7-dione 1 g (3.61 mmol) of 2-cyclohexyl-4,7-dimethoxy-1,3-benzothiazole is put into suspension in an acetonitrile/water mixture (3/1) at 0° C. then 4.36 g (7.96 mmol; 2.2 eq.) of cerium (IV) and ammonium nitrate are added to the suspension. The reaction mixture is maintained for 1.5 hours under stirring at ambient temperature, then 0.78 g (yield=88%) of 2-cyclohexyl-1,3-benzothiazole-4,7-dione is obtained after filtration, washing with cold water and drying under reduced pressure.
NMR ¹H (DMSO d6, 400 MHz, δ): 6.90 (s, 2H); 3.15-3.10 (m, 1H, CH); 2.10-2.07 (m, 2H, CH$_2$); 1.81-1.77 (m, 2H, CH$_2$); 1.65-1.70 (m, 1H, CH); 1.55-1.39 (m, 5H, CH, CH$_2$).
MS-LC: MH+=248.12; r.t.=10.82 min.

101.5)
N-(2,5-dimethoxyphenyl)cyclohexanecarboxamide

The experimental protocol used is identical to that described for Stage 15.4 of Example 15, intermediate 101.4 replacing intermediate 15.3 and N,N-dimethylethylene diamine replacing aniline. A mixture of 80% and 9% of 2-cyclohexyl-5-{[2-(dimethylamino)ethyl]amino}-1,3-benzothiazole-4,7-dione and of 2-cyclohexyl-6-{[2-(dimethylamino)ethyl]amino}-1,3-benzothiazole-4,7-dione is obtained.
NMR ¹H (DMSO d6, 400 MHz, δ): 7.20 (t, 1H, NH); 5.49 and 5.43 (2s, H); 3.24-3.21 (m, 2H, CH$_2$); 3.09-3.12 (m, 3H, CH, CH$_2$); 2.19 (s, 6H, 2CH$_3$); 2.09-2.06 (m, 2H, CH$_2$); 1.80-1.77 (m, 3H, CH, CH$_2$); 1.53-1.49 (m, 4H, 2CH$_2$); 1.41-1.38 (m, 1H, CH).
MS-LC: MH+=334.17; r.t.=7.99 and 8.06 min.

The compounds of Examples 102 to 113 are obtained in a similar manner to that described for Example 101.

Example 102

Mixture of 2-cyclohexyl-5-[(2-pyrrolidin-1-ylethyl)amino]-1,3-benzothiazole-4,7-dione and 2-cyclohexyl-6-[(2-pyrrolidin-1-ylethyl)amino]-1,3-benzothiazole-4,7-dione MS-LC: MH+=360.16; r.t.=8.14 and 8.19 min.

Example 103

Mixture of 5-[(2-pyrrolidin-1-ylethyl)amino]-2-thien-2-yl-1,3-benzothiazole-4,7-dione and 6-[(2-pyrrolidin-1-ylethyl)amino]-2-thien-2-yl-1,3-benzothiazole-4,7-dione MS-LC: MH+=360.01; r.t.=7.78 and 7.86 min.

Example 104

Mixture of 2-(2,5-dichlorothien-3-yl)-5-{[2-(dimethylamino)ethyl]amino}-1,3-benzothiazole-4,7-dione and 2-(2,5-dichlorothien-3-yl)-6-{[2-(dimethylamino)ethyl]amino}-1,3-benzothiazole-4,7-dione MS-LC: MH+=401.86; r.t.=8.44 and 8.59 min.

Example 105

Mixture of 2-(2,5-dichlorothien-3-yl)-5-[(2-pyrrolidin-1-ylethyl)amino]-1,3-benzothiazole-4,7-dione and 2-(2,5-dichlorothien-3-yl)-6-[(2-pyrrolidin-1-ylethyl)amino]-1,3-benzothiazole-4,7-dione MS-LC: MH+=427.87; r.t.=8.63 and 8.80 min.

Example 106

Mixture of 2-(2-furyl)-5-[(2-pyrrolidin-1-ylethyl)amino]-1,3-benzothiazole-4,7-dione and 2-(2-furyl)-6-[(2-pyrrolidin-1-ylethyl)amino]-1,3-benzothiazole-4,7-dione MS-LC: MH+=344.04; r.t.=7.57 and 7.64 nmin.

Example 107

Mixture of 5-{[2-(dimethylamino)ethyl]amino}-2-(2-methoxyphenyl)-1,3-benzothiazole-4,7-dione and 6-{[2-(dimethylamino)ethyl]amino}-2-(2-methoxyphenyl)-1,3-benzothiazole-4,7-dione MS-LC: MH+=358.18; r.t.=7.88 and 7.97 min.

Example 108

Mixture of 5-{[2-(dimethylamino)ethyl]amino}-2-(2-fluorophenyl)-1,3-benzothiazole-4,7-dione and 6-{[2-(dimethylamino)ethyl]amino}-2-(2-fluorophenyl)-1,3-benzothiazole-4,7-dione MS-LC: MH+=346.14; r.t.=7.85 and 7.94 min.

Example 109

Mixture of 2-(2-fluorophenyl)-5-[(2-pyrrolidin-1-ylethyl)amino]-1,3-benzothiazole-4,7-dione and 2-(2-fluorophenyl)-6-[(2-pyrrolidin-1-ylethyl)amino]-1,3-benzothiazole-4,7-dione MS-LC: MH+=372.14; r.t.=7.97 and 8.06 nmin.

Example 110

Mixture of 2-(4-fluorophenyl)-5-[(2-pyrrolidin-1-ylethyl)amino]-1,3-benzothiazole-4,7-dione and 2-(4-fluorophenyl)-6-[(2-pyrrolidin-1-ylethyl)amino]-1,3-benzothiazole-4,7-dione MS-LC: MH+=372.05; r.t.=7.98 and 8.07 min.

Example 111

Mixture of 5-{[2-(dimethylamino)ethyl]amino}-2-(4-fluorophenyl)-1,3-benzothiazole-4,7-dione and 6-{[2-(dimethylamino)ethyl]amino}-2-(4-fluorophenyl)-1,3-benzothiazole-4,7-dione MS-LC: MH+=346.05; r.t.=7.87 and 7.95 min.

Example 112

Mixture of 2-(2,6-difluorophenyl)-5-[(2-pyrrolidin-1-ylethyl)amino]-1,3-benzothiazole-4,7-dione and 2-(2,6-difluorophenyl)-6-[(2-pyrrolidin-1-ylethyl)amino]-1,3-benzothiazole-4,7-dione MS-LC: MH+=390.04; r.t.=7.89 and 7.95 min.

Example 113

Mixture of 2-(2,6-difluorophenyl)-5-{[2-(dimethylamino)ethyl]amino}-1,3-benzothiazole-4,7-dione and 2-(2,6-difluorophenyl)-6-{[2-(dimethylamino)ethyl]amino}-1,3-benzothiazole-4,7-dione MS-LC: MH+=364.05; r.t.=7.78 and 7.83 min.

Example 114

5-[[2-(dimethylamino)ethyl](ethyl)amino]-2-methyl-1,3-benzothiazole-4,7-dione

This compound is obtained in a similar manner to that described for Example 1, N,N,N'-trimethylethylenediamine replacing 4-(2-aminoethyl)morpholine.

NMR $^1$H (DMSO d6, 400 MHz, δ): 5.53 (s, 1H, CH); 3.73-3.70 (t, 2H, CH$_2$); 2.93 (s, 3H, CH$_3$); 2.74 (s, 3H, CH$_3$); 2.32-2.30 (t, 2H, CH$_2$); 1.92 (s, 6H, 2CH$_3$).

MS-LC: MH+=280.11; r.t.=7.03 min.

Example 115

5-[[2-(dimethylamino)ethyl](methyl)amino]-2-methyl-1,3-benzothiazole-4,7-dione

This compound is obtained in a similar manner to that described for Example 1, N,N-dimethyl-N'-ethylenediamine replacing 4-(2-aminoethyl)morpholine.

MS-LC: MR+=294.07; r.t.=7.20 min.

Example 116

Mixture of 2-[2,6-dichloro-5-fluoro-3-pyridyl]-5-{[2-(dimethylamino)ethyl]amino}-1,3-benzoxazole-4,7-dione and 2-[2,6-dichloro-5-fluoro-3-pyridyl]-6-{[2-(dimethylainino)ethyl]amino}-1,3-benzoxazole-4,7-dione The experimental protocol used is identical to that described for Example 68, 2,6-dichloro-5-fluoronicotinonitrile replacing 2-bromobenzonitrile.

MS-LC: MH+=399.1; r.t.=8.1 min.

Example 117

Mixture of 2-[2,6-dichloro-5-fluoro-3-pyridyl]-5-[(2-pyrrolidin-1-ylethyl)amino]-1,3-benzoxazole-4,7-dione and 2-[2,6-dichloro-5-fluoro-3-pyridyl]-6-[(2-pyrrolidin-1-ylethyl)amino]-1,3-benzoxazole-4,7-dione The experimental protocol used is identical to that described for Example 68, 2,6-dichloro-5-fluoronicotinonitrile replacing 2-bromobenzonitrile and N-(2-aminoethyl)-pyrrolidine replacing NN-dimethylethylenediamine.

MS-LC: MH+=399.1; r.t.=8.1 min.

Example 118

Mixture of 2-(2,4-difluorophenyl)-5-{[2-(dimethylamino)ethyl]amino}-1,3-benzoxazole-4,7-dione and 2-(2,4-difluorophenyl)-6-{[2-(dimethylamino)ethyl]amino}-1,3-benzoxazole-4,7-dione The experimental protocol used is identical to that described for Example 68, 2,4-difluorobenzonitrile replacing 2-bromobenzonitrile.

MS-LC: MH+=348.1; r.t.=7.8 min.

Example 119

Mixture of 5-{[2-(dimethylamino)ethyl]amino}-2-(2,3,4-trifluorophenyl)-1,3-benzoxazole-4,7-dione and 6-{[2-(dimethylamino)ethyl]amino}-2-(2,3,4-trifluorophenyl)-1,3-benzoxazole-4,7-dione The experimental protocol used is identical to that described for Example 68, 2,3,4-trifluorobenzonitrile replacing 2-bromobenzonitrile. Melting point: 156° C.

MS-LC: MH+=366.1; r.t.=8.0 min.

Example 120

Mixture of 5-[(2-pyrrolidin-1-ylethyl)amino]-2-(2,3,4-trifluorophenyl)-1,3-benzoxazole-4,7-dione and 6-[(2-pyrrolidin-1-ylethyl)amino]-2-(2,3,4-trifluorophenyl)-1,3-benzoxazole-4,7-dione The experimental protocol used is identical to that described for Example 68, 2,3,4-trifluorobenzonitrile replacing 2-bromobenzonitrile and N-(2-aminoethyl)-pyrrolidine replacing N,N-dimethylethylenediamine.

MS-LC: MH+=392.1; r.t.=8.1 min.

Example 121

Mixture of 2-(3-fluoro-4-methylphenyl)-5-{[2-(dimethylamino)ethyl]amino}-1,3-benzoxazole-4,7-dione and 2-(3-fluoro-4-methylphenyl)-6-{[2-(dimethylamino)ethyl]amino}-1,3-benzoxazole-4,7-dione The experimental protocol used is identical to that described for Example 68, 3-fluoro-4-methylbenzonitrile replacing 2-bromobenzonitrile. Melting point: 179° C.

MS-LC: MH+=344.1; r.t.=8.1 min.

Example 122

Mixture of 2-(3-fluoro-4-methylphenyl)-5-[(2-pyrrolidin-1-ylethyl)amino]-1,3-benzoxazole-4,7-dione and 2-(3-fluoro-4-methylphenyl)-6-[(2-pyrrolidin-1-ylethyl)amino]-1,3-benzoxazole-4,7-dione The experimental protocol used is identical to that described for Example 68, 3-fluoro-4-methylbenzonitrile replacing 2-bromobenzonitrile and N-(2-aminoethyl)-pyrrolidine replacing N,N-dimethylethylenediamine.

MS-LC: MH+=370.1; r.t.=8.2 min.

The compounds of Examples 123 to 127 are obtained in a similar manner to that described for Example 101.

Example 123

Mixture of 2-(4-chlorophenyl)-5-{[2-(dimethylamino)ethyl]amino}-1,3-benzothiazole-4,7-dione and 2-(4-chlorophenyl)-6-{[2-(dimethylamino)ethyl]amino}-1,3-benzothiazole-4,7-dione MS-LC: MH+=362.07; r.t.=8.11 and 8.20 min.

Example 124

Mixture of 2-(4-chlorophenyl)-5-[(2-pyrrolidin-1-ylethyl)amino]-1,3-benzothiazole-4,7-dione and 2-(4-chlorophenyl)-6-[(2-pyrrolidin-1-ylethyl)amino]-1,3-benzothiazole-4,7-dione MS-LC: MH+=388.04; r.t.=8.23 and 8.34 min.

Example 125

Mixture of 5-{[2-(dimethylamino)ethyl]amino}-2-(2,3,4,5-tetrafluorophenyl)-1,3-benzothiazole-4,7-dione and 6-{[2-(dimethylamino)ethyl]amino}-2-(2,3,4,5-tetrafluorophenyl)-1,3-benzothiazole-4,7-dione MS-LC: MH+=400.01; r.t.=8.23 and 8.32 min.

Example 126

Mixture of 5-{[2-(dimethylamino)ethyl]amino}-2-(3,4,5-trifluorophenyl)-1,3-benzothiazole-4,7-dione and 6-{[2-(dimethylamino)ethyl]amino}-2-(3,4,5-trifluorophenyl)-1,3-benzothiazole-4,7-dione MS-LC: MH+=382.03; r.t.=8.10 and 8.19 min.

Example 127

Mixture of 5-[(2-pyrrolidin-1-ylethyl)amino]-2-(2,4,6-trifluorophenyl)-1,3-benzothiazole-4,7-dione and 6-[(2-pyrrolidin-1-ylethyl)amino]-2-(2,4,6-trifluorophenyl)-1,3-benzothiazole-4,7-dione MS-LC: MH+=408.02; r.t.=7.97 and 8.05 min.

The compounds of Examples 128 to 131 are obtained in a similar manner to that described for Example 66.

Example 128

Mixture of 2-(1,3-benzodioxol-5-yl)-5-{[2-(dimethylamino)ethyl]amino}-1,3-benzoxazole-4,7-dione and 2-(1,3-benzodioxol-5-yl)-6-{([2-(dimethylamino)ethyl]amino}-1,3-benzoxazole-4,7-dione The two components of the mixture can be characterized by the NMR shifts (400 MHz) of the single proton of the benzoxazoledione ring which are 5.35 and 5.37 ppm.

MS-LC: MH+=356.07; r.t.=7.72 min.

Example 129

Mixture of 5-{[2-(dimethylamino)ethyl]amino}-2-(4-ethylphenyl)-1,3-benzoxazole-4,7-dione and of 6-{[2-(dimethylamino)ethyl]amino}-2-(4-ethylphenyl)-1,3-benzoxazole-4,7-dione The two components of the mixture can be characterized by the NMR shifts (400 MHz) of the single proton of the benzoxazoledione ring which are 5.36 and 5.38 ppm.

MS-LC: MH+=340.18; r.t.=8.24 min.

Example 130

Mixture of 2-(4-ethylphenyl)-5-[(2-pyrrolidin-1-ylethyl)amino]-1,3-benzoxazole-4,7-dione and 2-(4-ethylphenyl)-6-[(2-pyrrolidin-1-ylethyl)amino]-1,3-benzoxazole-4,7-dione The two components of the mixture can be characterized by the NMR shifts (400 MHz) of the single proton of the benzoxazoledione ring which are 5.35 and 5.36 ppm.
MS-LC: MH+=366.15; r.t.=8.34 min.

Example 131

Mixture of 5-{[2-(dimethylamino)ethyl]amino}-2-(2-fluoro-6-methoxyphenyl)-1,3-benzoxazole-4,7-dione and 6-{[2-(dimethylamino)ethyl]amino}-2-(2-fluoro-6-methoxyphenyl)-1,3-benzoxazole-4,7-dione The two components of the mixture can be characterized by the NMR shifts (400 MHz) of the single proton of the benzoxazoledione ring which are 5.39 and 5.40 ppm.
MS-LC: MH+=360.09; r.t.=7.67 min.

Pharmacological Study of the Compounds of the Invention

Test Protocols i) Measurement of the Phosphatase Activity of the Purified Cdc25C Recombinant Enzyme The phosphatase activity of the MBP-Cdc25C protein is evaluated by dephosphorylation of 3-O-methylfluorescein-phosphate (OMFP) to 3-O-methylfluorescein (OMF) with determination of the fluorescence of the reaction product at 475 nm. This test allows identification of the inhibitors of cdc25 recombinant enzyme. The preparation of the fusion protein MBP-cdc25C is described in PCT Patent Application WO 01/44467.

The reaction is carried out in 384-well plate format in a final volume of 50 μl. The MBP-Cdc25C protein (prepared as described above) is stored in the following elution buffer: 20 mM Tris-HCl pH 7.4; 250 mM NaCl; 1 mM EDTA; 1 mM of dithiothreitol (DTT); 10 mM maltose. It is diluted to a concentration of 60 μM in the following reaction buffer: 50 mM Tris-HCl pH 8.2; 50 mM NaCl; 1 mM DTT; 20% glycerol. Measurement of the background noise is carried out with the buffer without addition of the enzyme. The products are tested at decreasing concentrations starting from 40 μM. The reaction is initiated by the addition of an OMFP solution at 500 μM final (prepared extemporaneously from a 12.5 mM stock solution in 100% DMSO (Sigma #M2629)). After 4 hours at 30° C. in a disposable 384-well plate, the fluorescence measured at OD 475 nm is read using a Victor$^2$ plate reader (EGG-Wallac). Determination of the 50% inhibitory concentration of the enzymatic reaction is calculated from three independent experiments. Only the values included in the linear part of the sigmoid are retained for linear regression analysis.

ii) Measurement of the Tyrosine Phosphatase Activity of the CD45 Enzyme:

Measurement of the tyrosine phosphatase activity of CD45 is based on the dephosphorylation of the peptide pp60$^{c-src}$ by CD45. Only the cytoplasmic domain of purified human CD45 enzyme (amino acids 584 to 1281, molecular weight=95 kDa) expressed in a yeast expression system is used for the measurement. The substrate is a synthetic peptide based on the sequence of the negative regulatory domain of pp60$^{c-src}$. The phosphate released is measured by a malachite green type reagent.

The reaction is carried out in 384-well plate format with a final volume of 20 μl. The substrate pp60$^{c-src}$ (P-301, BIOMOL, Plymouth Meeting, Pa., USA) is diluted to a concentration of 925 μM in the following reaction buffer: 50 mM Hepes pH 7.2; 1 mM EDTA; 1 mM of dithiothreitol (DTT); 0.05% NP-40 surfactant. The final substrate concentration is 185 μM. The candidate products are tested in a range of decreasing concentrations starting from 160 μM. The reaction is initiated by adding CD45 (SE-135, BIOMOL, Plymouth Meeting, Pa., USA) at 15 U/μl (1 U=1 pmol/min) diluted in reaction buffer. The final enzyme concentration is 1.75 U/μl. After incubating for 1 hour at 30° C., BIOMOL Green Reagent (AK-111, BIOMOL, Plymouth Meeting, Pa., USA) is added in a volume of 50 μl/well. After 20 to 30 minutes during which the colour develops, absorbance at 620 nm is read using a Victor$^2$ plate reader (EGG-Wallac). Determination of the 50% inhibitory concentration of the enzyme reaction is calculated from three independent experiments.

iii) Characterization of the Antiproliferative Activity:

By way of example, the effect of a treatment on two human cell lines Mia-Paca2 and DU145 by the compounds of the examples described previously will be studied. The cell lines DU145 (human prostate cancer cells) and Mia-PaCa2 (human pancreas cancer cells) were acquired from the American Tissue Culture Collection (Rockville, Md., USA). The cells placed in 80 μl of Dulbecco's Modified Eagle's medium (Gibco-Brl, Cergy-Pontoise, France) completed with 10% foetal calf serum inactivated by heating (Gibco-Brl, Cergy-Pontoise, France), 50,000 units/l of penicillin and 50 mg/l of streptomycin (Gibco-Brl, 10378-057, Cergy-Pontoise, France), and 2 mM of glutamine (Gibco-Brl, Cergy-Pontoise, France) were seeded on a 96-well plate on day 0. The cells were treated on day 1 for 96 hours with increasing concentrations of each of the compounds to be tested up to 10 μM. At the end of this period, quantification of cell proliferation is evaluated by a colorimetric test based on the cleavage of the tetrazolium salt WST1 by the mitochondrial dehydrogenases in viable cells leading to the formation of formazan (Boehringer Mannheim, Meylan, France). These tests are carried out in duplicate with 8 determinations per concentration tested. For each compound to be tested, the values included in the linear part of the sigmoid were retained for a linear regression analysis and used to estimate the inhibitory concentration IC$_{50}$. The products are solubilized in dimethylsulphoxide (DMSO) at 10$^{-2}$ M and used in culture with 0.1% DMSO final.

Results of the Tests a) The compounds of Examples 1 to 98, 101 to 104 and 107 to 115 have a CI$_{50}$ below or equal to 10 μM on the phosphatase activity of the purified recombinant enzyme Cdc25-C.

b) The compounds of Examples 1 to 5 have a CI$_{50}$ below or equal to 10 μM on the tyrosine phosphatase activity of the enzyme CD45.

c) The compounds of Examples 1 to 9, 11, 14 to 34, 36 to 53, 55 to 58, 60 to 98 and 101 to 115 have a CI$_{50}$ below or equal to 10 μM on the cell proliferation of the lines Mia-Paca2.

d) The compounds of Examples 1 to 9, 11, 14 to 34, 36 to 53, 55 to 58, 60 to 98 and 101 to 115 have a CI$_{50}$ below or equal to 10 μM on the cell proliferation of the lines DU-145.

What is claimed is:

1. A method of treating human prostate cancer or human pancreas cancer in a warm-blooded animal comprising administering to a warm-blooded animal in need thereof an inhibiting amount of a compound of the formula

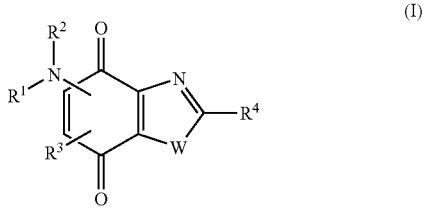

wherein
$R^1$ is —(CH$_2$)—Z—NR$^5$R$^6$,
Z is a bond or alkylene of 1 to 5 carbon atoms,
$R^5$ is hydrogen, alkyl, aralkyl, —(CH$_2$)$_n$—OH, wherein n is an integer of 1 to 6, alkoxycarbonyl, haloalkylcarbonyl or aralkoxycarbonyl, and
$R^6$ is hydrogen, alkyl, aralkyl or —(CH$_2$)$_n$—HO,
$R^2$ is hydrogen, alkyl or aralkyl;
$R^3$ is hydrogen, alkyl, haloalkyl, alkoxy or alkylthio;
$R^4$ is alkyl, cycloalkyl, cycloalkylalkyl, cyano or amino,
W is S;
or a pharmaceutically acceptable salt thereof.

2. The method of claim 1 wherein:
$R^2$ is hydrogen, methyl, ethyl, or benzyl
$R^3$ is hydrogen, alkyl, alkoxy, or alkylthio;
$R^4$ is alkyl or a carbocyclic.

3. A method of treating human prostate cancer or human pancreas cancer in a warm-blooded animal comprising administering to a warm-blooded animal in need thereof an inhibiting amount of:

-5 {[2-(dimethylamino)ethyl]amino}-2-methyl-1,3-benzothiazole-4,7-dione;
-5 {[6-(dimethylamino)hexyl]amino}-2-methyl-1,3-benzothiazole-4,7-dione;
-5[(1-ethylhexyl)amino]-2-methyl-1,3-benzothiazole-4,7-dione;
-2-methyl-5-(propylamino)-1,3-benzothiazole-4,7-dione;
-5-[(2-methoxyethyl)amino]-2-methyl-1,3-benzothiazole-4,7-dione;
-5-{[2-(diisopropylamino)ethyl]amino}-2-methyl-1,3-benzothiazole-4,7-dione;
-5-{[3-(dimethylamino)propyl]amino}-2-methyl-1,3-benzothiazole-4,7-dione;
-5-{[4-(dimethylamino)butyl]amino}-2-methyl-1,3-benzothiazole-4,7-dione;
-5-{[5-(dimethylamino)pentyl]amino}-2-methyl-1,3-benzothiazole-4,7-dione;
-5-{benzy[2-(dimethylamino)ethyl]amino}-2-methyl-1,3-benzothiazole-4,7-dione;
-2-methyl-5-{[3-(methylamino)propyl]amino}-1,3-benzothiazole-4,7-dione;
-5-[(3-aminopropyl)amino]-2-methyl-1,3-benzothiazole-4,7-dione;
-6-(butylthio)-5-{[2-(dimethylamino)ethyl]amino}-2-methyl-1,3-benzothiazole-4,7-dione;
-2-cyciohexyl-5-[(2-pyrrolidin-1-ylethyl)amino]-1,3-benzothiazole-4,7-dione;
-2-cyclohexyl-6-[(2-pyrrolidin-1-ylethyl)amino]-1,3-benzothiazole-4,7-dione;
-5-[[2-(dimethylamino)ethyl](ethyl)amino]-2-methyl-1,3-benzothiazole-4,7-dione;
-5-[[2-(dimethylamino)ethyl](methyl)amino]-2-methyl-1,3-benzothiazole-4,7-dione;

or a pharmaceutically acceptable salt thereof.

* * * * *